(12) United States Patent
Johansson et al.

(10) Patent No.: US 7,402,581 B2
(45) Date of Patent: Jul. 22, 2008

(54) AZETIDINE COMPOUNDS

(75) Inventors: Anders Johansson, Mölndal (SE);
Joachim Persson, Mölndal (SE)

(73) Assignee: Albireo AB, Gothenburg (SE)

( * ) Notice: Subject to any disclaimer, the term of this patent is extended or adjusted under 35 U.S.C. 154(b) by 395 days.

(21) Appl. No.: 10/560,319

(22) PCT Filed: Jun. 9, 2004

(86) PCT No.: PCT/SE2004/000901

§ 371 (c)(1),
(2), (4) Date: Dec. 9, 2005

(87) PCT Pub. No.: WO2004/110344

PCT Pub. Date: Dec. 23, 2004

(65) Prior Publication Data

US 2006/0172988 A1    Aug. 3, 2006

(30) Foreign Application Priority Data

Jun. 13, 2003  (SE) .................................. 0301744
Dec. 19, 2003  (SE) .................................. 0303493

(51) Int. Cl.
 C07D 409/02   (2006.01)
 C07D 403/02   (2006.01)
 A61K 31/498   (2006.01)
 A61K 31/4709  (2006.01)

(52) U.S. Cl. .................. 514/235.5; 514/252.13; 514/326; 546/208; 544/111; 544/359

(58) Field of Classification Search ................ 544/111, 544/359; 514/235.5, 252.13, 326; 546/208
See application file for complete search history.

(56) References Cited

U.S. PATENT DOCUMENTS 6,013,652 A    1/2000    Maccoss et al.

FOREIGN PATENT DOCUMENTS

| EP | 625509 A1 | 11/1994 |
|---|---|---|
| EP | 625509 B1 | 11/1994 |
| EP | 630887 A1 | 12/1994 |
| EP | 790-248 B1 | 8/1997 |
| EP | 791592 B1 | 8/1997 |
| EP | 962457 B1 | 12/1999 |
| WO | WO-95/05377 | 2/1995 |
| WO | WO-95/12577 | 5/1995 |
| WO | WO-95/15691 | 6/1995 |
| WO | WO-96/05193 | 2/1996 |
| WO | WO-96/10568 | 4/1996 |
| WO | WO-96/24582 | 8/1996 |
| WO | WO-97/25322 | 7/1997 |
| WO | WO-97/27185 | 7/1997 |
| WO | WO-99/01451 | 1/1999 |
| WO | WO-00/02859 | 1/2000 |
| WO | WO-00/20003 | 4/2000 |
| WO | WO-00/20389 | 4/2000 |
| WO | WO-00/25766 | 5/2000 |
| WO | WO-00/34243 | 6/2000 |
| WO | WO-02/051807 A1 | 7/2002 |
| WO | WO-03/037889 A1 | 5/2003 |

OTHER PUBLICATIONS

"4-Amino-2-(aryl)-butylbenzamines and their Conformationally Constrained Analogues. Potent Antagonists of the Human Neurokinin-2 ($NK_2$) Receptor", Mackenzie et al., Bioorg. Med. Chem. Lett., vol. 13, No. 13, Jul. 7, 2003, pp. 2211-2215(5); available online May 15, 2003.

*Primary Examiner*—Kahsay T Habte
(74) *Attorney, Agent, or Firm*—White & Case LLP

(57) ABSTRACT

The present invention relates to a compound of the general formula (I) wherein Het is an optionally substituted 4-, 5-, 6- or 7-membered heterocyclic ring having at least one nitrogen atom; R1 is hydrogen, hydroxy, $C_1$-$C_4$ alkyl, $C_3$-$C_4$ cycloalkyl, $C_2$-$C_4$ alkenyl or $C_2$-$C_4$ alkynyl; R2 and R3 is each and independently selected from hydrogen, $C_1$-$C_4$ alkyl, $C_3$-$C_4$ cycloalkyl, $C_2$-$C_4$ alkenyl, $C_2$-$C_4$ alkynyl, $C_1$-$C_4$ alkoxy, halogen and cyano, provided that R2 and R3 may not both be hydrogen; R4 is $C_1$-$C_4$ alkyl, $C_3$-$C_4$ cycloalkyl, $C_2$-$C_4$ alkenyl or $C_2$-$C_4$ alkynyl; Ar is an optionally substituted aromatic ring system selected from pyridinyl; 1-naphthyl; 5,6,7,8-tetrahydro-1-naphthyl; quinolinyl; 2,3-dihydro-1,4-benzodioxinyl; 1,3-benzodioxolyl; 5,6,7,8-tetrahydroquinolinyl; 5,6,7,8-tetrahydroisoquinolinyl; 5,6,7,8-tetrahydroquinazolin-4-yl; 1-benzo[b]thiophen-7-yl; 1-benzo[b]thiophen-4-yl; 1-benzo[b]thiophen-3-yl; isoquinolinyl; quinazolinyl; and indan-4-yl; or Ar is substituted phenyl; or an enantiomer thereof or any salt thereof; to a pharmaceutical composition containing said compounds and to the use of said compounds in therapy. The present invention further relates to processes for the preparation of compounds of formula I and to new intermediates used in the preparation thereof.

(I)

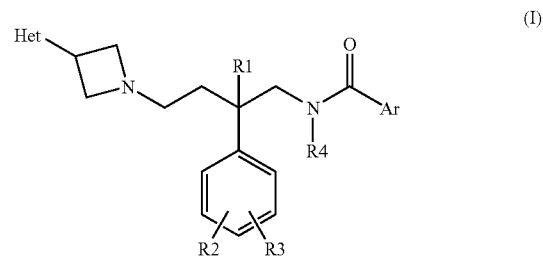

15 Claims, No Drawings

AZETIDINE COMPOUNDS

FIELD OF THE INVENTION

The present invention relates to new compounds of formula I, to pharmaceutical compositions containing said compounds and to the use of said compounds in therapy. The present invention further relates to processes for the preparation of compounds of formula I and to new intermediates used in the preparation thereof.

BACKGROUND OF THE INVENTION

The neurokinins, also known as the tachykinins, comprise a class of peptide neurotransmitters which are found in the peripheral and central nervous systems. The three principal tachykinins are Substance P (SP), Neurokinin A (NKA) and Neurokinin B (NKB). At least three receptor types are known for the three principal tachykinins. Based upon their relative selectivities favouring the agonists SP, NKA and NKB, the receptors are classified as neurokinin 1 ($NK_1$), neurokinin 2 ($NK_2$) and neurokinin 3 ($NK_3$) receptors, respectively.

There is a need for an orally active and blood brain barrier crossing dual $NK_1/NK_2$ receptor antagonist for the treatment of e.g. respiratory, cardiovascular, neuro, pain, oncology, inflammatory and/or gastrointestinal disorders. In order to increase the therapeutic index of such therapy it is desirable to obtain such a compound possessing no or minimal toxicity as well as being selective to said NK receptors. Furthermore, it is considered necessary that said medicament has favourable pharmacokinetic and metabolic properties thus providing an improved therapeutic and safety profile such as lower liver enzyme inhibiting properties.

It is well known that severe problems such as toxicity may occur if plasma levels of one medication are altered by the co-administration of another drug. This phenomenon—which is named drug-drug interactions—could happen if there is a change in the metabolism of one drug caused by the co-administration of another substance possessing liver enzyme inhibiting properties. CYP (cytochrome P450) 3A4 is the most important enzyme in the human liver as a majority of oxidised drugs have been biotransformed by this enzyme. Accordingly, it is undesirable to employ a medication having a significant degree of such liver enzyme inhibiting properties. It has now been found that many NK receptor antagonists known in the art inhibit the CYP3A4 enzyme to a certain level and consequently there is a possible risk if high doses of those compounds are being used in therapy. Thus, there is a need for a novel dual $NK_1/NK_2$ receptor antagonist with improved pharmacokinetic properties. The present invention provides compounds with CYP3A4 enzyme inhibiting properties at a low level, as comparatively high $IC_{50}$ values are obtained in a CYP3A4 inhibiting assay. Said method for determining CYP3A4 inhibition is described in Bapiro et al; Drug Metab. Dispos. 29, 30-35 (2001).

EP 0625509, EP 0630887, WO 95/05377, WO 95/12577, WO 95/15961, WO 96/24582, WO 00/02859, WO 00/20003, WO 00/20389, WO 00/25766, WO 00/34243, WO 02/51807 and WO 03/037889 disclose piperidinylbutylamide derivatives, which are tachykinin antagonists.

"4-Amino-2-(aryl)-butylbenzamides and Their Conformationally Constrained Analogues. Potent Antagonists of the Human Neurokinin-2 ($NK_2$) Receptor", Roderick MacKenzie, A., et al, *Bioorganic & Medicinal Chemistry Letters*, In Press, available online 15 May 2003, discloses the compound N-[2-(3,4-dichlorophenyl)-4-(3-morpholin-4-ylazetidin-1-yl)butyl]-N-methylbenzamide which was found to possess functional $NK_2$ receptor antagonistic properties.

WO 96/05193, WO 97/27185 and EP 0962457 disclose azetidinylalkyllactam derivatives with tachykinin antagonist activity.

EP 0790248 discloses azetidinylalkylazapiperidones and azetidinylalkyloxapiperidones, which are stated to be tachykinin antagonists.

WO 99/01451 and WO 97/25322 disclose azetidinylalkylpiperidine derivatives claimed to be tachykinin antagonists.

EP 0791592 discloses azetidinylalkylglutarimides with tachykinin antagonistic properties.

An object of the present invention was to provide novel tachykinin antagonists useful in therapy. A further object was to provide novel compounds having blood brain barrier penetrating properties, improved pharmacokinetic and metabolic properties and/or improved selectivity for the $NK_1/NK_2$ receptors.

OUTLINE OF THE INVENTION

The present invention provides a compound of the general formula (I)

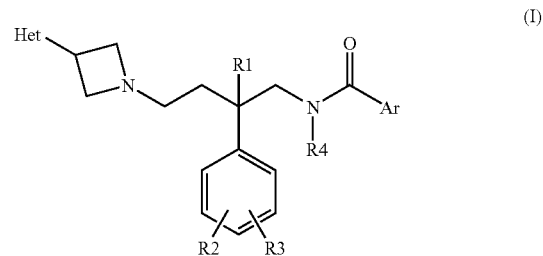

wherein
- Het is an optionally substituted 4-, 5-, 6- or 7-membered heterocyclic ring having at least one nitrogen atom;
- R1 is hydrogen, hydroxy, $C_1$-$C_4$ alkyl, $C_3$-$C_4$ cycloalkyl, $C_2$-$C_4$ alkenyl or $C_2$-$C_4$ alkynyl;
- R2 and R3 is each and independently selected from hydrogen, $C_1$-$C_4$ alkyl, $C_3$-$C_4$ cycloalkyl, $C_2$-$C_4$ alkenyl, $C_2$-$C_4$ alkyl, $C_1$-$C_4$ alkoxy, halogen and cyano, provided that R2 and R3 may not both be hydrogen;
- R4 is $C_1$-$C_4$ alkyl, $C_3$-$C_4$ cycloalkyl, $C_2$-$C_4$ alkenyl or $C_2$-$C_4$ alkynyl;
- Ar is an optionally substituted aromatic ring system selected from pyridinyl; 1-naphthyl; 5,6,7,8-tetrahydro-1-naphthyl; quinolinyl; 2,3-dihydro-1,4-benzodioxinyl; 1,3-benzodioxolyl; 5,6,7,8-tetrahydroquinolinyl; 5,6,7,8-tetrahydroisoquinolinyl; 5,6,7,8-tetrahydroquinazolin-4-yl; 1-benzo[b]thiophen-7-yl; 1-benzo[b]thiophen-4-yl; 1-benzo[b]thiophen-3-yl; isoquinolinyl; quinazolinyl; and indan-4-yl; or Ar is substituted phenyl;

or an enantiomer thereof or any salt thereof.

In one embodiment of the present invention, the heterocyclic ring Het is connected to the rest of the molecule at one of the nitrogen atoms of the ring. Examples of such heterocyclic rings are optionally substituted 1,4-dioxa-8-azaspiro[4.5]decano; optionally substituted piperidino; optionally substituted azepano; optionally substituted pyrrolidino; optionally substituted morpholino; optionally substituted oxazepano; optionally substituted thiomorpholino; optionally substituted thiazepano; and optionally substituted piperazino.

In further embodiments of the present invention Het is piperidino optionally substituted with hydroxy, hydroxyalkyl, oxo, methylthio, methylsulfinyl, methylsulfonyl, cyano, 1,3-dioxolan-2-yl, $C_1$-$C_4$ alkoxy, amino optionally mono or disubstituted with $C_1$-$C_4$ alkyl, $C_3$-$C_4$ cycloalkyl, $C_2$-$C_4$ alkenyl, $C_2$-$C_4$ alkynyl, acylamino optionally N-substituted with $C_1$-$C_4$ alkyl, $C_3$-$C_4$ cycloalkyl, $C_2$-$C_4$ alkenyl, $C_2$-$C_4$ alkynyl, ($C_1$-$C_4$ alkylsulfonyl)amino optionally N-substituted by $C_1$-$C_4$ alkyl, $C_3$-$C_4$ cycloalkyl, $C_2$-$C_4$ alkenyl, $C_2$-$C_4$ alkynyl, one or two fluoro atoms or disubstituted by $C_1$-$C_4$ alkyl and hydroxy; pyrrolidino optionally substituted at its three position by fluoro, hydroxy or oxo; morpholino or thiomorpholino optionally substituted at its sulfur atom by one or two oxygen; or piperazino optionally substituted at the 4-nitrogen atom by $C_1$-$C_4$ alkyl.

Ar may optionally be substituted at one or more of its carbon atoms by one or more groups independently selected from cyano, halogen, $C_1$-$C_4$ alkyl, $C_3$-$C_4$ cycloalkyl, $C_2$-$C_4$ alkenyl, $C_2$-$C_4$ alkynyl, $C_1$-$C_4$ alkoxy, nitro, trifluoromethoxy, difluoromethoxy, trifluoromethyl, $C_1$-$C_4$ alkylsulfinyl, $C_1$-$C_4$ alkylsulfonyl, $C_1$-$C_4$ alkylthio, trifluoromethylsulfonyloxy, $C_1$-$C_4$ alkyl sulfonyl or $C_1$-$C_4$ acyl.

In one embodiment of the present invention, Ar is phenyl substituted by one or more groups independently selected from cyano, halogen, $C_1$-$C_4$ alkyl, $C_3$-$C_4$ cycloalkyl, $C_2$-$C_4$ alkenyl, $C_2$-$C_4$ alkynyl, $C_1$-$C_4$ alkoxy, nitro, trifluoromethoxy, difluoromethoxy, $C_1$-$C_4$ alkylsulfinyl, $C_1$-$C_4$ alkylsulfonyl, $C_1$-$C_4$ alkylthio, trifluoromethylsulfonyloxy, $C_1$-$C_4$ alkyl sulfonyl or $C_1$-$C_4$ acyl.

In a further embodiment of the present invention, Ar is phenyl substituted in its 3- and 5-position by groups independently selected from halogen, $C_1$-$C_4$ alkyl, $C_1$-$C_4$ alkoxy, cyano and nitro. Optionally, Ar may additionally also be substituted in its 2- and/or 4-position by a group independently selected from halogen, $C_1$-$C_4$ alkyl and $C_1$-$C_4$ alkoxy.

In one embodiment of the present invention, R1 is hydrogen.

In one embodiment of the present invention, R2 and R3 are both chloro or one is fluoro and the other is hydrogen. In a further embodiment of the invention, R2 and R3 are both chloro and attached in the three and four position of the phenyl ring or R2 is fluoro attached in the four position and R3 is hydrogen.

In one embodiment of the present invention, R4 is methyl.

In one embodiment of the present invention, the compound of formula I is the S-enantiomer or the racemate. In a further embodiment of the invention, the compound of formula I is the S-enantiomer.

A further aspect of the invention relates to compounds of formula I, wherein

Het is thiomorpholino, morpholino or oxidothiomorpholino;

R1 is H;

R2 is fluoro and R3 is hydrogen, fluoro being preferably in para position;

Ar is 3-cyano-5,6,7,8-tetrahydro-1-naphthyl; and

R4 is as defined above.

In a further aspect of the invention the following compounds are provided:

3,5-Dichloro-N-[(2S)-2-(3,4-dichlorophenyl)-4-(3-thiomorpholin-4-ylazetidin-1-yl)butyl]-N-methylbenzamide;

3,5-Dibromo-N-[(2S)-2-(4-fluorophenyl)-4-(3-morpholin-4-ylazetidin-1-yl)butyl]-N-methylbenzamide;

N-[(2S)-2-(3,4-Dichlorophenyl)-4-(3-thiomorpholin-4-ylazetidin-1-yl)butyl]-3,5-difluoro-N-methylbenzamide;

N-[(2S)-2-(3,4-Dichlorophenyl)-4-(3-thiomorpholin-4-ylazetidin-1-yl)butyl]-N-methyl-3,5-bis(trifluoromethyl)benzamide;

5-Cyano-N-[(2S)-2-(3,4-dichlorophenyl)-4-(3-thiomorpholin-4-ylazetidin-1-yl)butyl]-N-methyl-1-benzothiophene-7-carboxamide;

3-Cyano-N-[(2S)-2-(3,4-dichlorophenyl)-4-(3-thiomorpholin-4-ylazetidin-1-yl)butyl]-N-methylbenzamide;

3-Cyano-N-[(2S)-2-(3,4-dichlorophenyl)-4-(3-thiomorpholin-4-ylazetidin-1-yl)butyl]-N-methyl-5,6,7,8-tetrahydronaphthalene-1-carboxamide;

2-Cyano-N-[(2S)-2-(3,4-dichlorophenyl)-4-(3-thiomorpholin-4-ylazetidin-1-yl)butyl]-N-methylquinoline-4-carboxamide;

3-Cyano-N-[2-(4-fluorophenyl)-4-(3-thiomorpholin-4-ylazetidin-1-yl)butyl]-N-methyl-5,6,7,8-tetrahydronaphthalene-1-carboxamide;

N-[2-(4-Fluorophenyl)-4-(3-thiomorpholin-4-ylazetidin-1-yl)butyl]-N-methyl-3,5-bis(trifluoromethyl)benzamide;

7-Chloro-N-[(2S)-2-(3,4-dichlorophenyl)-4-(3-thiomorpholin-4-ylazetidin-1-yl)butyl]-N-methyl-2,3-dihydro-1,4-benzodioxine-5-carboxamide;

N-{(2S)-2-(3,4-Dichlorophenyl)-4-[3-(1-oxidothiomorpholin-4-yl)azetidin-1-yl]butyl}-2-methoxy-N-methylquinoline-4-carboxamide;

3-Fluoro-N-[(2S)-2-(4-fluorophenyl)-4-(3-morpholin-4-ylazetidin-1-yl)butyl]-N-methyl-5-(trifluoromethyl)benzamide;

3-Cyano-N-{2-(4-fluorophenyl)-4-[3-(4-hydroxypiperidin-1-yl)azetidin-1-yl]butyl}-N-methyl-5,6,7,8-tetrahydronaphthalene-1-carboxamide;

N-[4-[3-(1,4-Dioxa-8-azaspiro[4.5]dec-8-yl)azetidin-1-yl]-2-(4-fluorophenyl)butyl]-N-methyl-3,5-bis(trifluoromethyl)benzamide;

N-{(2S)-2-(3,4-Dichlorophenyl)-4-[3-(4-fluoropiperidin-1-yl)azetidin-1-yl]butyl}-N-methyl-3,5-bis(trifluoromethyl)benzamide;

N-{(2S)-2-(3,4-Dichlorophenyl)-4-[3-(4-hydroxypiperidin-1-yl)azetidin-1-yl]butyl}-N-methyl-3,5-bis(trifluoromethyl)benzamide;

3-Cyano-N-{(2S)-2-(3,4-dichlorophenyl)-4-[3-(3-hydroxypyrrolidin-1-yl)azetidin-1-yl]butyl}-N-methyl-1-naphthamide;

N-{(2S)-2-(4-Fluorophenyl)-4-[3-(4-fluoropiperidin-1-yl)azetidin-1-yl]butyl}-N-methyl-3,5-bis(trifluoromethyl)benzamide;

3-Cyano-N-[(2S)-2-(4-fluorophenyl)-4-(3-morpholin-4-ylazetidin-1-yl)butyl]-N-methyl-5,6,7,8-tetrahydronaphthalene-1-carboxamide;

N-{(2S)-2-(4-fluorophenyl)-4-[3-(4-hydroxypiperidin-1-yl)azetidin-1-yl]butyl}-N-methyl-3,5-bis(trifluoromethyl)benzamide;

3,5-Dichloro-N-[(2S)-2-(4-fluorophenyl)-4-(3-morpholin-4-ylazetidin-1-yl)butyl]-N-methylbenzamide;

3-Cyano-N-[(2S)-2-(3,4-dichlorophenyl)-4-(3-morpholin-4-ylazetidin-1-yl)butyl]-N-methyl-1-naphthamide;

3-Cyano-N-[(2S)-2-(3,4-dichlorophenyl)-4-(3-thiomorpholin-4-ylazetidin-1-yl)butyl]-N-methyl-1-naphthamide;

3-Cyano-N-{(2S)-2-(3,4-dichlorophenyl)-4-[3-(1,4-dioxa-8-azaspiro[4.5]dec-8-yl)azetidin-1-yl]butyl}-N-methyl-1-naphthamide;

3-Cyano-N-{(2S)-2-(3,4-dichlorophenyl)-4-[3-(4-hydroxypiperidin-1-yl)azetidin-1-yl]butyl}-N-methyl-1-naphthamide;

3-Cyano-N-[2-(4-fluorophenyl)-4-(3-thiomorpholin-4-ylazetidin-1-yl)butyl]-N-methyl-1-naphthamide;

3-Cyano-N-[2-(4-cyanophenyl)-4-(3-thiomorpholin-4-ylazetidin-1-yl)butyl]-N-methyl-1-naphthamide;

3-Cyano-N-{(2S)-2-(3,4-dichlorophenyl)-4-[3-(1,1-dioxidothiomorpholin-4-yl)azetidin-1-yl]butyl}-N-methyl-1-naphthamide;

3-Cyano-N-{(2S)-2-(4-fluorophenyl)-4-[3-(4-hydroxypiperidin-1-yl)azetidin-1-yl]butyl}-N-methyl-5,6,7,8-tetrahydronaphthalene-1-carboxamide;

3-Cyano-N-ethyl-N-[(2S)-2-(4-fluorophenyl)-4-(3-morpholin-4-ylazetidin-1-yl)butyl]-5,6,7,8-tetrahydronaphthalene-1-carboxamide;

3-Cyano-N-[(2S)-4-[3-(1,4-dioxa-8-azaspiro[4.5]dec-8-yl)azetidin-1-yl]-2-(4-fluorophenyl)butyl]-N-methyl-5,6,7,8-tetrahydronaphthalene-1-carboxamide;

3-cyano-N-[(2S)-2-(4-fluorophenyl)-4-(3-morpholin-4-ylazetidin-1-yl)butyl]-N-methyl-1-naphthamide;

3-Cyano-N-{(2S)-2-(4-fluorophenyl)-4-[3-(1,4-oxazepan-4-yl)azetidin-1-yl]butyl}-N-methyl-5,6,7,8-tetrahydronaphthalene-1-carboxamide;

3-Fluoro-N-[(2S)-2-(4-fluorophenyl)-4-(3-morpholin-4-ylazetidin-1-yl)butyl]-N-methyl-5,6,7,8-tetrahydronaphthalene-1-carboxamide;

3,5-Dibromo-N-{(2S)-2-(4-fluorophenyl)-4-[3-(4-hydroxypiperidin-1-yl)azetidin-1-yl]butyl}-N-methylbenzamide;

3-Bromo-N-[(2S)-2-(4-fluorophenyl)-4-(3-morpholin-4-ylazetidin-1-yl)butyl]-5-iodo-N-methylbenzamide;

3-Cyano-N-[2-(4-fluoro-2-methylphenyl)-4-(3-morpholin-4-ylazetidin-1-yl)butyl]-N-methyl-5,6,7,8-tetrahydronaphthalene-1-carboxamide;

6-Cyano-N-[(2S)-2-(4-fluorophenyl)-4-(3-morpholin-4-ylazetidin-1-yl)butyl]-N-methylindane-4-carboxamide;

3-Cyano-N-{(2S)-2-(3,4-dichlorophenyl)-4-[3-(1-oxidothiomorpholin-4-yl)azetidin-1-yl]butyl}-N-methyl-1-naphthamide;

3-Cyano-N-{2-(4-cyanophenyl)-4-[3-(1-oxidothiomorpholin-4-yl)azetidin-1-yl]butyl}-N-methyl-1-naphthamide;

3,5-Dichloro-N-{(2S)-2-(3,4-dichlorophenyl)-4-[3-(1-oxidothiomorpholin-4-yl)azetidin-1-yl]butyl}-N-methylbenzamide;

N-[(2S)-2-(3,4-Dichlorophenyl)-4-(3-oxidothiomorpholin-4-ylazetidin-1-yl)butyl]-N-methyl-3,5-bis(trifluoromethyl)benzamide;

3-Cyano-N-{(2S)-2-(3,4-dichlorophenyl)-4-[3-(1-oxidothiomorpholin-4-yl)azetidin-1-yl]butyl}-N-methyl-5,6,7,8-tetrahydronaphthalene-1-carboxamide;

3-Cyano-N-{2-(4-fluorophenyl)-4-[3-(1-oxidothiomorpholin-4-yl)azetidin-1-yl]butyl}-N-methyl-1-naphthamide;

3-cyano-N-{2-(4-fluorophenyl)-4-[3-(1-oxidothiomorpholin-4-yl)azetidin-1-yl]butyl}-N-methyl-5,6,7,8-tetrahydronaphthalene-1-carboxamide;

N-{2-(4-Fluorophenyl)-4-[3-(1-oxidothiomorpholin-4-yl)azetidin-1-yl]butyl}-N-methyl-3,5-bis(trifluoromethyl)benzamide;

3-Cyano-N-{(2S)-2-(3,4-dichlorophenyl)-4-[3-(4-oxopiperidin-1-yl)azetidin-1-yl]butyl}-N-methyl-1-naphthamide;

N-{2-(4-fluorophenyl)-4-[3-(4-oxopiperidin-1-yl)azetidin-1-yl]butyl}-N-methyl-3,5-bis(trifluoromethyl)benzamide;

3-Cyano-N-{(2S)-2-(3,4-dichlorophenyl)-4-[3-(4-fluoropiperidin-1-yl)azetidin-1-yl]butyl}-N-methyl-1-naphthamide;

3-Cyano-N-{2-(4-fluorophenyl)-4-[3-(4-fluoropiperidin-1-yl)azetidin-1-yl]butyl}-N-methyl-5,6,7,8-tetrahydronaphthalene-1-carboxamide;

3-Cyano-N-{(2S)-2-(3,4-dichlorophenyl)-4-[3-(4-methylpiperazin-1-yl)azetidin-1-yl]butyl}-N-methyl-1-naphthamide;

N-[(2S)-4-[3-(4-Acetylpiperazin-1-yl)azetidin-1-yl]-2-(3,4-dichlorophenyl)butyl]-3-cyano-N-methyl-1-naphthamide;

3-Cyano-N-[(2S)-4-[3-(4-cyanopiperidin-1-yl)azetidin-1-yl]-2-(3,4-dichlorophenyl)butyl]-N-methyl-1-naphthamide;

or an enantiomer thereof or any salt thereof.

The present invention relates to the use of compounds of formula I as defined above as well as to salts thereof. Salts for use in pharmaceutical compositions will be pharmaceutically acceptable salts, but other salts may be useful in the production of the compounds of formula I.

The compounds of the present invention are capable of forming salts with various inorganic and organic acids and such salts are also within the scope of this invention.

Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, palmoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Non-toxic physiologically acceptable salts are preferred, although other salts are also useful, such as in isolating or purifying the product.

Pharmaceutically acceptable salts may be prepared from the corresponding acid in conventional manner. Non-pharmaceutically-acceptable salts may be useful as intermediates and as such are another aspect of the present invention.

Acid addition salts may also be in the form of polymeric salts such as polymeric sulfonates.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compounds of formula I have one or more chiral centres, and it is to be understood that the invention encompasses all optical isomers, enantiomers and diastereomers. The compounds according to formula (I) can be in the form of the single stereoisomers, i.e. the single enantiomer (the R-enantiomer or the S-enantiomer) and/or diastereomers. The compounds according to formula (I) can also be in the form of a racemic mixture, i.e. an equimolar mixture of enantiomers.

It is to be understood that the present invention also relates to any and all tautomeric forms of the compounds of formula I.

Some compounds can exist as a mixture of conformational isomers. The compounds of this invention comprise both mixtures of, and individual, conformational isomers.

Listed below are definitions of various terms used in the specification and claims to describe the present invention.

For the avoidance of doubt it is to be understood that where in this specification a group is qualified by 'hereinbefore defined' or 'defined hereinbefore' the said group encompasses the first occurring and broadest definition as well as each and all of the preferred definitions of that group.

Unless stated otherwise, the term "alkyl" includes straight as well as branched chain $C_{1-4}$ alkyl groups, for example methyl, ethyl, n-propyl, i-propyl, n-butyl, i-butyl, s-butyl or t-butyl. One or more of the hydrogen atoms of the alkyl group may be substituted for a fluorine atom, such as in difluoromethyl or trifluoromethyl.

As used herein, $C_3$-$C_4$ cycloalkyl is a cyclic alkyl such as cyclopropyl or cyclobutyl. The cycloalkyl may also be unsaturated. One or more of the hydrogen atoms of the cycloalkyl group may be substituted for a fluorine atom.

As used herein, $C_2$-$C_4$ alkenyl is a straight or branched alkenyl group, for example vinyl. One or more of the hydrogen atoms of the alkenyl group may be substituted for a fluorine atom.

As used herein, $C_2$-$C_4$ alkynyl is a straight or branched alkynyl group, for example ethynyl. One or more of the hydrogen atoms of the alkynyl group may be substituted for a fluorine atom.

As used herein, $C_1$-$C_4$ hydroxyalkyl is a hydroxyalkyl group comprising 1-4 carbon atoms and a hydroxyl group. One or more of the hydrogen atoms of the hydroxyalkyl group may be substituted for a fluorine atom.

The term "alkoxy" as used herein, unless stated otherwise includes $C_1$-$C_4$ alkoxy groups, for example methoxy, ethoxy, n-propoxy, i-propoxy, n-butoxy, i-butoxy, s-butoxy or t-butoxy. One or more of the hydrogen atoms of the alkoxy group may be substituted for a fluorine atom.

The term "alkylthio" as used herein, unless stated otherwise includes $C_1$-$C_4$ alkylthio groups, for example methylthio, ethylthio, n-propylthio, i-propylthio, n-butylthio, i-butylthio, s-butylthio or t-butylthio. One or more of the hydrogen atoms of the alkylthio group may be substituted for a fluorine atom.

In this specification, unless stated otherwise, the term "halogen" includes chloro, bromo, fluoro and iodo.

In this specification, unless stated otherwise, the term "alkyl sulfonyl" includes $C_1$-$C_4$ alkyl sulfonyl groups, for example methylsulfonyl, ethylsulfonyl, n-propylsulfonyl, i-propylsulfonyl, n-butylsulfonyl, i-butylsulfonyl, s-butylsulfonyl or t-butylsulfonyl.

In this specification, unless stated otherwise, the term "alkylsulfinyl" includes $C_1$-$C_4$ alkyl sulfinyl groups, for example methylsulfinyl, ethylsulfinyl, n-propylsulfinyl, i-propylsulfinyl, n-butylsulfinyl, i-butylsulfinyl, s-butylsulfinyl or t-butylsulfinyl.

In this specification, unless stated otherwise, the term "acyl" includes $C_1$-$C_4$ acyl groups, for example formyl, acetyl, propionyl, butyryl and isobutyryl.

As used herein, the term "free base" means the compound in its neutral form, i.e. when the compound is not present as a salt.

Pharmaceutical Formulations

According to one aspect of the present invention there is provided a pharmaceutical formulation comprising a compound of formula I, as a single enantiomer, a racemate or a mixture thereof as a free base or pharmaceutically acceptable salts thereof, for use in prevention and/or treatment of respiratory, cardiovascular, neuro, pain, oncology, imflammatory and/or gastrointestinal disorders.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, pellets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Medical and Pharmaceutical Use

The present invention provides a method of treating or preventing a disease condition wherein antagonism of tachykinins acting at the $NK_1$ and $NK_2$ receptors is beneficial which comprises administering to a subject an effective amount of a compound of the formula (I) or a pharmaceutically-acceptable salt thereof. The present invention also provides the use of a compound of the formula (I) or a pharmaceutically acceptable salt thereof in the preparation of a medicament for use in a disease condition wherein antagonism of tachykinins acting at the $NK_1$ and $NK_2$ receptors is beneficial.

The compounds of formula (I) or pharmaceutically acceptable salts or solvates thereof may be used in the manufacture of a medicament for use in the prevention or treatment of respiratory, cardiovascular, neuro, pain, oncology and/or gastrointestinal disorders.

Examples of such disorders are asthma, allergic rhinitis, pulmonary diseases, cough, cold, inflammation, chronic obstructive pulmonary disease, airway reactivity, urticaria, hypertension, rheumatoid arthritis, edema, angiogenesis, pain, migraine, tension headache, psychoses, depression, anxiety, Alzheimer's disease, schizophrenia, Huntington's disease, bladder hypermotility, urinary incontinence, eating disorder, manic depression, substance dependence, movement disorder, cognitive disorder, obesity, stress disorders, micturition disorders, mania, hypomania and aggression, bipolar disorder, cancer, carcinoma, fibromyalgia, non cardiac chest pain, gastrointestinal hypermotility, gastric asthma, Crohn's disease, gastric emptying disorders, ulcerative colitis, irritable bowel syndrome (IBS), inflammatory bowel disease (IBD), emesis, gastric asthma, gastric motility disorders or gastro-esophageal reflux disease (GERD).

Pharmacology

Transfection and Culturing of Cells used in FLIPR and Binding Assays

Chinese Hamster Ovary (CHO) K1 cells (obtained from ATCC) were stably transfected with the human $NK_2$ receptor ($hNK_2R$ cDNA in pRc/CMV, Invitrogen) or the human $NK_3$ receptor ($hNK_3R$ in pcDNA 3.1/Hygro (+)/IRES/CD8, Invitrogen vector modified at AstraZeneca EST-Bio UK, Alderley Park). The cells were transfected with the cationic lipid reagent LIPOFECTAMINE™ (Invitrogen) and selection was performed with Geneticin (G418, Invitrogen) at 1 mg/ml for the $hNK_2R$ transfected cells and with Hygromycin (Invitrogen) at 500 μg/ml for the $hNK_3R$ transfected cells. Single cell clones were collected by aid of Fluorescence Activated Cell Sorter (FACS), tested for functionality in a FLIPR assay (see below), expanded in culture and cryopreserved for future use. CHO cells stably transfected with human $NK_1$ receptors originates from AstraZeneca R&D, Wilmington USA. Human $NK_1$ receptor cDNA (obtained from RNA-PCR from lung tissue) was subcloned into pRcCMV (Invitrogen). Transfection was performed by Calcium Phosphate and selection with 1 mg/ml G418.

The CHO cells stably transfected with $hNK_1R$, $hNK_2R$ and $hNK_3R$ were cultured in a humidified incubator under 5% $CO_2$, in Nut Mix F12 (HAM) with Glutamax I, 10% Foetal Bovine Serum (FBS), 1% Penicillin/Streptomycin (PEST) supplemented with 200 μg/ml Geneticin for the $hNK_1R$ and $hNK_2R$ expressing cells and 500 μg/ml Hygromycin for the $hNK_3R$ expressing cells. The cells were grown in T175 flasks and routinely passaged when 70-80% confluent for up to 20-25 passages.

Assessing the Activity of Selected Test Compounds to Inhibit Human $NK_1/NK_2/NK_3$ Receptor Activation (FLIPR Assay)

The activity of a compound of the invention to inhibit $NK_1/NK_2/NK_3$ receptor activation measured as $NK_1/NK_2/NK_3$ receptor mediated increase in intracellular $Ca^{2+}$ was assessed by the following procedure:

CHO cells stably transfected with human $NK_1$, $NK_2$ or $NK_3$ receptors were plated in black walled/clear bottomed 96-well plates (Costar 3904) at $3.5 \times 10^4$ cells per well and grown for approximately 24 h in normal growth media in a 37° C. $CO_2$-incubator.

Before the FLIPR assay the cells of each 96-well plate were loaded with the $Ca^{2+}$ sensitive dye Fluo-3 (TEFLABS 0116) at 4 μM in a loading media consisting of Nut Mix F12 (HAM) with Glutamax I, 22 mM HEPES, 2.5 mM Probenicid (Sigma P-8761) and 0.04% Pluronic F-127 (Sigma P-2443) for 1 h kept dark in a 37° C. $CO_2$-incubator. The cells were then washed three times in assay buffer (Hanks balanced salt solution (HBSS) containing 20 mM HEPES, 2.5 mM Probenicid and 0.1% BSA) using a multi-channel pipette leaving them in 150 μl at the end of the last wash. Serial dilutions of a test compound in assay buffer (final DMSO concentration kept below 1%) were automatically pipetted by FLIPR (Fluorometric Imaging Plate Reader) into each test well and the fluorescence intensity was recorded (excitation 488 nm and emission 530 nm) by the FLIPR CCD camera for a 2 min pre-incubation period. 50 μl of the Substance P ($NK_1$ specific), NKA ($NK_2$ specific), or Pro-7-NKB ($NK_3$ specific) agonist solution (final concentration equivalent to an approximate $EC_{60}$ concentration) was then added by FLIPR into each well already containing 200 μl assay buffer (containing the test compound or vehicle) and the fluorescence was continuously monitored for another 2 min. The response was measured as the peak relative fluorescence after agonist addition and $IC_{50}$s were calculated from ten-point concentration-response curves for each compound. The $IC_{50}$s were then converted to $pK_B$ values with the following formula:

$$K_B = IC_{50}/1 + (EC_{60} \text{ conc. of agonist used in assay}/EC_{50} \text{ agonist})$$

$$pK_B = -\log K_B$$

Determining the Dissociation Constant (Ki) of Compounds for Human $NK_1/NK_2/NK_3$ Receptors (Binding Assay)

Membranes were prepared from CHO cells stably transfected with human $NK_1$, $NK_2$ or $NK_3$ receptors according to the following method.

Cells were detached with Accutase® solution, harvested in PBS containing 5% FBS by centrifugation, washed twice in PBS and resuspended to a concentration of $1 \times 10^8$ cells/ml in Tris-HCl 50 mM, KCl 300 mM, EDTA-$N_2$ 10 mM pH 7.4 (4° C.). Cell suspensions were homogenized with an UltraTurrax 30 s 12.000 rpm. The homogenates were centrifuged at 38.000×g (4° C.) and the pellet resuspended in Tris-HCl 50 mM pH 7.4. The homogenization was repeated once and the homogenates were incubated on ice for 45 min. The homogenates were again centrifuged as described above and resuspended in Tris-HCl 50 mM pH 7.4. This centrifugation step was repeated 3 times in total. After the last centrifugation step the pellet was resuspended in Tris-HCl 50 mM and homogenized with Dual Potter, 10 strokes to a homogenous solution, an aliquot was removed for protein determination. Membranes were aliquoted and frozen at −80° C. until use.

The radioligand binding assay is performed at room temperature in 96-well microtiter plates (No-binding Surface Plates, Corning 3600) with a final assay volume of 200 μl/well in incubation buffer (50 mM Tris buffer (pH 7.4 RT) containing 0.1% BSA, 40 mg/L Bacitracin, complete EDTA-free protease inhibitor cocktail tablets 20 pills/L (Roche) and 3 mM $MnCl_2$). Competition binding curves were done by adding increasing amounts of the test compound. Test compounds were dissolved and serially diluted in DMSO, final DMSO concentration 1.5% in the assay. 50 μl Non labelled ZD 6021 (a non selective NK-antagonist, 10 μM final conc) was added for measurement of non-specific binding. For total binding, 50 μl of 1.5% DMSO (final conc) in incubation buffer was used.[$^3$H-Sar,Met($O_2$)-Substance P] (4 nM final conc) was used in binding experiments on $hNK_1r$. [$^3$H-SR48968] (3 nM final conc.) for $hNK_2r$ and [$^3$H-SR142801] (3 nM final conc) for binding experiments on $hNK_3r$. 50 μl radioligand, 3 μl test compound diluted in DMSO and 47 μl incubation buffer were mixed with 5-10 μg cell membranes in 100 μl incubation buffer and incubated for 30 min at room temperature on a microplate shaker.

The membranes were then collected by rapid filtration on Filtermat B(Wallac), presoaked in 0.1% BSA and 0.3% Polyethyleneimine (Sigma P-3143), using a Micro 96 Harvester (Skatron Instruments, Norway). Filters were washed by the harvester with ice-cold wash buffer (50 mM Tris-HCl, pH 7.4 at 4° C., containing 3 mM $MnCl_2$) and dried at 50° C. for 30-60 min. Meltilex scintillator sheets were melted on to filters using a Microsealer (Wallac, Finland) and the filters were counted in a β-Liquid Scintillation Counter (1450 Microbeta, Wallac, Finland).

The $K_i$ value for the unlabeled ligand was calculated using the Cheng-Prusoff equation (Biochem. Pharmacol. 22:3099-3108, 1973): where L is the concentration of the radioactive ligand used and $K_d$ is the affinity of the radioactive ligand for the receptor, determined by saturation binding.

Data was fitted to a four-parameter equation using Excel Fit.

$$K_i = IC_{50}/(1+(L/K_d))$$

Results

In general, the compounds of the invention, which were tested, demonstrated statistically significant antagonistic activity at the $NK_1$ receptor within the interval 7-9 for the $pK_B$. For the $NK_2$ receptor the interval for the $pK_B$ was 7-9. In general, the antagonistic activity at the $NK_3$ receptor was less than 7.5 for the $pK_B$.

In general, the compounds of the invention, which were tested, demonstrated statistically significant CYP3A4 inhibition at a low level. The $IC_{50}$ values tested according to Bapiro et al; Drug Metab. Dispos. 29, 30-35 (2001) were generally greater than 2 μM.

Thus, the tested compounds according to the invention have been shown to be selective and dual $NK_1/NK_2$ receptor antagonists as well as showing low levels of CYP3A4 inhibition.

Biological Evaluation

Gerbil Foot Tap (NK1 Specific Test Model)

Male Mongolian gerbils (60-80 g) are purchased from Charles River, Germany. On arrival, they are housed in groups of ten, with food and water ad libitium in temperature and humidity-controlled holding rooms. The animals are allowed at least 7 days to acclimatize to the housing conditions before experiments. Each animal is used only once and killed immediately after the experiment by heart punctuation or a lethal overdose of penthobarbital sodium.

Gerbils are anaesthetized with isoflurane. Potential CNS-permeable NK1 receptor antagonists are administered intraperitoneally, intravenously or subcutaneously. The compounds are given at various time points (typically 30-120 minutes) prior to stimulation with agonist.

The gerbils are lightly anaesthetized using isofluorane and a small incision is made in the skin over bregma. 10 pmol of ASMSP, a selective NK1 receptor agonist, is administered icv in a volume of 5 μl using a Hamilton syringe with a needle 4 mm long. The wound is clamped shut and the animal is placed in a small plastic cage and allowed to wake up. The cage is placed on a piece of plastic tubing fined with water and connected to a computer via a pressure transducer. The number of hind feet taps is recorded.

Fecal Pellet Output (NK2 Specific Test Model)

The in vivo effect (NK2) of the compounds of formula I can be determined by measuring NK2 receptor agonist-induced fecal pellet output using gerbil as described in e.g. The Journal of Pharmacology and Experimental Therapeutics (2001) 559-564.

Methods of Preparation

In another aspect the present invention provides a process for preparing a compound of the formula (I) or salts thereof which process comprises:

a) reacting a compound of the formula (III) with a compound of the formula (IV):

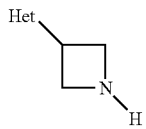
(III)

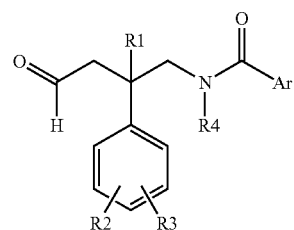
(IV)

wherein R1-R4, Het, and Ar are as hereinbefore defined; and the conditions are such that reductive alkylation of the compounds of the formula (III) forms an N—C bond between the nitrogen atom of the azetidine group of the compounds of formula (III) and the carbon atom of the aldehyde group of the compounds of formula (IV); or b) reacting a compound of the formula (III) with a compound of the formula (V):

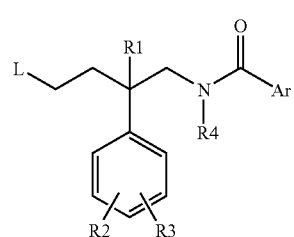
(V)

wherein R1-R4, Het, and Ar are as hereinbefore defined; and L is a group such that alkylation of the compounds of the formula (III) forms an N—C bond between the nitrogen atom of the azetidine group of the compounds of formula (III) and the carbon atom of the compounds of formula (V) that is adjacent to the L group; or c) reacting a compound of the formula (VI) with a compound of the formula (VII):

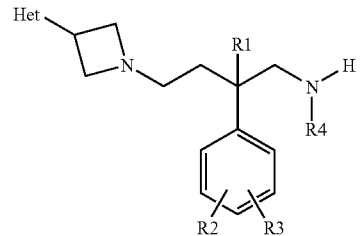
(VI)

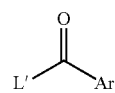
(VII)

wherein R1-R4, Het and Ar are as hereinbefore defined; and L' is a leaving group;
wherein any other functional group is protected, if necessary, and:
i) removing any protecting groups;
ii) optionally oxidizing any oxidizeable atoms;
iii) optionally forming a pharmaceutically acceptable salt.

Protecting groups may in general be chosen from any of the groups described in the literature or known to the skilled chemist as appropriate for the protection of the group in question, and may be introduced and removed by conventional methods; see for example Protecting Groups in Organic Chemistry; Theodora W. Greene. Methods of removal are chosen so as to effect removal of the protecting group with minimum disturbance of groups elsewhere in the molecule.

It will also be appreciated that certain of the various optional substituents in the compounds of the formula (I) may be introduced by standard aromatic substitution reactions or generated by conventional functional group modifications either prior to or immediately following the processes described hereinabove. The reagents and reaction conditions for such procedures are well known in the chemical art.

The compounds of the formulae (III) and (IV) are reacted under conditions of reductive alkylation. The reaction is typically performed at a non-extreme temperature, for example 0-100° C., in a substantially inert solvent for example dichloromethane. Typical reducing agents include borohydrides such as sodium cyanoborohydride.

The compounds of the formulae (III) and (V) are reacted under conditions of alkylation. Typically in the compounds of the formula (V) L is a leaving group such as halogen or alkylsulfonyloxy. The reaction is typically performed at an elevated temperature, for example 30-130° C., in a substantially inert solvent for example DMF.

The compounds of the formula (III) are known or may be prepared in conventional manner. The compounds of the formula (IV) may be prepared, for example, by reacting a compound of the formula (VII) with a compound of the formula (VIII):

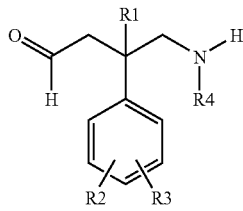

(VIII)

wherein R1-R4 are as hereinbefore defined under conventional acylation conditions.

The compounds of the formula (V) may be prepared, for example, by reacting a compound of the formula (VII) with a compound of the formula (IX):

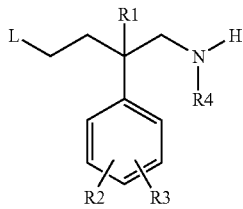

(IX)

wherein R1-R4 and L are as hereinbefore defined under conventional acylation conditions.

The compounds of the formulae (VI) and (VII) may be reacted under conventional acylation conditions wherein

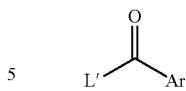

is an acid or an activated acid derivative. Such activated acid derivatives are well known in the literature. They may be formed in situ from the acid or they may be prepared, isolated and subsequently reacted. Typically L' is chloro thereby forming the acid chloride. Typically the acylation reaction is performed in the presence of a non-nucleophilic base, for example N,N-diisopropylethylamine, in a substantially inert solvent such as dichloromethane at a non-extreme temperature.

The compounds of the formula (VIII) and (IX) are known or may be prepared in conventional manner.

Certain compounds of the formulae (III), (IV), (V), (VI), (VII), (VIII) and (IX) are novel and form part of the present invention.

Thus, another aspect of the invention is the intermediates
[(2S)-2-(3,4-dichlorophenyl)-4-(3-thiomorpholin-4-ylazetidin-1-yl)butyl]methylamine;
[(2S)-2-(3,4-dichlorophenyl)-4-[3-(1-oxidothiomorpholin-4-yl)azetidin-1-yl]butyl]methylamine;
[2-(4-fluorophenyl)-4-(3-thiomorpholin-4-ylazetidin-1-yl)butyl]methylamine;
[(2S)-2-(4-fluorophenyl)-4-(3-morpholin-4-ylazetidin-1-yl)butyl]methylamine;
1-{1-[3-(4-fluorophenyl)-4-(methylamino)butyl]azetidin-3-yl}piperidin-4-ol;
[4-[3-(1,4-dioxa-8-azaspiro[4.5]dec-8-yl)azetidin-1-yl]-2-(4-fluorophenyl)butyl]methylamine;
{(2S)-2-(3,4-dichlorophenyl)-4-[3-(4-fluoropiperidin-1-yl)azetidin-1-yl]butyl}methylamine;
1-{1-[(3S)-3-(3,4-dichlorophenyl)-4-(methylamino)butyl]azetidin-3-yl}piperidin-4-ol;
1-[(3S)-4-[(3-cyano-1-naphthoyl)(methyl)amino]-3-(3,4-dichlorophenyl)butyl]azetidin-3-yl;
3-cyano-N-[2-(4-fluorophenyl)-4-oxobutyl]-N-methyl-1-naphthamide;
3-cyano-N-[2-(4-cyanophenyl)-4-oxobutyl]-N-methyl-1-naphthamide;
3-cyano-N-[(2S)-2-(4-fluorophenyl)-4-oxobutyl]-N-methyl-5,6,7,8-tetrahydronaphthalene-1-carboxamide;
3,5-dichloro-N-[(2S)-2-(4-fluorophenyl)-4-oxobutyl]-N-methylbenzamide;
3-cyano-N-ethyl-N-[(2S)-2-(4-fluorophenyl)-4-oxobutyl]-5,6,7,8-tetrahydronaphthalene-1-carboxamide;
3-cyano-N-[(2S)-2-(4-fluorophenyl)-4-oxobutyl]-N-methyl-1-naphthamide;
3,5-dibromo-N-[(2S)-2-(4-fluorophenyl)-4-oxobutyl]-N-methylbenzamide;
3-bromo-N-[(2S)-2-(4-fluorophenyl)-4-oxobutyl]-5-iodo-N-methylbenzamide;
3-cyano-N-[2-(4-fluoro-2-methylphenyl)-4-oxobutyl]-N-methyl-5,6,7,8-tetrahydronaphthalene-1-carboxamide;
6-cyano-N-[(2S)-2-(4-fluorophenyl)-4-oxobutyl]-N-methylindane-4-carboxamide;
3-fluoro-N-[(2S)-2-(4-fluorophenyl)-4-oxobutyl]-N-methyl-5,6,7,8-tetrahydronaphthalene-1-carboxamide;
or an enantiomer thereof or any salt thereof.

EXAMPLES

It should be emphasised that the compounds of the present invention most often show highly complex NMR spectra due to the existence of conformational isomers. This is believed to be a result from slow rotation about the amide and/or aryl bond. The following abbreviations are used in the presentation of the NMR data of the compounds: s-singlet; d-doublet; t-triplet; qt-quartet; qn-quintet; m-multiplet; b-broad; cm-complex multiplet, which may include broad peaks.

The following examples will describe, but not limit, the invention.

The following abbreviations are used in the experimental: DCC (1,3-dicyclohexylcarbodiimide), DIPEA (N,N-diisopropylethylamine), DMF (N,N-dimethylformamide), TBTU (N,N,N',N'-tetramethyl-O-(benzotriazol-1-yl)uronium tetrafluoroborate), NMO (4-methylmorpholine N-oxide) and THF (tetrahydrofuran).

Example 1

3,5-Dichloro-N-[(2S)-2-(3,4-dichlorophenyl)-4-(3-thiomorpholin-4-ylazetidin-1-yl)butyl]-N-methyl-benzamide acetate

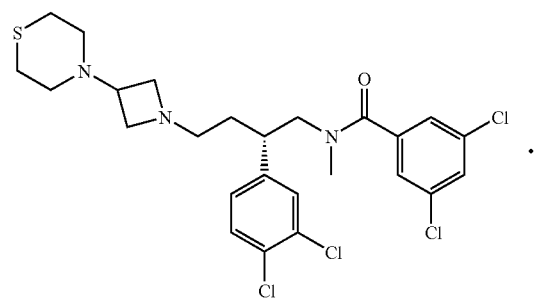

[(2S)-2-(3,4-Dichlorophenyl)-4-(3-thiomorpholin-4-ylazetidin-1-yl)butyl]methylamine hydrochloride (see Method 1; 89 mg, 0.21 mmol) was dissolved in DMF (2 mL) and to the resultant solution were added 3,5-dichlorobenzoic acid (44 mg, 0.23 mmol), TBTU (80 mg, 0.25 mmol) and DIPEA (108 mg, 0.84 mmol) in the given order. The solution was stirred at room temperature for 1.5 h, diluted with water and then neutralized by the addition of NaHCO₃. The mixture was extracted twice with ethyl acetate and the combined organic solutions were dried over MgSO₄. The solvent was removed by evaporation to yield 79 mg of crude product. The product was purified by reversed phase chromatography using a mixture of acetonitrile and 0.1 M ammonium acetate aq. There was obtained 43 mg (37%) of the title compound as a white solid. $^1$H NMR (500 MHz, CD₃CN): 1.3-1.8 (cm, 3H), 2.0-4.6 (cm, 23H), 6.8-7.7 (cm, 5H), 8.0 (d, 1H); LCMS: m/z 560 (M+1)$^+$.

Example 2

3,5-Dibromo-N-[(2S)-2-(4-fluorophenyl)-4-(3-morpholin-4-ylazetidin-1-yl)butyl]-N-methylbenzamide dihydrochloride

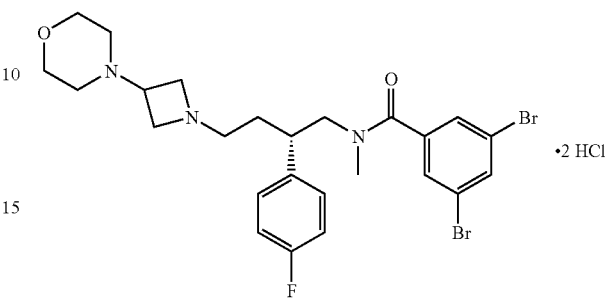

[(2S)-2-(Fluorophenyl)-4-(3-morpholin-4-ylazetidin-1-yl)butyl]methylamine dihydrochloride (see Method 4; 292 mg, 0.68 mmol), 3,5-dibromobenzoic acid (215 mg, 0.77 mmol) and DIPEA (350 mg, 2.71 mmol) were dissolved in DMF (20 mL) and to the resultant solution was added TBTU (250 mg, 0.78 mmol) at 0° C. The mixture was stirred at RT for 2 h and then the solvent was removed by evaporation. The residue was diluted with ethyl acetate and then washed thrice with an aqueous solution of NaHCO₃. The organic solution was combined with another preparation of the title compound (as free base) being prepared by a similar method (68 mg). The combined organic solutions were then dried over MgSO₄ and the solvent was removed by evaporation to yield 344 mg. The product was purified by reversed phase chromatography using a mixture of acetonitrile and 0.1 M ammonium acetate aq. The collected fractions were freeze-dried and the residue was then dissolved in a mixture of water and acetonitrile. The solution was acidified with hydrochloric acid (2 M) and again freeze-dried. There was obtained 267 mg (55%) of the title compound as a grey solid. $^1$H NMR (500 MHz, CD₃OD): 1.8-2.1 (cm, 2H), 2.7-4.8 (cm, 21H), 6.9-7.8 (cm, 7H); LCMS: m/z 584 (M+1)$^+$.

Examples 3-18

The following compounds, which are tabulated below, were synthesized in an analogous way to that of Example 1 and Example 2 using the appropriate amine and acid intermediates (see below): N-[(2S)-2-(3,4-Dichlorophenyl)-4-(3-thiomorpholin-4-ylazetidin-1-yl)butyl]-3,5-difluoro-N-methylbenzamide acetate (Ex. 3), N-[(2S)-2-(3,4-Dichlorophenyl)-4-(3-thiomorpholin-4-ylazetidin-1-yl)butyl]-N-methyl-3,5-bis(trifluoromethyl)benzamide acetate (Ex 4), 5-Cyano-N-[(2S)-2-(3,4-dichlorophenyl)-4-(3-thiomorpholin-4-ylazetidin-1-yl)butyl]-N-methyl-1-benzothiophene-7-carboxamide acetate (Ex 5), 3-Cyano-N-[(2S)-2-(3,4-dichlorophenyl)-4-(3-thiomorpholin-4-ylazetidin-1-yl)butyl]-N-methylbenzamide acetate (Ex 6), 3-Cyano-N-[(2S)-2-(3,4-dichlorophenyl)-4-(3-thiomorpholin-4-ylazetidin-1-yl)butyl]-N-methyl-5,6,7,8-tetrahydronaphthalene-1-carboxamide acetate (Ex 7), 2-Cyano-N-[(2S)-2-(3,4-dichlorophenyl)-4-(3-thiomorpholin-4-ylazetidin-1-yl)butyl]-N-methylquinoline-4-carboxamide acetate (Ex 8), 3-Cyano-N-[2-(4-fluorophenyl)-4-(3-thiomorpholin-4-ylazetidin-1-yl)butyl]-N-methyl-5,6,7,8-tetrahydronaphthalene-1-carboxamide diacetate (Ex 9), N-[2-(4-Fluorophenyl)-4-(3-thiomorpholin-4-ylazetidin-1-yl)

butyl]-N-methyl-3,5-bis(trifluoromethyl)benzamide diacetate (Ex 10), 7-Chloro-N-[(2S)-2-(3,4-dichlorophenyl)-4-(3-thiomorpholin-4-ylazetidin-1-yl)butyl]-N-methyl-2,3-dihydro-1,4-benzodioxine-5-carboxamide acetate (Ex 11), N-{(2S)-2-(3,4-Dichlorophenyl)-4-[3-(1-oxidothiomorpholin-4-yl)azetidin-1-yl]butyl}-2-methoxy-N-methylquinoline-4-carboxamide (Ex 12), 3-Fluoro-N-[(2S)-2-(4-fluorophenyl)-4-(3-morpholin-4-ylazetidin-1-yl)butyl]-N-methyl-5-(trifluoromethyl)benzamide (Ex 13), 3-Cyano-N-{2-(4-fluorophenyl)-4-[3-(4-hydroxypiperidin-1-yl)azetidin-1-yl]butyl}-N-methyl-5,6,7,8-tetrahydronaphthalene-1-carboxamide acetate (Ex 14), N-[4-[3-(1,4-Dioxa-8-azaspiro[4.5]dec-8-yl)azetidin-1-yl]-2-(4-fluorophenyl)butyl]-N-methyl-3,5-bis(trifluoromethyl)benzamide (Ex 15), N-{(2S)-2-(3,4-Dichlorophenyl)-4-[3-(4-fluoropiperidin-1-yl)azetidin-1-yl]butyl}-N-methyl-3,5-bis(trifluoromethyl)benzamide (Ex 16), N-{(2S)-2-(3,4-Dichlorophenyl)-4-[3-(4-hydroxypiperidin-1-yl)azetidin-1-yl]butyl}-N-methyl-3,5-bis(trifluoromethyl)benzamide diacetate (Ex 17).

The amine and acid intermediates used in the examples below are often commercially available and if not the syntheses thereof are described in the following referred Methods (Meth) or in the following cited documents: Ex 3 (see Meth 1), Ex 4 (see Meth 1), Ex 5 (see Meth 1 and Meth 9), Ex 6 (see Meth 1), Ex 7 (see Meth 1 and WO 00/34243), Ex 8 (see Meth 1 and J Prakt Chem; 1902; 264), Ex 9 (see Meth 3 and WO 00/34243), Ex 10 (see Meth 3), Ex 11 (see Meth 1 and Meth 10), Ex 12 (see Meth 2 and J Med Chem; 1992; 4893), Ex 13 (see Meth 4), Ex 14 (Meth 5 and WO 00/34243), Ex 15 (see Meth 6), Ex 16 (see Meth 7) and Ex 17 (see Meth 8).

| Ex | Compound | $^1$H NMR | LCMS | Yield |
|---|---|---|---|---|
| 3 | 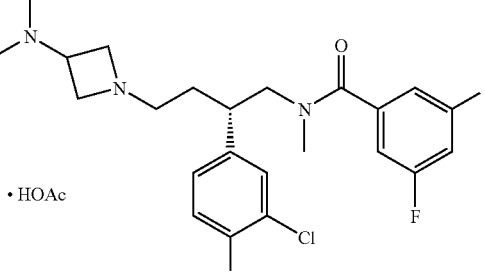 | (300 MHz, CD$_3$OD): 1.6-2.0 (cm, 3H), 2.0 (s, 3H), 2.4-4.0 (cm, 20H), 6.4-7.6 (cm, 6H) | 528 (M + 1)$^+$ | 75% |
| 4 | 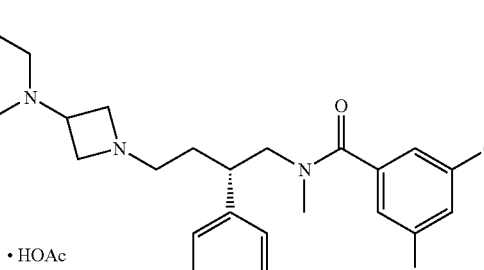 | (300 MHz, CD$_3$OD): 1.5-2.4 (cm, 3H), 2.0 (s, 3H), 2.4-4.0 (cm, 20H), 6.9-7.7 (cm, 5H), 8.0 (s, 1H) | 628 (M + 1)$^+$ | 52% |
| 5 | 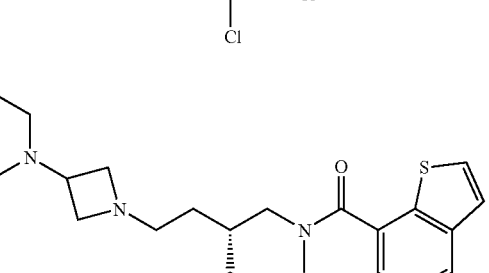 | (300 MHz, CD$_3$OD): 1.4-2.2 (cm, 3H), 2.0 (s, 3H), 2.4-4.0 (cm, 20H), 6.7-7.8 (cm, 4H), 7.5 (d, 1H), 7.8 (d, 1H), 8.3 (s, 1H) | 573 (M + 1)$^+$ | 56% |

-continued
| Ex | Compound | $^1$H NMR | LCMS | Yield |
|---|---|---|---|---|
| 6 | 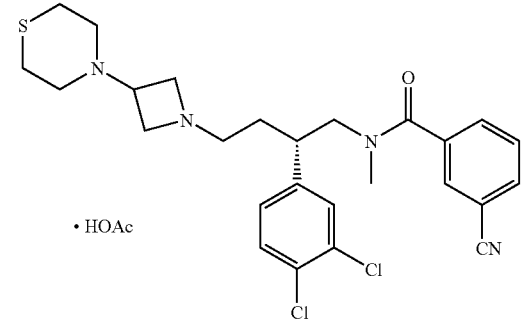<br>• HOAc | (300 MHz, CD$_3$OD): 1.4-2.4 (cm, 3H), 2.0 (s, 3H), 2.4-3.8 (cm, 20H), 6.9-7.6 (cm, 6H), 7.8 (d, 1H) | 517 (M + 1)$^+$ | 79% |
| 7 | 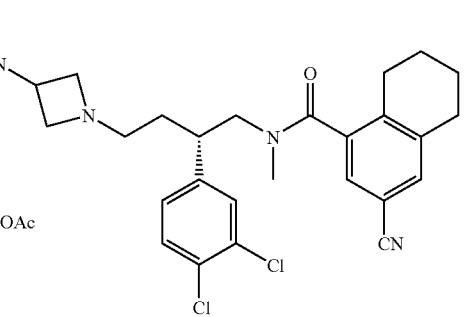<br>• HOAc | (400 MHz, CDCl$_3$): 1.4-4.4 (cm, 34H), 6.7-7.4 (cm, 4H), 7.4 (d, 1H) | 571 (M + 1)$^+$ | 36% |
| 8 | 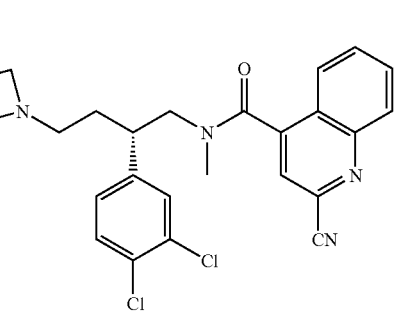<br>• HOAc | (400 MHz, CDCl$_3$): 1.4-2.0 (cm, 3H), 2.0 (s, 3H), 2.2-4.4 (cm, 20H), 6.4-7.9 (cm, 7H), 8.2 (d, 1H) | 568 (M + 1)$^+$ | 30% |
| 9 | 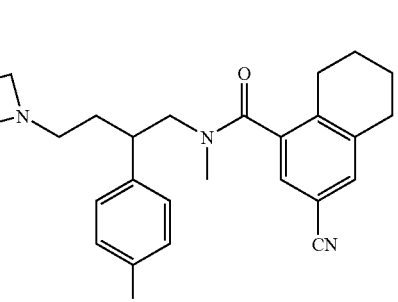<br>• 2 HOAc | (400 MHz, CDCl$_3$): 1.4-2.0 (cm, 6H), 2.0 (s, 6H), 2.2-4.0 (cm, 25H), 6.74-7.4 (cm, 6H) | 521 (M + 1)$^+$ | 19% |

-continued
| Ex | Compound | ¹H NMR | LCMS | Yield |
|---|---|---|---|---|
| 10 | 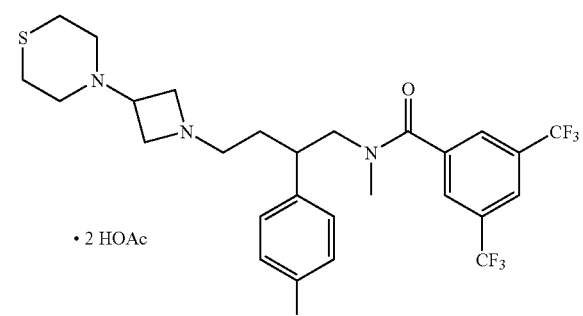<br>• 2 HOAc | (400 MHz, CDCl₃): 1.4-2.0 (cm, 2H), 2.0 (s, 6H), 2.2-3.8 (cm, 21H), 6.8-7.6 (cm, 6H), 7.8 (s, 1H) | 578 (M + 1)⁺ | 17% |
| 11 | 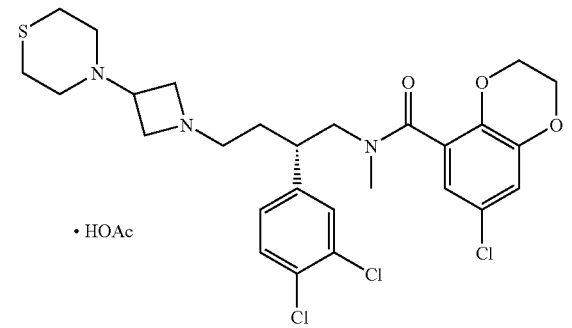<br>• HOAc | (400 MHz, CD₃OD): 1.4-2.0 (cm, 2H), 2.0 (s, 3H), 2.4-4.4 (cm, 25H), 6.4-7.6 (cm, 5H) | 584 (M + 1)⁺ | 11% |
| 12 | 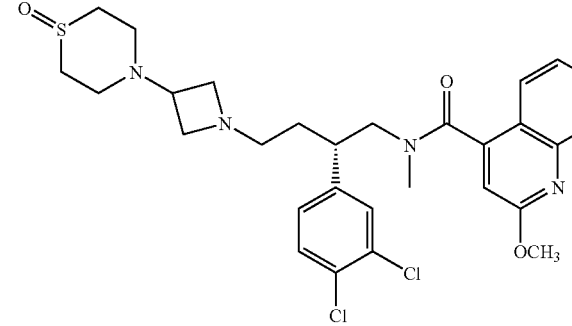 | — | 589 (M + 1)⁺ | 5% |
| 13 | 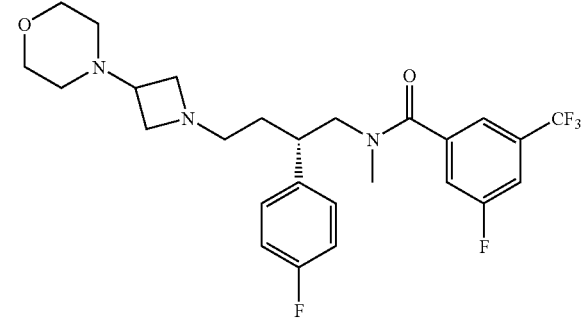 | (500 MHz, CDCl₃): 1.4-1.8 (cm, 2H), 2.2-2.6 (cm, 8H), 2.7-3.2 (cm, 5H), 3.4-3.5 (cm, 3H), 3.6-3.8 (cm, 5H), 6.8-7.4 (cm, 7H) | 512 (M + 1)⁺ | 56% |

-continued
| Ex | Compound | ¹H NMR | LCMS | Yield |
|----|----------|--------|------|-------|
| 14 | 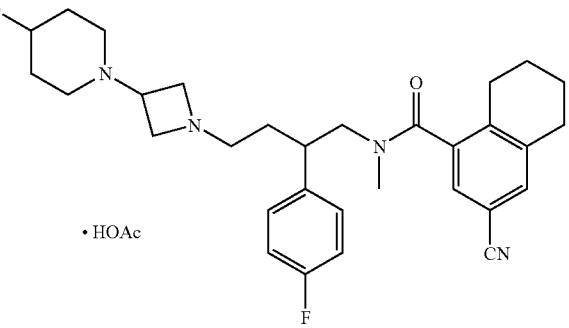 · HOAc | (400 MHz, CD₃OD): 1.4-4.2 (cm, 35H), 6.7-7.5 (cm, 6H) | 519 (M + 1)⁺ | 17% |
| 15 | 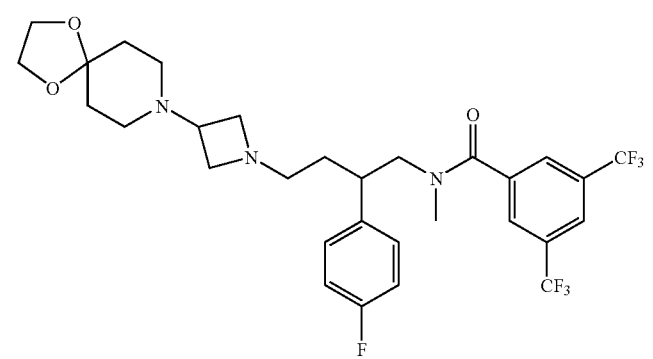 | (400 MHz, CDCl₃): 1.4-1.6 (b, 1H), 1.8 (s, 5H), 2.2-4.0 (cm, 21H), 6.8-7.5 (cm, 6H), 7.8 (s, 1H) | 618 (M + 1)⁺ | 40% |
| 16 | 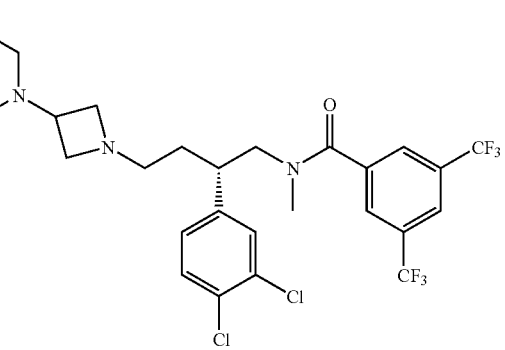 | (500 MHz, CDCl₃): 1.4-3.8 (cm, 22H), 3.6-3.8 (m, 1H), 4.6-4.8 (d, 1H), 6.7-7.6 (cm, 5H), 7.9 (s, 1H) | 628 (M + 1)⁺ | 30% |
| 17 | 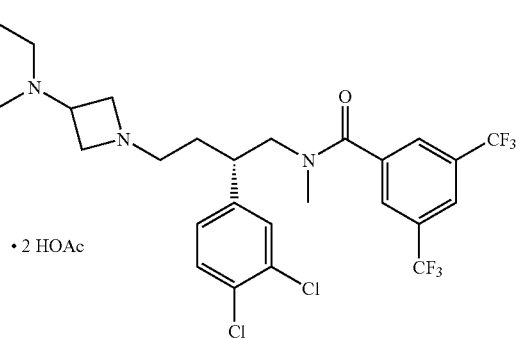 · 2 HOAc | (500 MHz, CD₃OD): 1.5-4.0 (cm, 25H), 6.9-7.7 (cm, 5H), 8.1 (s, 1H) | 626 (M + 1)⁺ | 13% |

Example 18

3-Cyano-N-{(2S)-2-(3,4-dichlorophenyl)-4-[3-(3-hydroxypyrrolidin-1-yl)azetidin-1-yl]butyl}-N-methyl-1-naphthamide acetate

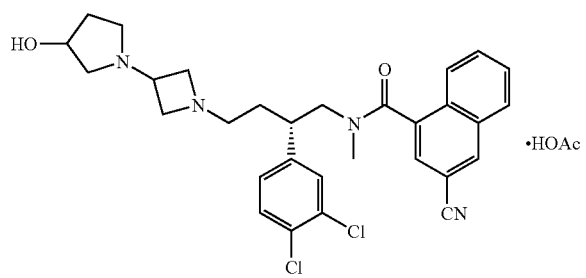

3-Cyano-N-[(2S)-2-(3,4-dichlorophenyl)-4-oxobutyl]-N-methyl-1-naphthamide (see WO 00/02859; 38 mg, 0.089 mmol) was dissolved in CH$_2$Cl$_2$ (3 mL) and to the resultant solution was added 1-azetidin-3-ylpyrrolidin-3-ol dihydrochloride (see Method 12; 20 mg, 0.093 mmol) dissolved in a few drops of methanol. Sodium triacetoxyborohydride (25 mg, 0.118 mmol) was added and the solution was stirred at room temperature over night. The mixture was diluted with CH$_2$Cl$_2$, washed with brine and then dried over MgSO$_4$. The solvent was removed by evaporation and the residue chromatographed on a reversed phase column using a mixture of acetonitrile and 0.1 M ammonium acetate aq. There was obtained 19 mg (35%) of the title compound as a white solid. $^1$H NMR (400 MHz, CD$_3$OD): 0.8-4.9 (cm, 25H), 6.4-7.9 (cm, 7H), 7.9-8.1 (m, 1H), 8.4 (s, 1H); LCMS: m/z 551 (M+1)$^+$.

Example 19

N-{(2S)-2-(4-Fluorophenyl)-4-[3-(4-fluoropiperidin-1-yl)azetidin-1-yl]butyl}-N-methyl-3,5-bis(trifluoromethyl)benzamide

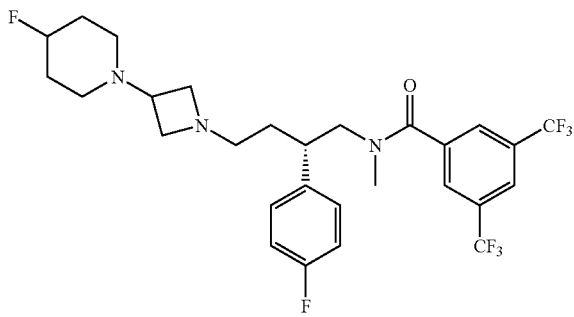

N-[(2S)-2-(4-Fluorophenyl)-4-oxobutyl]-N-methyl-3,5-bis(trifluoromethyl)benzamide (see Method 20; 189 mg, 0.43 mmol), 1-azetidin-3-yl-4-fluoropiperidine dihydrochloride (see WO 97/27185; 139 mg, 0.56 mmol) and triethylamine (154 mg, 1.52 mmol) were dissolved in methanol (10 mL). A methanol solution (5 mL) of sodium cyanoborohydride (191 mg, 3.04 mmol) and zinc chloride (178 mg, 1.30 mmol) was added and the mixture stirred at room temperature for 20 minutes. The solvent was removed by evaporation and the residue partitioned between water and ethyl acetate. The organic solution was washed with aqueous NaHCO$_3$ (1 M) and then brine. The solution was dried over Na$_2$SO$_4$ and then the solvent was removed by evaporation. The product was chromatographed on silica gel using a gradient of methanol and CH$_2$Cl$_2$ (0% MeOH-20% MeOH). There was obtained 120 mg (48%) of the title compound as a gum. $^1$H NMR (500 MHz, CDCl$_3$): 1.4-1.9 (cm, 6H), 2.1-2.4 (cm, 6H), 2.6-3.5 (cm, 10H), 3.6-3.8 (m, 1H), 4.6-4.8 (bd, 1H), 6.8-7.5 (m, 6H), 7.8 (s, 1H); LCMS: m/z 578 (M+1)$^+$.

Example 20

3-Cyano-N-[(2S)-2-(4-fluorophenyl)-4-(3-morpholin-4-ylazetidin-1-yl)butyl]-N-methyl-5,6,7,8-tetrahydronaphthalene-1-carboxamide

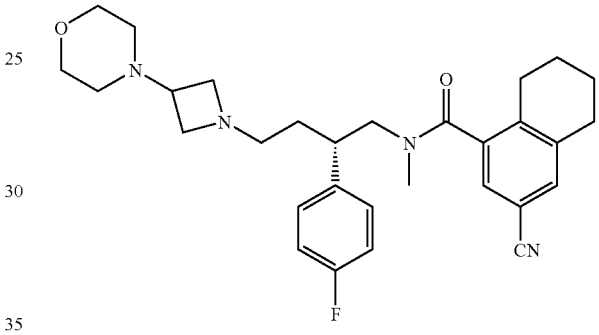

3-Cyano-N-[(2S)-2-(4-fluorophenyl)-4-oxobutyl]-N-methyl-5,6,7,8-tetrahydronaphthalene-1-carboxamide (see Method 19; 2.38 g, 6.3 mmol) and 4-azetidin-3-ylmorpholine dihydrochloride (see WO 00/63168; 1.49 g, 6.9 mmol) were mixed together with CH$_2$Cl$_2$ (120 mL) and DIPEA (1.63 g, 12.6 mmol). The mixture was stirred until all the chemicals were dissolved. Sodium triacetoxyborohydride (1.87 g, 8.8 mmol) was added and the solution was stirred at room temperature overnight. The solvent was removed and the residue was partitioned between ethyl acetate and saturated NaHCO$_3$ (aq). The phases were separated and the aqueous solution was extracted with ethyl acetate. The combined organic solutions were dried over MgSO$_4$ and the solvent was removed by evaporation. The residue was diluted with a small amount of acetonitrile and the solution was kept in a freezer overnight. The crystals were collected by filtration and more material was then obtained from the mother liquor by an additional crystallisation from acetonitrile. There was obtained 1.43 g (45%) in total of the title compound as an off-white solid. $^1$H NMR (500 MHz, CD$_3$OD): 1.4-4.2 (cm, 31H), 7.0-7.6 (cm, 6H); LCMS: m/z 505 (M+1)$^+$.

The material was shown to be 99.6% optically pure (enantiomeric excess) by analytical chiral HPLC (Chiralpak AD, 250×4.6 mm) using a mixture of heptane, isopropyl alcohol, triethylamine and formic acid (70/30/0.1/0.05) as mobile phase.

Example 21

N-{(2S)-2-(4-fluorophenyl)-4-[3-(4-hydroxypiperidin-1-yl)azetidin-1-yl]butyl}-N-methyl-3,5-bis(trifluoromethyl)benzamide

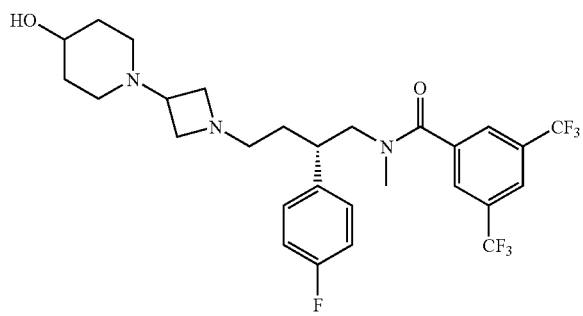

N-[(2S)-2-(4-Fluorophenyl)-4-oxobutyl]-N-methyl-3,5-bis(trifluoromethyl)benzamide (see Method 20; 0.40 g, 0.91 mmol) was dissolved in $CH_2Cl_2$ (10 mL) and to the resultant solution were added 1-azetidin-3-ylpiperidin-4-ol diacetate (see Method 15 with the exception that the diacetate was used rather than the corresponding dihydrochlorid; 0.28 g, 1.0 mmol) and DIPEA (0.76 g, 5.8 mmol). The mixture was stirred for a few minutes at RT and then sodium triacetoxyborohydride (0.43 g, 2.0 mmol) was added. The solution was stirred at RT overnight and then the solvent was removed by evaporation. The residue was partitioned between ethyl acetate and saturated $NaHCO_3$ (aq). The phases were separated and the aqueous solution was extracted twice with ethyl acetate. The combined organic solutions were washed with water, dried over $Na_2SO_4$ and then the solvent was removed by evaporation. The residue was purified by flash chromatography using a mixture of methanol and $CH_2Cl_2$ as eluent. The product was dissolved in a mixture of water and acetonitrile and the solution was then freeze-dried. There was obtained 0.32 g (60%) of the title compound as a white solid. $^1$H NMR (400 MHz, $CDCl_3$): 1.4-3.8 (cm, 24H), 6.8-7.5 (cm, 6H), 7.9 (s, 1H); LCMS: m/z 576 (M+1)$^+$.

Example 22

3,5-Dichloro-N-[(2S)-2-(4-fluorophenyl)-4-(3-morpholin-4-ylazetidin-1-yl)butyl]-N-methylbenzamide

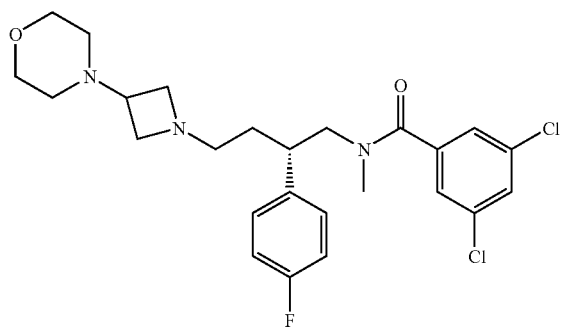

3,5-Dichloro-N-[(2S)-2-(4-fluorophenyl)-4-oxobutyl]-N-methylbenzamide (see Method 21; 146 mg, 0.40 mmol) was dissolved in $CH_2Cl_2$ (8 mL) and to the resultant solution were added 4-azetidin-3-ylmorpholine dihydrochloride (see WO 00/63168; 62 mg, 0.44 mmol) and DIPEA (179 mg, 1.39 mmol) together with 5 drops of acetic acid. The mixture was stirred for 25 minutes and then sodium triacetoxyborohydride (118 mg, 0.55 mmol) was added. The mixture was stirred at room temperature overnight. The solvent was evaporated and the residue was partitioned between ethyl acetate and saturated $NaHCO_3$ aq. The phases were separated and the aqueous solution was extracted with ethyl acetate. The combined organic solutions were dried over $MgSO_4$ and the solvent was removed by evaporation. The residue was chromatographed on silica gel using a mixture of methanol and $CH_2Cl_2$ as eluent (gradient 0 to 20% methanol). There was obtained 124 mg (63%) of the title compound as an oil. $^1$H NMR (500 MHz, $CDCl_3$): 1.4-1.8 (cm, 2H), 2.2-3.8 (cm, 21H), 6.7 (s, 1H), 6.8-7.2 (m, 5H), 7.3 (s, 1H); LCMS: m/z 494 (M+1)$^+$.

The material was shown to be 95% optically pure (enantiomeric excess) by analytical chiral HPLC (Chirobiotic V, 250×4.6 mm) using a mixture of methanol, triethylamine and acetic acid (100/0.1/0.05) as mobile phase.

Examples 23-39

The following compounds, which are tabulated below, were synthesized in an analogous way to that of Example 18, Example 19, Example 20, Example 21 and Example 22 using the appropriate amine and aldehyde intermediates (see below): 3-Cyano-N-[(2S)-2-(3,4-dichlorophenyl)-4-(3-morpholin-4-ylazetidin-1-yl)butyl]-N-methyl-1-naphthamide acetate (Ex 23), 3-Cyano-N-[(2S)-2-(3,4-dichlorophenyl)-4-(3-thiomorpholin-4-ylazetidin-1-yl)butyl]-N-methyl-1-naphthamide acetate (Ex 24), 3-Cyano-N-{(2S)-2-(3,4-dichlorophenyl)-4-[3-(1,4-dioxa-8-azaspiro[4.5]dec-8-yl)azetidin-1-yl]butyl}-N-methyl-1-naphthamide diacetate, (Ex 25), 3-Cyano-N-{(2S)-2-(3,4-dichlorophenyl)-4-[3-(4-hydroxypiperidin-1-yl)azetidin-1-yl]butyl}-N-methyl-1-naphthamide diacetate (Ex 26), 3-Cyano-N-[2-(4-fluorophenyl)-4-(3-thiomorpholin-4-ylazetidin-1-yl)butyl]-N-methyl-1-naphthamide (Ex 27), 3-Cyano-N-[2-(4-cyanophenyl)-4-(3-thiomorpholin-4-ylazetidin-1-yl)butyl]-N-methyl-1-naphthamide acetate (Ex 28), 3-Cyano-N-{(2S)-2-(3,4-dichlorophenyl)-4-[3-(1,1-dioxidothiomorpholin-4-yl)azetidin-1-yl]butyl}-N-methyl-1-naphthamide acetate (Ex 29), 3-Cyano-N-{(2S)-2-(4-fluorophenyl)-4-[3-(4-hydroxypiperidin-1-yl)azetidin-1-yl]butyl}-N-methyl-5,6,7,8-tetrahydronaphthalene-1-carboxamide (Ex 30), 3-Cyano-N-ethyl-N-[(2S)-2-(4-fluorophenyl)-4-(3-morpholin-4-ylazetidin-1-yl)butyl]-5,6,7,8-tetrahydronaphthalene-1-carboxamide (Ex 31), 3-Cyano-N-[(2S)-4-[3-(1,4-dioxa-8-azaspiro[4.5]dec-8-yl)azetidin-1-yl]-2-(4-fluorophenyl)butyl]-N-methyl-5,6,7,8-tetrahydronaphthalene-1-carboxamide (Ex 32), 3-cyano-N-[(2S)-2-(4-fluorophenyl)-4-(3-morpholin-4-ylazetidin-1-yl)butyl]-N-methyl-1-naphthamide (Ex 33), 3-Cyano-N-{(2S)-2-(4-fluorophenyl)-4-[3-(1,4-oxazepan-4-yl)azetidin-1-yl]butyl}-N-methyl-5,6,7,8-tetrahydronaphthalene-1-carboxamide (Ex 34), 3-Fluoro-N-[(2S)-2-(4-fluorophenyl)-4-(3-morpholin-4-ylazetidin-1-yl)butyl]-N-methyl-5,6,7,8-tetrahydronaphthalene-1-carboxamide acetate (Ex 35), 3,5-Dibromo-N-{(2S)-2-(4-fluorophenyl)-4-[3-(4-hydroxypiperidin-1-yl)azetidin-1-yl]butyl}-N-methylbenzamide (Ex 36), 3-Bromo-N-[(2S)-2-(4-fluorophenyl)-4-(3-morpholin-4-ylazetidin-1-yl)butyl]-5-iodo-N-methylbenzamide dihydrochloride (Ex 37), 3-Cyano-N-[2-(4-fluoro-2-methylphenyl)-4-(3-morpholin-4-ylazetidin-1-yl)butyl]-N-methyl-5,6,7,8-tetrahydronaphthalene-1-carboxamide dihydrochloride (Ex 38), 6-Cyano- N-[(2S)-2-(4-fluorophenyl)-4-(3-morpholin-4-ylazetidin-1-yl)butyl]-N-methylindane-4-carboxamide (Ex 39).

The syntheses of the amine and aldehyde intermediates used in the examples below are described in the following referred Methods (Meth) or in the following cited documents: Ex 23 (see WO 00/63168 and WO 00/02859), Ex 24 (see WO 96/05193 and WO 00/02859), Ex 25 (see Meth 13 and WO 00/02859), Ex 26 (see Meth 15 and WO 00/02859), Ex 27 (see WO 96/05193 and Meth 17), Ex 28 (see WO 96/05193 and Meth 18), Ex 29 (see Meth 14 and WO 00/02859), Ex 30 (see Meth 15 and Meth 19), Ex 31 (see WO 00/63168 and Meth 22), Ex 32 (see Meth 13 and Meth 19), Ex 33 (see WO 00/63168 and Meth 23), Ex 34 (see WO 96/05193 and Meth 19), Ex 35 (see WO 00/63168 and Meth 28), Ex 36 (see Meth 15 and Meth 24), Ex 37 (see WO 00/63168 and Meth 25), Ex 38 (see WO 00/63168 and Meth 26) and Ex 39 (see WO 00/63168 and Meth 27).

| Ex | Compound | $^1$H NMR | LCMS | Yield |
|---|---|---|---|---|
| 23 | · HOAc | (500 MHz, CDCl$_3$): 1.2-2.2 (cm, 3H), 2.0 (s, 3H), 2.2-5.0 (cm, 21H), 6.5-7.0 (cm, 1H), 7.2-8.0 (cm, 7H), 8.2 (d, 1H) | 551 (M + 1)$^+$ | 35% |
| 24 | · HOAc | (400 MHz, DMSO-d$_6$): 1.2-2.2 (cm, 3H), 1.90 (s, 3H), 2.3-4.5 (cm, 21H), 6.4-7.3 (cm, 2H), 7.4 (dd, 1H), 7.5-7.8 (cm, 4H), 8.0-8.2 (m, 1H), 8.6 (d, 1H) | 567 (M + 1)$^+$ | 51% |
| 25 | · 2 HOAc | (400 MHz, CD$_3$OD): 1.4-2.0 (cm, 3H), 1.6-1.8 (m, 4H), 1.9 (s, 6H), 2.3-4.0 (cm, 20H), 6.4-7.2 (m, 2H), 7.4-7.8 (m, 5H), 8.0-8.1 (m, 1H), 8.4 (d, 1H) | 607 (M + 1)$^+$ | 78% |
| 26 | · 2 HOAc | (400 MHz, CD$_3$OD): 1.4-2.4 (cm, 16H), 2.5-2.9 (cm, 5H), 3.0-4.1 (cm, 9H), 6.5-7.8 (cm, 7H), 8.0-8.1 (m, 1H), 8.4 (d, 1H) | 565 (M + 1)$^+$ | 14% |

-continued
| Ex | Compound | ¹H NMR | LCMS | Yield |
|---|---|---|---|---|
| 27 | 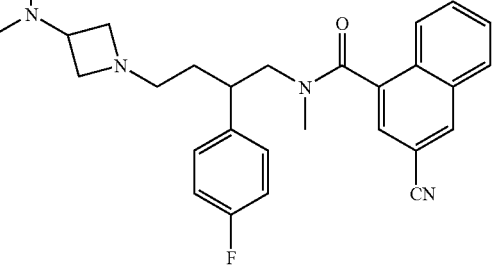 | (400 MHz, CDCl₃): 1.4-3.5 (cm, 22H), 3.8-4.4 (cm, 1H), 6.4-8.0 (cm, 8H), 8.2 (s, 1H) | 517 (M + 1)⁺ | 94% |
| 28 | 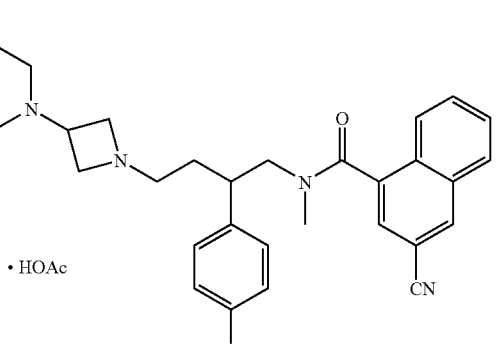 · HOAc | (400 MHz, CDCl₃): 1.2-2.2 (cm, 3H), 2.1 (s, 3H), 2.4-4.4 (cm, 20H), 6.6-7.8 (cm, 8H), 7.9 (d, 1H), 8.2 (s, 1H) | 524 (M + 1)⁺ | 52% |
| 29 | 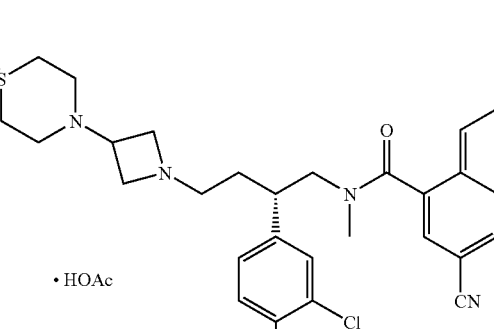 · HOAc | (400 MHz, DMSO-d₆): 1.2-1.9 (cm, 3H), 1.9 (s, 3H), 2.0-4.8 (cm, 20H), 6.4-7.8 (cm, 7H), 8.0-8.2 (m, 1H), 8.6 (d, 1H) | 599 (M + 1)⁺ | 39% |
| 30 | 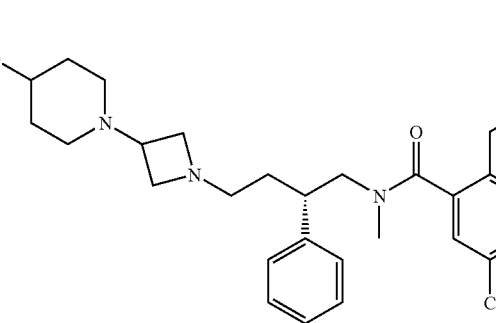 | (500 MHz, CDCl₃): 1.5-4.1 (cm, 33H), 6.0-7.4 (cm, 6H) | 519 (M + 1)⁺ | 63% |

| Ex | Compound | ¹H NMR | LCMS | Yield |
|---|---|---|---|---|
| 31 | 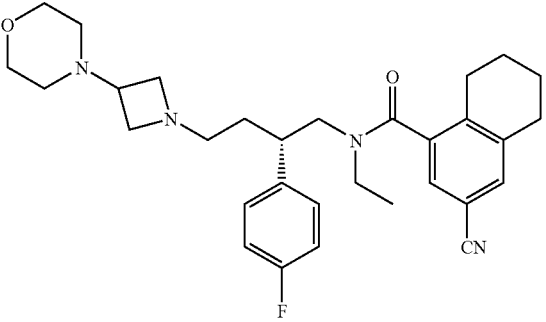 | (500 MHz, CDCl₃): 0.9-4.1 (cm, 33H), 6.0-7.4 (cm, 6H) | 519 (M + 1)⁺ | 38% |
| 32 | 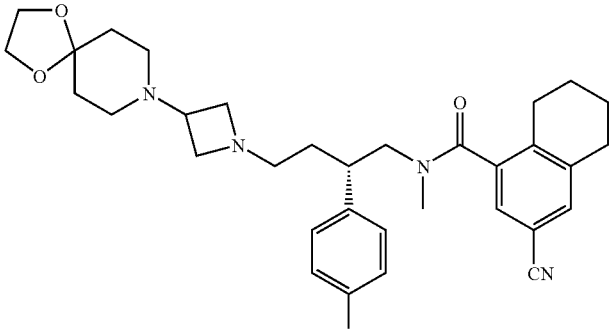 | (400 MHz, CDCl₃): 1.4-4.1 (cm, 35H), 6.1-7.4 (cm, 6H) | 561 (M + 1)⁺ | 52% |
| 33 | 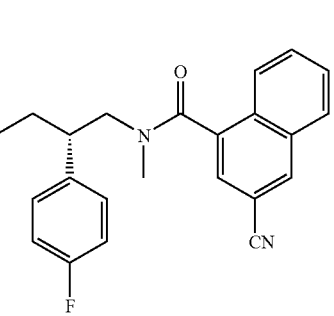 | (400 MHz, CDCl₃): 1.2-4.4 (cm, 23H), 6.4-8.0 (cm, 9H), 8.2 (s, 1H) | 501 (M + 1)⁺ | 61% |
| 34 | 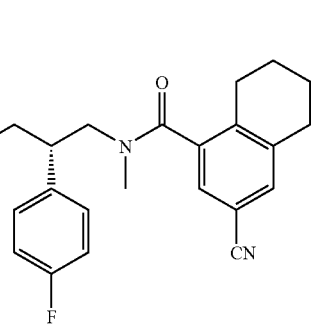 | (500 MHz, CDCl₃): 1.2-4.2 (cm, 33H), 6.0 (s) and 6.6-7.4 (cm, 6H) | 519 (M + 1)⁺ | 41% |

| Ex | Compound | ¹H NMR | LCMS | Yield |
|---|---|---|---|---|
| 35 | 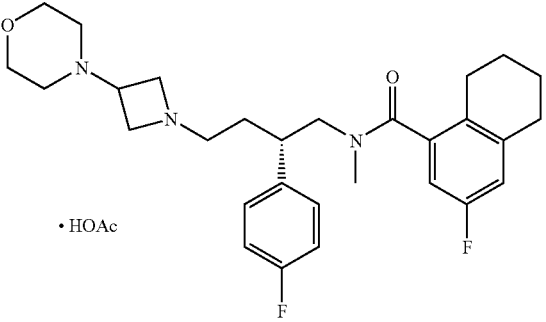 · HOAc | (500 MHz, DMSO-d₆): 1.3-4.1 (cm, 34H), 5.6 (d), 6.2 (s) and 6.6-7.4 (cm, 6H) | 498 (M + 1)⁺ | 35% |
| 36 | 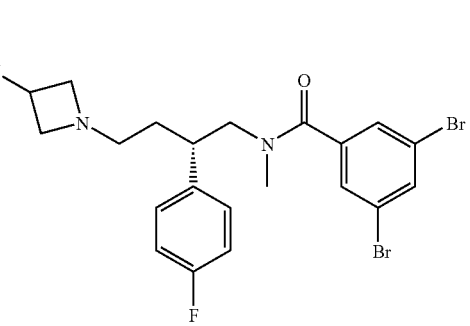 | (500 MHz, CDCl₃): 1.5-3.8 (cm, 25H), 6.2-7.3 (cm, 6H), 7.6 (s, 1H) | 598 (M + 1)⁺ | 10% |
| 37 | 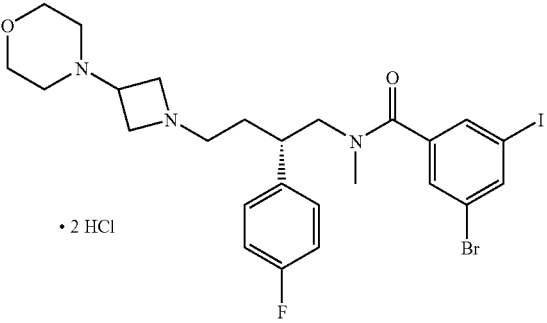 · 2 HCl | (500 MHz, CD₃OD): 1.8-2.2 (cm, 2H), 2.8-4.8 (cm, 21), 6.9-7.5 (cm, 6H), 8.0 (d, 1H) | 631 (M + 1)⁺ | 34% |
| 38 | 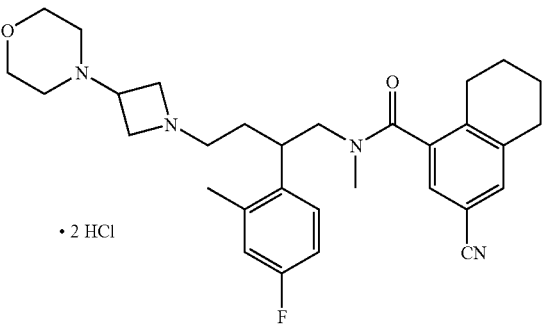 · 2 HCl | (300 MHz, D₂O): 1.4-4.4 (cm, 34H), 5.8 (s) and 6.8-7.5 (cm, 5H) | 519 (M + 1)⁺ | 59% |

| Ex | Compound | ¹H NMR | LCMS | Yield |
|---|---|---|---|---|
| 39 | 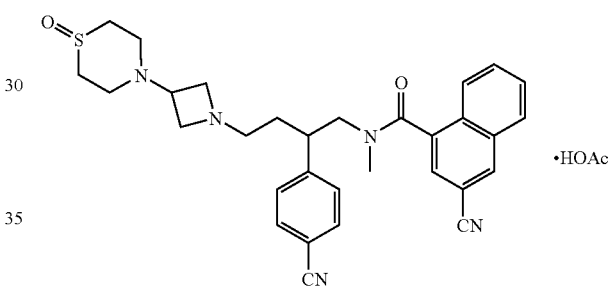 | (400 MHz, CDCl₃): 1.2-4.0 (cm, 29H), 6.8-7.2 (cm, 3H), 7.2-7.3 (m, 2H), 7.5 (d, 1H) | 491 (M + 1)⁺ | 75% |

Example 40

3-Cyano-N-{(2S)-2-(3,4-dichlorophenyl)-4-[3-(1-oxidothiomorpholin-4-yl)azetidin-1-yl]butyl}-N-methyl-1-naphthamide diacetate

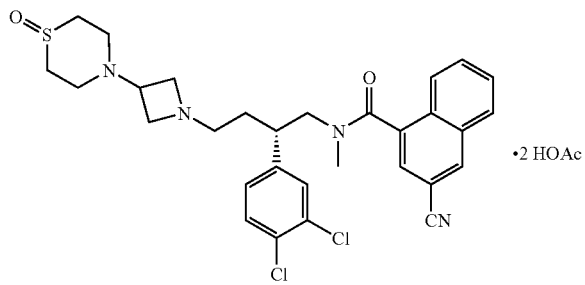

3-Cyano-N-[(2S)-2-(3,4-dichlorophenyl)-4-(3-thiomorpholin-4-ylazetidin-1-yl)butyl]-N-methyl-1-naphthamide acetate (see Example 24; 127 mg, 0.20 mmol) was dissolved in acetic acid (10 mL) and to the resultant solution was added hydrogen peroxide (0.04 mL of 30% aqueous solution, 0.35 mmol). The mixture was stirred at room temperature for 3 days then diluted with water. The solvent was removed by lyophilising the mixture to give a residue, which was purified by reversed phase chromatography using a mixture of acetonitrile and 0.1 M ammonium acetate aq. There was obtained 52 mg (35%) of the title compound as a white solid. ¹H NMR (400 MHz, DMSO-d₆): 1.2-2.2 (m, 3H), 1.9 (s, 3H), 2.3-3.6 (m, 20H), 4.4 (c m, 1H), 6.4-7.6 (m, 2H), 7.4 (dd, 1H), 7.6-8.2 (5H), 8.6 (d, 1H); LCMS: m/z 583 (M+1)⁺.

Example 41

3-Cyano-N-{2-(4-cyanophenyl)-4-[3-(1-oxidothiomorpholin-4-yl)azetidin-1-yl]butyl}-N-methyl-1-naphthamide acetate 3-Cyano-N-[2-(4-cyanophenyl)-4-(3-thiomorpholin-4-ylazetidin-1-yl)butyl]-N-methyl-1-naphthamide acetate (see Example 28; 60 mg, 0.10 mmol) was dissolved in a mixture of acetonitrile (3 mL) and CH₂Cl₂ (1 mL) and to the resultant solution was added a catalytic amount of FeCl₃ with cooling. The mixture was stirred for 5 min and then periodic acid (26 mg, 0.11 mmol) was added whereupon stirring was continued overnight at 0° C. Another catalytic amount of FeCl₃ as well as an additional portion of periodic acid (26 mg, 0.11 mmol) was added. The reaction mixture was stirred at 0° C. for 2 h and then quenched by addition of Na₂S₂O₃. The mixture was extracted thrice with CH₂Cl₂ and the organics washed twice with water and then dried over Na₂SO₄. The solvent was removed by evaporation and the product was purified by reversed phase chromatography using a mixture of acetonitrile and 0.1 M ammonium acetate aq. There was obtained 25 mg (41%) of the title compound as a pale yellow solid. ¹H NMR: (400 MHz, CDCl₃): 1.4-2.0 (cm, 3H), 2.0 (s, 3H), 2.1-4.3 (cm, 20H), 6.4-8.0 (cm, 9H), 8.2 (s, 1H); LCMS: m/z 540 (M+1)⁺.

Examples 42-47

The following compounds, which are tabulated below, were synthesized in an analogous way to that of Example 40 and Example 41 using the appropriate thiomorpholine intermediates (see below): 3,5-Dichloro-N-{(2S)-2-(3,4-dichlorophenyl)-4-[3-(1-oxidothiomorpholin-4-yl)azetidin-1-yl]

butyl}-N-methylbenzamide acetate (Ex 42), N-[(2S)-2-(3,4-Dichlorophenyl)-4-(3-oxidothiomorpholin-4-ylazetidin-1-yl)butyl]-N-methyl-3,5-bis(trifluoromethyl)benzamide acetate (Ex 43), 3-Cyano-N-{(2S)-2-(3,4-dichlorophenyl)-4-[3-(1-oxidothiomorpholin-4-yl)azetidin-1-yl]butyl}-N-methyl-5,6,7,8-tetrahydronaphthalene-1-carboxamide acetate (Ex 44), 3-Cyano-N-{2-(4-fluorophenyl)-4-[3-(1-oxidothiomorpholin-4-yl)azetidin-1-yl]butyl}-N-methyl-1-naphthamide acetate (Ex 45), 3-cyano-N-{2-(4-fluorophenyl)-4-[3-(1-oxidothiomorpholin-4-yl)azetidin-1-yl]butyl}-N-methyl-5,6,7,8-tetrahydronaphthalene-1-carboxamide acetate (Ex 46) and N-{2-(4-Fluorophenyl)-4-[3-(1-oxidothiomorpholin-4-yl)azetidin-1-yl]butyl}-N-methyl-3,5-bis(trifluoromethyl)benzamide acetate (Ex 47).

The syntheses of the thiomorpholine intermediates used in the examples below are described in the following referred Examples: Ex 42 (see Ex 1), Ex 43 (see Ex 4), Ex 44 (see Ex 7), Ex 45 (see Ex 27), Ex 46 (see Ex 9) and Ex 47 (see Ex 10).

| Ex | Compound | $^1$H NMR | LCMS | Yield |
|---|---|---|---|---|
| 42 | [structure] · HOAc | (300 MHz, CD$_3$OD): 1.6 (b, 1H), 1.8 (b, 1H), 2.0 (s, 3H), 2.2-3.8 (cm, 21H), 6.8-7.6 (cm, 6H) | 576 (M + 1)$^+$ | 1% |
| 43 | [structure] · HOAc | (300 MHz, CD$_3$OD): 1.5-2.0 (cm, 2H), 2.0 (s, 3H), 2.2-4.0 (cm, 18H), 6.8-7.8 (cm, 5H), 8.1 (s, 1H) | 644 (M + 1)$^+$ | 9% |
| 44 | [structure] · HOAc | (400 MHz, CDCl$_3$): 1.4-4.4 (cm, 35H), 6.7-7.2 (cm, 2H), 7.3 (s, 1H), 7.4 (s, 1H), 7.5 (d, 1H) | 587 (M + 1)$^+$ | 37% |
| 45 | [structure] · HOAc | (400 MHz, CDCl$_3$): 1.4-2.0 (cm, 3H), 2.0 (s, 3H), 2.1-4.3 (cm, 20H), 6.4-8.0 (cm, 9H), 8.2 (s, 1H) | 533 (M + 1)$^+$ | 42% |

| Ex | Compound | ¹H NMR | LCMS | Yield |
|----|----------|--------|------|-------|
| 46 | 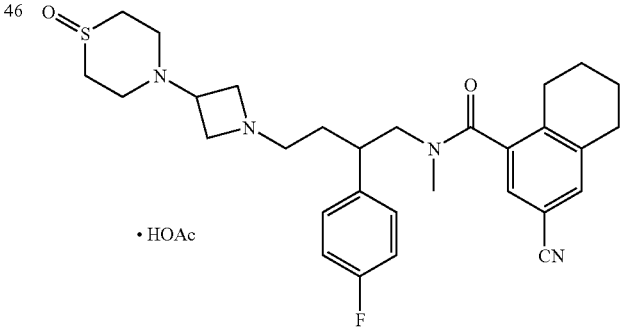 • HOAc | (400 MHz, CDCl$_3$): 1.4-2.0 (cm, 6H), 2.0 (s, 3H), 2.1-4.0 (cm, 25H), 6.9-7.4 (cm, 6H) | 537 (M + 1)$^+$ | 38% |
| 47 | 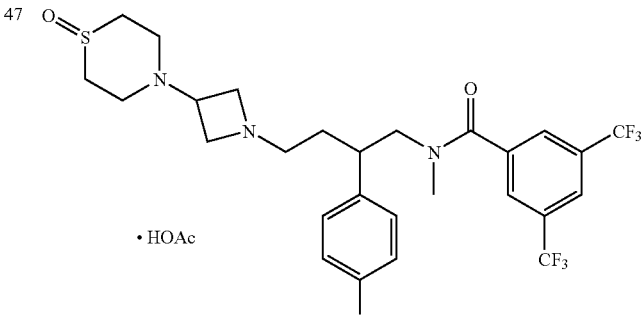 • HOAc | (400 MHz, CDCl$_3$): 1.4-2.0 (cm, 3H), 2.0 (s, 3H), 2.1-4.4 (cm, 21H), 6.7-7.4 (cm, 5H), 7.5 (s, 1H), 8.2 (s, 1H) | 594 (M + 1)$^+$ | 47% |

Example 48

3-Cyano-N-{(2S)-2-(3,4-dichlorophenyl)-4-[3-(4-oxopiperidin-1-yl)azetidin-1-yl]butyl}-N-methyl-1-naphthamide diacetate

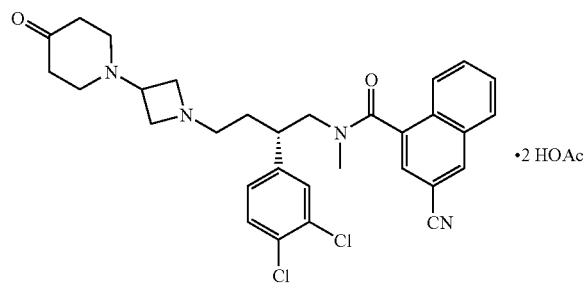

3-cyano-N-{(2S)-2-(3,4-dichlorophenyl)-4-[3-(1,4-di-oxa-8-azaspiro[4.5]dec-8-yl)azetidin-1-yl]butyl}-N-methyl-1-naphthamide diacetate (see Example 25; 35 mg, 0.058 mmol) was dissolved in a few drops of acetone-water (1:1) and to the resultant solution was added pyridinium p-toluenesulfonate (43 mg, 0.17 mmol). The mixture was subjected to microwave single node heating for 10 min and then the solvent was removed by evaporation. The residue was dissolved in CH$_2$Cl$_2$ and the solution was washed with NaHCO$_3$ aq. then dried over MgSO$_4$. Removal of solvent by evaporation yielded an oil, which was purified by reversed phase chromatography using a mixture of acetonitrile and 0.1 M ammonium acetate aq. There was obtained 35 mg (89%) of the title compound as a white solid. ¹H NMR (400 MHz, CD$_3$OD): 1.4-2.2 (cm, 3H), 1.9 (s, 6H), 2.3-4.0 (cm, 20H), 6.4-7.8 (cm, 7H), 8.0-8.2 (cm, 1H), 8.6 (d, 1H); LCMS: m/z 563 (M+1)$^+$.

Example 49

The following compound, which is tabulated below, was synthesized in an analogous way to that of Example 48 using the appropriate ketal derivative (see Ex 15): N-{2-(4-fluorophenyl)-4-[3-(4-oxopiperidin-1-yl)azetidin-1-yl]butyl}-N-methyl-3,5-bis(trifluoromethyl)benzamide.

| Ex | Compound | ¹H NMR | LCMS | Yield |
|---|---|---|---|---|
| 49 | | (400 MHz, CDCl$_3$): 1.5-3.9 (cm, 23H), 6.8-7.6 (cm, 6H), 7.9 (s, 1H) | 574 (M + 1)$^+$ | 71% |

Example 50

3-Cyano-N-{(2S)-2-(3,4-dichlorophenyl)-4-[3-(4-fluoropiperidin-1-yl)azetidin-1-yl]butyl}-N-methyl-1-naphthamide

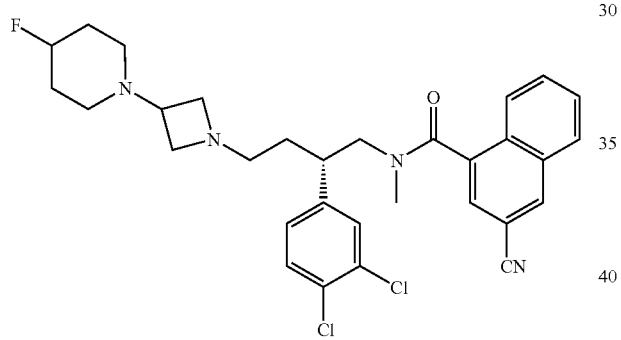

Diethylaminosulfur trifluoride (7 mg, 0.044 mmol) was dissolved in dry CH$_2$Cl$_2$ and cooled with stirring under argon to −65° C. 3-Cyano-N-{(2S)-2-(3,4-dichlorophenyl)-4-[3-(4-oxopiperidin-1-yl)azetidin-1-yl]butyl}-N-methyl-1-naphthamide (Example 26; 40 mg, 0.071 mmol), which was dissolved in dry CH$_2$Cl$_2$ (0.5 mL), was then added. The external cooling was removed and the solution was stirred for 1 h. The reaction mixture was quenched by dropping it to a saturated solution of NaHCO$_3$ aq. (6 mL). The organic solution was washed with water and then dried over MgSO$_4$. The solvent was removed by evaporation and there was obtained 5 mg (12%) of the title compound as an oil. ¹H NMR (500 MHz, CD$_3$OD): 1.8-2.6 (cm, 7H), 2.6-3.3 (cm, 7H), 3.4-4.4 (cm, 9H), 5.0-5.3 (cm, 1H), 7.0-8.4 (cm, 7H), 8.4-8.6 (m, 1H), 8.9-9.0 (d, 1H); LCMS: m/z 567 (M+1)$^+$.

Example 51

The following compound, which is tabulated below, was synthesized in an analogous way to that of Example 50 using the appropriate alcohol derivative (see Ex 14): 3-Cyano-N-{2-(4-fluorophenyl)-4-[3-(4-fluoropiperidin-1-yl)azetidin-1-yl]butyl}-N-methyl-5,6,7,8-tetrahydronaphthalene-1-carboxamide.

| Ex | Compound | ¹H NMR | LCMS | Yield |
|---|---|---|---|---|
| 51 | · HOAc | (400 MHz, CD$_3$OD): 1.5-4.2 (cm, 34H), 4.5-4.8 (m, 1H), 5.8 (s), 6.8 (s) and 7.0-7.5 (cm, 6H) | 521 (M + 1)$^+$ | 6% |

Example 52

3-Cyano-N-{(2S)-2-(3,4-dichlorophenyl)-4-[3-(4-methylpiperazin-1-yl)azetidin-1-yl]butyl}-N-methyl-1-naphthamide

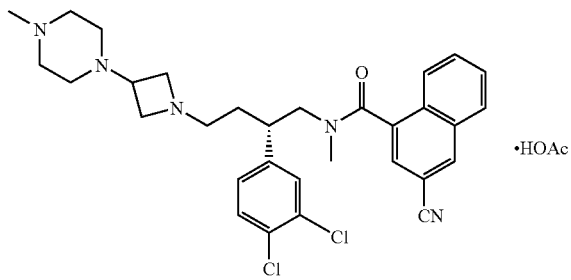

1-[(3S)-4-[(3-Cyano-1-naphthoyl)(methyl)amino]-3-(3,4-dichlorophenyl)butyl]azetidin-3-yl methanesulfonate (Method 16; 87 mg, 0.16 mmol) and 1-methylpiperazine (1 mL, 9.0 mmol) were dissolved in CH$_2$Cl$_2$ (1.5 mL) and the resultant mixture was subjected to microwave single node heating for 5 minutes. The solvent was removed by evaporation and the product was purified by reversed phase chromatography using a mixture of acetonitrile and 0.1 M ammonium acetate aq. There was obtained 5 mg (5%) of the title compound as a white solid. $^1$H NMR: (500 MHz, CD$_3$OD): 1.2-4.0 (cm, 29H), 6.5-8.0 (cm, 8H), 8.4 (d, 1H); LCMS: m/z 564 (M+1)$^+$.

Examples 53-54

The following compounds, which are tabulated below, were synthesized in an analogous way to that of Example 52 using the appropriate amine and mesylate intermediates (see below): N-[(2S)-4-[3-(4-Acetylpiperazin-1-yl)azetidin-1-yl]-2-(3,4-dichlorophenyl)butyl]-3-cyano-N-methyl-1-naphthamide acetate (Ex 53), 3-Cyano-N-[(2S)-4-[3-(4-cyanopiperidin-1-yl)azetidin-1-yl]-2-(3,4-dichlorophenyl)butyl]-N-methyl-1-naphthamide acetate (Ex 54).

The syntheses of the amine and methanesulfonate intermediates used in the examples below are described in the following referred Methods (Meth) or in the following cited documents: Ex 53 (see WO 96/05193 and Meth 16) and Ex 54 (see Synth Commun; 1990; 1757-1767 and Meth 16).

| Ex | Compound | $^1$H NMR | LCMS | Yield |
|---|---|---|---|---|
| 53 | (structure) | (500 MHz, CD$_3$OD): 1.2-3.8 (cm, 29H), 6.4-7.8 (cm, 7H), 7.9-8.0 (m, 1H), 8.3-8.4 (d, 1H) | 592 (M + 1)$^+$ | 3% |
| 54 | (structure) | — | 574 (M + 1)$^+$ | 3% |

Preparation of Starting Materials

The starting materials for the examples above are either commercially available or are readily prepared by standard methods from known materials. For example, the following reactions are an illustration, but not a limitation, of some of the starting materials.

Method 1

[(2S)-2-(3,4-Dichlorophenyl)-4-(3-thiomorpholin-4-ylazetidin-1-yl)butyl]methylamine dihydrochloride

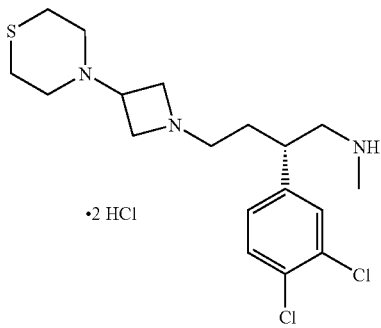

(a) 4-[1-(Diphenylmethyl)azetidin-3-yl]thiomorpholine

A mixture of 1-(Diphenylmethyl)azetidin-3-yl methanesulfonate (see J. Org. Chem.; 56; 1991; 6729; 10 g, 31.5 mmol), thiomorpholine (3.9 g, 38 mmol) and DIPEA (4.9 g, 38 mmol) was refluxed overnight. The volatiles were removed by evaporation and the residue was partitioned between $CH_2Cl_2$ and $NaHCO_3$ aq. The organic layer was washed twice with $NaHCO_3$ aq. and then extracted with an aqueous solution of citric acid (3×70 mL of 1M). The aqueous layer was cooled and then pH adjusted with aqueous $NaHCO_3$ and then 2M NaOH aq. The mixture was extracted with a mixture of $CH_2Cl_2$-EtOAc-ethanol and the organic solution was dried over $MgSO_4$ and then removed by evaporation. There was obtained 9.3 g (91%) of 4-[1-(diphenylmethyl)azetidin-3-yl]thiomorpholine as a pale yellow solid. $^1$H NMR (400 MHz, $CDCl_3$): 2.5 (m, 4H), 2.7 (m, 4H), 2.8 (t, 2H), 3.0 (qn 1H), 3.4 (m, 2H), 4.4 (s, 1H), 7.1-7.4 (m, 1OH); LCMS: m/z 325 (M+1)$^+$.

(b) 4-Azetidin-3-ylthiomorpholine dihydrochloride

4-[1-(Diphenylmethyl)azetidin-3-yl]thiomorpholine (1.0 g, 3.1 mmol) was dissolved in $CH_2Cl_2$ under nitrogen and stirred at 0° C. during the addition of 1-chloroethyl chloroformate (1.3 g, 9.2 mmol). The mixture was stirred for 90 min and then methanol (1 mL) was added. The solution was refluxed for 20 min and the solvent was removed by evaporation. To the residue was added acetone (10 mL) followed by isopropanol (10 mL) and the mixture was then refluxed for 30 min and then placed at room temperature overnight. The mixture was cooled and the precipitate was collected by filtration. There was obtained 250 mg (51%) of 4-azetidin-3-ylthiomorpholine dihydrochloride as a pale brown solid. $^1$H NMR (400 MHz, DMSO-$d_6$): 2.4-3.8 (cm, 8H), 4.0 (b, 2H), 4.3 (m, 1H), 4.5 (b, 2H) 9.2 (b, 1H), 10.4 (b, 1H).

(c) tert-Butyl [(2S)-2-(3,4-dichlorophenyl)-4-(3-thiomorpholin-4-ylazetidin-1-yl)butyl]methylcarbamate tert-Butyl [(2S)-2-(3,4-dichlorophenyl)-4-oxobutyl]methylcarbamate (see WO 95/05377; 610 mg, 1.8 mmol) was dissolved in 1,2-dichloroethane (20 mL) and to the resultant solution was added 4-azetidin-3-ylthiomorpholine hydrochloride (430 mg, 1.9 mmol) followed by the addition of sodium triacetoxyborohydride (480 mg, 2.2 mmol). The mixture was stirred at room temperature for 5 h and then triethylamine (0.73 mL, 5.2 mmol) was added. The reaction mixture was stirred for 2 h and then partitioned between $CH_2Cl_2$ and $NaHCO_3$ aq. The organic layer was washed with water and the combined organic solutions were dried over $MgSO_4$. The solvent was removed by evaporation to yield an oil, which was chromatographed on a reversed phase column using a mixture of acetonitrile and 0.1 M ammonium acetate aq. The appropriate fractions were extracted with ether. The organic solution was dried over $MgSO_4$ and then the solvent was removed by evaporation. There was obtained 266 mg (31%) of tert-butyl [(2S)-2-(3,4-dichlorophenyl)-4-(3-thiomorpholin-4-ylazetidin-1-yl)butyl]methylcarbamate as an oil. $^1$H NMR (400 MHz, $CDCl_3$): 1.4 (s, 9H), 1.5-3.5 (c m, 23H), 7.0 (dd, 1H), 7.3 (d, 1H), 7.4 (d, 1H); LCMS: m/z 488 (M+1)$^+$.

(d) [(2S)-2-(3,4-Dichlorophenyl)-4-(3-thiomorpholin-4-ylazetidin-1-yl)butyl]methylamine dihydrochloride tert-Butyl [(2S)-2-(3,4-dichlorophenyl)-4-(3-thiomorpholin-4-ylazetidin-1-yl)butyl]methylcarbamate (260 mg, 0.53 mmol) was dissolved in ether (15 mL) and stirred during the dropwise addition of HCl (15 mL of 4M dioxane solution). The mixture was stirred at room temperature for 1 h and then the solvent was removed by evaporation. There was obtained 270 mg (100%) of [(2S)-2-(3,4-dichlorophenyl)-4-(3-thiomorpholin-4-ylazetidin-1-yl)butyl]methylamine dihydrochloride as a white solid. $^1$H NMR (300 MHz, $CD_3OD$): 1.9-2.2 (b, 2H), 2.7 (s, 3H), 3.0-4.8 (cm, 19H), 7.4 (d, 1H), 7.6 (m, 2H); LCMS: m/z 388 (M+1)$^+$.

Method 2

{(2S)-2-(3,4-Dichlorophenyl)-4-[3-(1-oxidothiomorpholin-4-yl)azetidin-1-yl]butyl}methylamine diacetate

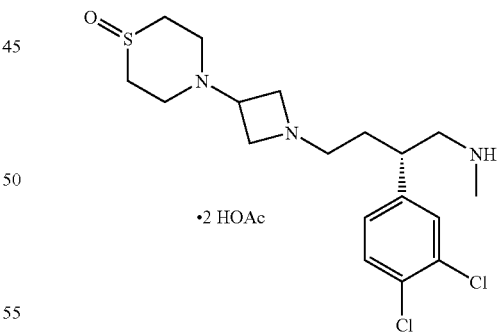

[(2S)-2-(3,4-Dichlorophenyl)-4-(3-thiomorpholin-4-ylazetidin-1-yl)butyl]methylamine hydrochloride (see Method 1; 270 mg, 0.54 mmol) was dissolved in acetic acid and to the resultant solution was added hydrogen peroxide (0.05 mL of 35% aqueous solution, 0.54 mmol). The mixture was stirred at room temperature for 2.5 h and the solvent was removed by evaporation. The residue was dissolved in ethanol (50 mL) and to the resultant solution was added MP-Carbonate resin (0.86 g of 3.18 mmol/g polymer-bound resin). The mixture was stirred for 30 min and then filtered whereupon the solvent was removed by evaporation. The product was purified by reversed phase chromatography using a mixture of acetonitrile and 0.1 M ammonium acetate aq. There was obtained 140 mg (49%) of {(2S)-2-(3,4-Dichlorophenyl)-4-[3-(1-oxidothiomorpholin-4-yl)azetidin-1-yl]butyl}methylamine diacetate. ¹H NMR (400 MHz, CDCl₃): 1.6-1.8 (m, 2H), 1.9 (s, 6H), 2.3-2.4 (m, 1H), 2.4-2.5 (m, 7H), 2.7-3.0 (m, 10H), 3.1 (m, 1H), 3.6 (m, 2H), 7.0 (dd, 1H), 7.2 (d, 1H), 7.3 (d, 1H), 8.2 (s, 2H); LCMS: m/z 404 (M+1)⁺.

Method 3

2-(4-Fluorophenyl)-4-(3-thiomorpholin-4-ylazetidin-1-yl)butyl]methylamine hydrochloride

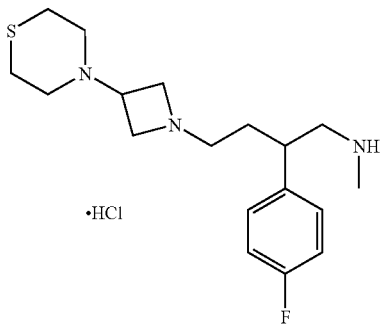

(a) tert-Butyl [2-(4-fluorophenyl)pent-4-en-1-yl]methylcarbamate

[2-(4-fluorophenyl)pent-4-en-1-yl]methylamine (see Method 17b; 11.2 g, 190 mmol) was dissolved in THF (350 mL) and to the solution was added triethylamine (8.7 ml, 100 mmol). The mixture was cooled by an external ice-bath and di-tert-butyldicarbonate (15 g, 218 mmol) was added. The ice-bath was removed and the reaction mixture was allowed to reach room temperature and then stirred overnight. Ether was added and the mixture was washed with water. The organic layer was dried (MgSO₄) and the solvent removed by evaporation. There was obtained 16.5g (29%) of tert-butyl [2-(4-fluorophenyl)pent-4-en-1-yl]methylcarbamate as a yellow solid. ¹H NMR (400 MHz, CDCl₃): 1.4 (s, 9H), 2.2-2.4 (m, 2H), 2.5-2.7 (cm, 3H), 2.8-3.8 (cm, 3H), 4.8-5.0 (cm, 2H), 5.5-5.7 (m, 1H), 6.9 (t, 2H), 7.1 (b, 2H).

(b) 1-[(tert-Butoxycarbonyl)(methyl)amino]-1,2,3-trideoxy-2-(4-fluorophenyl)pentitol tert-Butyl [2-(4-fluorophenyl)pent-4-en-1-yl]methylcarbamate (17.0 g, 57.9 mmol) was dissolved in a mixture of acetone, t-butanol and water (190 mL, 2:1:1). OsO₄ (3 ml, 2.5% t-butanol solution) was added at room temperature and after stirring for 10 minutes, NMO (27.1 g, 231 mmol) was added. The mixture was stirred overnight and then the reaction mixture was quenched by adding an aqueous solution of 20% sodium bisulfite. The mixture was stirred for 15 min and then diluted with water. The solution was extracted with CH₂Cl₂ and the organic extract was washed with brine, dried and concentrated on a rotavapor. There was obtained 19.4 g (100%) of crude 1-[(tert-butoxycarbonyl)(methyl)amino]-1,2,3-trideoxy-2-(4-fluorophenyl)pentitol as an oil. ¹H NMR (400 MHz, CDCl₃): 1.3 (s, 9H), 1.4-1.8 (cm, 2H), 2.0-3.6 (cm, 11H), 6.9 (t, 2H), 7.1 (b, 2H).

(c) tert-Butyl [2-(4-fluorophenyl)-4-oxobutyl]methylcarbamate

1-[(tert-butoxycarbonyl)(methyl)amino]-1,2,3-trideoxy-2-(4-fluorophenyl)pentitol (19.4 g, 59.2 mmo) was dissolved in a mixture of THF and water (3:1) and to the solution was added NaIO₄ (17.7 g, 82.9 mmol). After stirring for 6 h the reaction mixture was diluted with water and the mixture was extracted with ethyl acetate. The organic extract was washed with brine, dried and concentrated on a rotavapor. There was obtained tert-butyl [2-(4-fluorophenyl)-4-oxobutyl]methylcarbamate as a yellow oil. ¹³C NMR (100 MHz, CDCl₃): 28.4 (s), 35.1 (d), 38 (m), 47.3 (d), 54.6 (d), 79.8 (s), 115.7 (d), 129.4 (d), 137.2 (s), 155.8 (m), 160.7 (s), 163.2 (s), 200.6 (d).

(d) tert-Butyl [2-(4-fluorophenyl)-4-(3-thiomorpholin-4-ylazetidin-1-yl)butyl]methylcarbamate tert-Butyl [2-(4-fluorophenyl)-4-oxobutyl]methylcarbamate (0.50 g, 1.7 mmol) and 4-azetidin-3-ylthiomorpholine dihydrochloride (0.45 g, 2.0 mmol) were dissolved in methanol (30 mL). A methanolic solution (15 mL) of sodium cyano borohydride (0.71 g, 11.2 mmol) and zinc chloride (0.77 g, 5.6 mmol) was added and the mixture stirred for 1 h at room temperature. The solvent was removed by evaporation and the residue was partitioned between a saturated solution of NaHCO₃ aq and ethyl acetate. The organic solution was separated and the solvent was evaporated. The product was purified by reversed phase chromatography using a mixture of acetonitrile and 0.1 M ammonium acetate aq. There was obtained 350 mg (41%) of tert-butyl [2-(4-fluorophenyl)-4-(3-thiomorpholinyl-4-azetidin-1-yl)butyl]methylcarbamate as a pale yellow oil. ¹H NMR (500 MHz, CDCl₃): 1.3 (s, 9H), 1.6-1.7 (m, 2H), 2.0 (s, 1H), 2.3-2.7 (m, 12H), 2.8-3.6 (m, 6H), 3.6-3.7 (m, 2H), 6.9-7.1 (m, 4H), 10.2-10.4 (b, 1H); LCMS: m/z 438 (M+1)⁺.

(e) 2-(4-Fluorophenyl)-4-(3-thiomorpholin-4-ylazetidin-1-yl)butyl]methylamine hydrochloride tert-Butyl [2-(4-fluorophenyl)-4-(3-thiomorpholin-4-ylazetidin-1-yl)butyl]methylcarbamate (0.27 g, 0.62 mmol) was dissolved in a mixture of HCl and dioxane (4M HCl in dioxane). The solution was stirred overnight at room temperature and then the volatiles were removed by evaporation. There was obtained 0.26 g (100%) of 2-(4-fluorophenyl)-4-(3-thiomorpholin-4-ylazetidin-1-yl)butyl]methylamine hydrochloride as a solid. ¹H NMR (400 MHz, CD₃OD): 1.8-2.1 (2H), 2.7 (s, 3H), 2.9-4.6 (m, 18H), 7.2 (t, 2H), 7.4 (m, 2H); LCMS: m/z 338 (M+1)⁺.

Method 4

[(2S)-2-(4-Fluorophenyl)-4-(3-morpholin-4-ylazetidin-1-yl)butyl]methylamine dihydrochloride

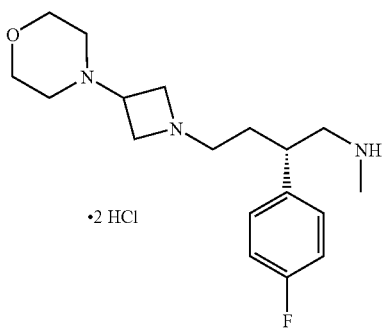

(a) tert-Butyl [(2S)-2-(4-fluorophenyl)pent-4-en-1-yl]methylcarbamate

[(2S)-2-(4-fluorophenyl)pent-4-en-1-yl]methylamine (see Bioorg. Med. Chem. Lett; 2001; 265-270; 1.19 g, 6.16 mmol) was dissolved in THF (50 mL) and to the solution was added triethylamine (0.69 g, 6.7 mmol). The mixture was cooled by an external ice-bath and then di-tert-butyldicarbonate (1.6 g, 7.4 mmol) was added. The ice-bath was removed and the reaction mixture was allowed to reach room temperature and then stirred for 5 h. Ether was added and the mixture was washed twice with water. The organic layer was dried (MgSO$_4$) and the solvent removed by evaporation. There was obtained 2 g (100%) of tert-butyl [(2S)-2-(4-fluorophenyl)pent-4-en-1-yl]methylcarbamate as a solid. $^1$H NMR (400 MHz, CDCl$_3$): 1.4 (s, 9H), 2.3-2.4 (m, 2H), 2.8-3.6 (cm, 6H), 4.9-5.0 (cm, 2H), 5.6-5.7 (m, 1H), 7.0 (m, 2H), 7.1 (b, 2H).

(b) tert-Butyl [(2S)-2-(4-fluorophenyl)-4-oxobutyl]methylcarbamate tert-Butyl [(2S)-2-(4-fluorophenyl)pent-4-en-1-yl]methylcarbamate (1.8 g, 6.1 mmol) was dissolved in a mixture of acetone (32 mL), tert-butanol (16 mL) and water (8 mL). The solution was stirred at room temperature during addition of OsO$_4$ (0.64 mL of 2.5% in tert-butanol, 0.06 mmol) and 4-methylmorpholine N-oxide (3.2 g, 27 mmol). The mixture was stirred at room temperature for 4 h. A saturated aqueous solution of sodium bisulfite (60 mL) was added and the mixture stirred for 20 min and then diluted with water (100 mL). The solution was extracted twice with CH$_2$Cl$_2$ and the combined organic solutions were washed with brine. The solvent removed by evaporation and the residue (2.4 g) was dissolved in a mixture of THF (28 mL) and water (12 mL) whereupon sodium periodate (1.44 g, 6.7 mmol) was added. The solution was stirred at room temperature for 4.5 h and then diluted with water and brine. The mixture was extracted twice with CH$_2$Cl$_2$ and the combined organic solutions were dried over MgSO$_4$. The solvent was removed by evaporation and there was obtained 1.58 g (87%) of tert-butyl [(2S)-2-(4-fluorophenyl)-4-oxobutyl]methylcarbamate. $^1$H NMR (500 MHz, CDCl$_3$): 1.4 (s, 9H), 2.6-2.8 (m, 5H), 3.2-3.6 (cm, 3H), 7.0 (m, 2H), 7.1 (b, 2H), 9.7 (s, 1H).

(c) tert-Butyl [(2S)-2-(4-fluorophenyl)-4-(3-morpholin-4-ylazetidin-1-yl)butyl]methylcarbamate tert-Butyl [(2S)-2-(4-fluorophenyl)-4-oxobutyl]methylcarbamate (1.57 g, 5.3 mmol) and 4-azetidin-3-ylmorpholine (0.83 g, 5.8 mmol) were dissolved in CH$_2$Cl$_2$ (60 mL) together with DIPEA (1.4 g, 10.6 mmol). The mixture was stirred for 20 min and then sodium triacetoxyborohydride (1.6 g, 7.4 mmol) was added. The mixture was stirred at room temperature for 6 h and then the solvent was removed by evaporation. The residue was partitioned between an aqueous solution of NaHCO$_3$ and ethyl acetate. The aqueous phase was extracted with ethyl acetate and the organic solution was dried over MgSO$_4$ and then removed by evaporation. The product was chromatographed on a silica gel using a mixture of methanol and CH$_2$Cl$_2$ (5%-20% methanol) and there was obtained 440 mg (20%) tert-butyl [(2S)-2-(4-fluorophenyl)-4-(3-morpholin-4ylazetidin-1-yl)butyl]methylcarbamate as an oil. $^1$H NMR (400 MHz, CDCl$_3$): 1.3 (s, 9H), 1.4-1.6 (m, 2H), 2.1-2.3 (b, 5H), 2.5-3.8 (cm, 16H), 6.9 (t, 2H), 7.0-7.1 (b, 2H); LCMS: m/z 422 (M+1)$^+$.

(d) [(2S)-2-(4-Fluorophenyl)-4-(3-morpholin-4-ylazetidin-1-yl)butyl]methylamine dihydrochloride tert-Butyl[(2S)-2-(4-fluorophenyl)-4-(3-morpholin-4-ylazetidin-1-yl)butyl]-methylcarbamate (0.44 g, 1.04 mmol) was dissolved in a HCl-saturated solution of ethyl acetate. The mixture was stirred at room temperature for 1 h and then the solvent was removed by evaporation. There was obtained 450 mg of [(2S)-2-(4-fluorophenyl)-4-(3-morpholin-4-ylazetidin-1-yl)butyl]methylamine dihydrochloride as a foam. $^1$H NMR (500 MHz, CD$_3$OD): 2.0 (m, 1H), 2.2 (m, 1H), 2.7 (s, 3H), 3.0-5.0 (cm, 18H), 7.2 (t, 2H), 7.5 (t, 2H); LCMS: m/z 322 (M+1)$^+$.

Method 5

1-{1-[3-(4-Fluorophenyl)-4-(methylamino)butyl]azetidin-3-yl}piperidin-4-ol dihydrochloride

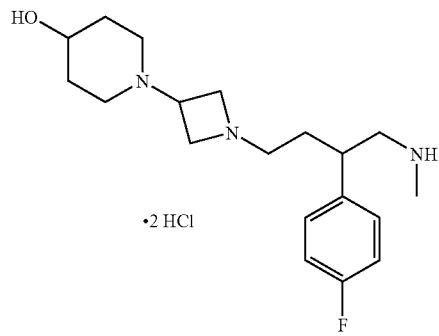

(a) tert-Butyl {2-(4-fluorophenyl)-4-[3-(4-hydroxypiperidin-1-yl)azetidin-1-yl]butyl}methylcarbamate The compound was synthesized in an analogous way to that of Method 3d but using 1-azetidin-3-ylpiperidin-4-ol dihydrochloride (see Meth 15) rather than 4-azetidin-3-ylthiomorpholine dihydrochloride (yield, 69%). $^1$H NMR (400 MHz, CDCl$_3$): 1.4 (s, 9H), 1.4-3.8 (cm, 25H), 7.0 (t, 2H), 7.0-7.2 (b, 2H), LCMS: m/z 436 (M+1)$^+$.

(b) 1-{1-[3-(4-Fluorophenyl)-4-(methylamino)butyl]azetidin-3-yl}piperidin-4-ol dihydrochloride The compound was synthesized in an analogous way to that of Method 3e but using 1 tert-butyl {2-(4-fluorophenyl)-4-[3-(4hydroxypiperidin-1-yl)azetidin-1-yl]butyl}-methylcarbamate rather than tert-butyl [2-(4fluorophenyl)-4-(3-thiomorpholin-4-ylazetidin-1-yl)butyl]methylcarbamate (yield, 98%). 1H NMR (400 MHz, CD$_3$OD): 1.8-2.2 (b, 6H), 2.7 (s, 3H), 3.0-4.8 (m, 15H), 7.0-7.2 (m, 2H), 7.3-7.4 (m, 2H). LCMS: m/z 336 (M+1)$^+$.

Method 6

[4-[3-(1,4-Dioxa-8-azaspiro[4.5]dec-8-yl)azetidin-1-yl]-2-(4-fluorophenyl)butyl]methylamine triflate

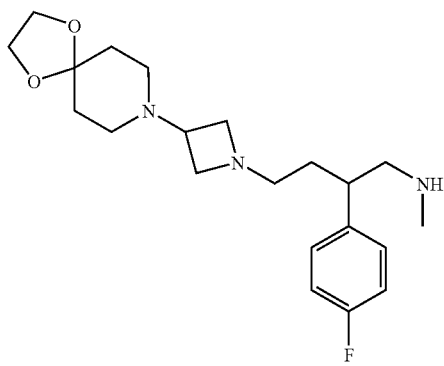

(a) tert-Butyl [4-[3-(1,4-dioxa-8-azaspiro[4.5]dec-8-yl)azetidin-1-yl]-2-(4-fluorophenyl)butyl]methylcarbamate The compound was synthesized in an analogous way to that of Method 3d but using 8-azetidin-3-yl-1,4-dioxa-8-azaspiro[4.5]decane hydrochloride (see Meth 13) rather than 4-azetidin-3-ylthiomorpholine dihydrochloride (yield, 70%). $^1$H NMR (400 MHz, CDCl$_3$): 1.4 (s, 9H), 1.4-3.6 (cm, 25H), 3.9-4.0 (m, 2H), 6.9-7.0 (t, 2H), 7.1-7.2 (b, 2H), LCMS: m/z 478 (M+1)$^+$.

(b) [4-[3-(1,4-Dioxa-8-azaspiro[4.5]dec-8-yl)azetidin-1-yl]-2-(4-fluorophenyl)butyl]methylamine triflate The compound was synthesized in an analogous way to that of Method 3e but using tert-butyl {2-(4-fluorophenyl)-4-[3-(4-hydroxypiperidin-1-yl)azetidin-1-yl]butyl}methylcarbamate and trifluoroacetic acid rather than tert-butyl [2-(4-fluorophenyl)-4-(3-thiomorpholin-4-ylazetidin-1-yl)butyl]methylcarbamate and HCl (yield, 100%). LCMS: m/z 378 (M+1)$^+$.

Method 7

{(2S)-2-(3,4-Dichlorophenyl)-4-[3-(4-fluoropiperidin-1-yl)azetidin-1-yl]butyl}methylamine dihydrochloride

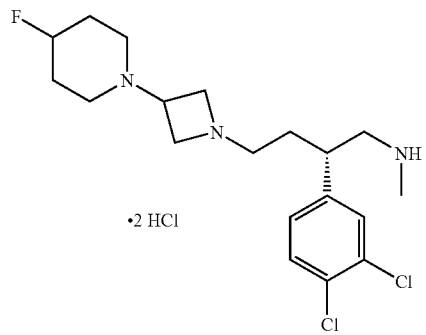

(a) tert-Butyl {(2S)-2-(3,4-dichlorophenyl)-4-[3-(4-fluoropiperidin-1-yl)azetidin-1-yl]butyl}methylcarbamate The compound was synthesized in an analogous way to that of Method 3d but using 1-azetidin-3-yl-4-fluoropiperidine dihydrochloride (see WO 97/27185) and tert-butyl [(2S)-2-(3,4-dichlorophenyl)-4-oxobutyl]methylcarbamate (see WO 95/05377) rather than 4-azetidin-3-ylthiomorpholine dihydrochloride and tert-butyl [2-(4-fluorophenyl)-4-oxobutyl]methylcarbamate (yield, 13%). $^1$H NMR (500 MHz, CDCl$_3$): 1.3 (s, 9H), 1.5-3.6 (cm, 23H), 4.6-4.8 (bd, 1H), 6.9-7.1 (dd, 1H), 7.2 (m, 1H), 7.4 (d, 1H), LCMS: m/z 489 (M+1)$^+$.

(b) {(2S)-2-(3,4-Dichlorophenyl)-4-[3-(4-fluoropiperidin-1-yl)azetidin-1-yl]butyl}methylamine dihydrochloride The compound was synthesized in an analogous way to that of Method 3e but using tert-butyl {(2S)-2-(3,4-dichlorophenyl)-4-[3-(4-fluoropiperidin-1-yl)azetidin-1-yl]butyl}methylcarbamate rather than tert-butyl [2-(4-fluorophenyl)-4-(3-thiomorpholin-4-ylazetidin-1-yl)butyl]methylcarbamate (yield, 100%). $^1$H NMR (500 MHz, CD$_3$OD): 1.9-2s 2.4 (m, 6H), 2.7 (s, 3H), 3.1-5.1 (cm, 15H), 7.4 (d, 1H), 7.7 (m, 2H), LCMS: m/z 389 (M+1)$^+$.

Method 8

1-{1-[(3S)-3-(3,4-Dichlorophenyl)-4-(methylamino)butyl]azetidin-3-yl}piperidin-4-ol dihydrochloride

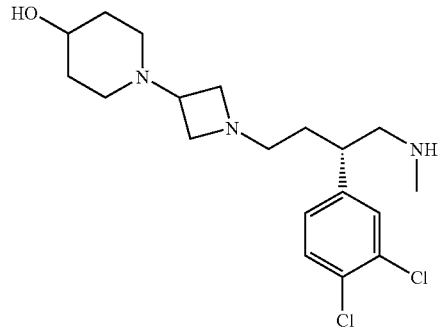

(a) tert-Butyl {(2S)-2-(3,4-dichlorophenyl)-4-[3-(4-hydroxypiperidin-1-yl)azetidin-1-yl]butyl}methylcarbamate The compound was synthesized in an analogous way to that of Method 3d but using 1-azetidin-3-ylpiperidin-4-ol dihydrochloride (see Meth 15) and tert-butyl [(2S)-2-(3,4-dichlorophenyl)-4-oxobutyl]methylcarbamate (see WO 95/05377) rather than 4-azetidin-3-ylthiomorpholine dihydrochloride and tert-butyl [2-(4-fluorophenyl)-4-oxobutyl]methylcarbamate (yield, 35%). $^1$H NMR (500 MHz, CDCl$_3$): 1.3 (m, 2H), 1.4 (s, 9H), 1.5-3.8 (cm, 23H), 7.0 (dd, 1H), 7.2-7.4 (m, 2H), LCMS: m/z 487 (M+1)$^+$.

(b) 1-{1-[(3S)-3-(3,4-Dichlorophenyl)-4-(methylamino)butyl]azetidin-3-yl}piperidin-4-ol dihydrochloride The compound was synthesized in an analogous way to that of Method 3e but using tert-butyl {(2S)-2-(3,4-dichlorophenyl)-4-[3-(4-hydroxypiperidin-1-yl)azetidin-1-yl]butyl}methylcarbamate rather than tert-butyl [2-(4-fluorophenyl)-4-(3-thiomorpholin-4-ylazetidin-1-yl)butyl]methylcarbamate (yield, 100%). $^1$H NMR (500 MHz, CD$_3$OD): 1.8-2.2 (m, 6H), 2.7 (s, 3H), 3.2-4.8 (cm, 17H), 7.4 (dd, 1H), 7.6-7.7 (m, 2H), LCMS: m/z 387 (M+1)$^+$.

Method 9

5-Cyano-1-benzothiophene-7-carboxylic acid

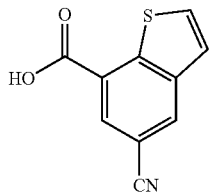

(a) Ethyl 5-cyano-1-benzothiophene-7-carboxylate

N-[2-cyano-3-(dimethylamino)prop-2-en-1-ylidene]-N-methylmethanaminium perchlorate (see Collect. Czech. Chem. Commun.; 32; 5; 1967; 1704; 5.84 g, 23.2 mmol) and ethyl 2-thienylacetate (3.95 g, 23.2 mmol) were mixed with quinoline (117 mL) at 0° C. Sodium ethoxide (1.97 g, 27.9 mmol) was added and the mixture was stirred at 0° C. for 30 min and then at room temperature for 15 min. The reaction mixture was heated to 75° C. under nitrogen for 5 h and then cooled to 0° C. Hydrochloric acid (200 mL of 2 M aqueous solution) was added and the mixture extracted thrice with chloroform. The organic solution was washed with brine and then dried over Na$_2$SO$_4$. The solvent was removed by evaporation and the residue flash chromatographed on silica gel (hexane-ethyl acetate, 8:1). There was obtained 2.3 g (43%) of ethyl 5-cyano-1-benzothiophene-7-carboxylate as a pale yellow solid. $^1$H NMR (300 MHz, CDCl$_3$): 1.5 (t, 3H), 4.5 (qt, 2H), 7.5 (d, 1H), 7.7 (d, 1H), 8.3 (m, 2H).

(b) 5-Cyano-1-benzothiophene-7-carboxylic acid

Ethyl 5-cyano-1-benzothiophene-7-carboxylate (5.6 g, 24.3 mmol) was dissolved THF (96 mL) and to the resultant solution was added an aqueous solution of NaOH (1.07 g of NaOH in 14 mL of water, 26.7 mmol) at 0° C. The mixture was stirred at room temperature overnight and then most of the solvent was removed by evaporation. The residue was dissolved in an aqueous solution of NaOH (0.1 M). The solution was washed thrice with chloroform, acidified with 2M HCl and then extracted with ethyl acetate. The organic solution was separated and the solvent was evaporated. The residue was flash chromatographed on silica gel (CH$_2$Cl$_2$-MeOH—NH$_4$OH, 8:2:0.5). There was obtained 4.3 g (85%) of 5-cyano-1-benzothiophene-7-carboxylic acid as a tan solid. $^1$H NMR (500 MHz, DMSO-d$_6$): 7.7 (d, 1H), 8.1 (d, 2H), 8.3 (d, 1H), 8.7 (s, 1H), 14 (b, 1H); LCMS: m/z 202 (M−1)$^−$.

Method 10

7-Chloro-2,3-dihydro-1,4-benzodioxine-5-carboxylic acid

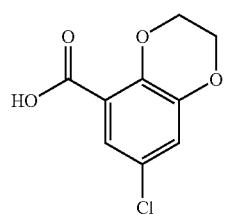

(a) 5-Chloro-2,3-dihydroxybenzaldehyde

5-Chloro-2-hydroxy-3-methoxy-benzaldehyde (see J. Org. Chem. 56; 1991; 5451; 20.0 g, 107 mmol) was suspended in hydrobromic acid (100 mL of 47% in water). The mixture was refluxed for 6 h and then cooled to room temperature before dilution with water (300 mL). The formed precipitate was collected by filtration and then washed with water. After air drying, the solid material was purified by soaking with CH$_2$Cl$_2$ (4×150 mL). There was obtained 6.0 g (32%) of 5-chloro-2,3-dihydroxybenzaldehyde as a solid. $^1$H NMR (300 MHz, CDCl$_3$): 5.7 (s, 1H), 7.1 (d, 1H), 7.2 (d, 1H), 9.8 (s, 1H), 11.0 (s, 1H).

(b) 7-Chloro-2,3-dihydro-1,4-benzodioxine-5-carbaldehyde

5-Chloro-2,3-dihydroxybenzaldehyde (6.0 g, 34.7 mmol) was dissolved in DMF (100 mL) and to the solution were added 1,2-dibromoethane (8.0 g, 42.5 mmol) and potassium carbonate (10.0 g, 70 mmol). The mixture was stirred at 100° C. for one hour, cooled to room temperature and then diluted with water (200 mL). After extraction twice with ethyl acetate (200 mL) the combined organic solutions were washed with brine and then dried over Na$_2$SO$_4$. The solvent was removed by evaporation and the solid residue treated with methanol. After filtration and drying there was obtained 6.5 g (94%) of 7-chloro-2,3-dihydro-1,4-benzodioxine-5-carbaldehyde. $^1$H NMR (300 MHz, CDCl$_3$): 4.3-4.4 (m, 4H), 7.1 (d, 1H), 7.3 (d, 1H), 10.3 (s, 1H).

(c) 7-Chloro-2,3-dihydro-1,4-benzodioxine-5-carboxylic acid

7-Chloro-2,3-dihydro-1,4-benzodioxine-5-carbaldehyde (6.25 g, 31.4 mmol) was dissolved in acetone (150 mL) and the solution was then cooled to 5° C. A solution of $CrO_3$ in sulfuric acid (4 M in 4 M $H_2SO_4$, 12.5 mL, 50 mmol) was added dropwise over 2 min and the mixture was refluxed for 30 min. Water (150 mL) was added and then most of the acetone was removed by evaporation. The mixture was extracted with ether (150 mL) and the organic solution was then extracted with a solution of NaOH (0.5 M, 150 mL). The aqueous solution was acidified with 2 M hydrochloric acid and then extracted with ether (150 mL). The organic solution was washed with brine and dried over $Na_2SO_4$. The solvent was removed by evaporation and the residue treated with $CH_2Cl_2$. After filtration and drying there was obtained 5.2 g (77%) of 7-chloro-2,3-dihydro-1,4-benzodioxine-5-carboxylic acid. $^1H$ NMR (400 MHz, acetone-$d_6$): 4.3-4.4 (m, 4H), 7.1 (d, 1H), 7.3 (d, 1H), 11-12 (b, 1H).

Method 11

3-Cyano-1-naphthoyl chloride

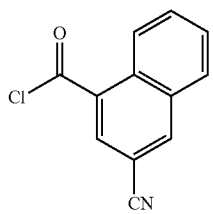

3-Cyano-1-naphthoic acid (see Bioorg. Med. Chem. Lett. 2001, 2769; 1.1 g, 5.6 mmol) was slurried in $CH_2Cl_2$ (10 mL) and then oxalyl chloride was added with stirring. A drop of DMF was added and the mixture stirred at room temperature overnight under nitrogen. The solvent was removed by evaporation and there was obtained 1.2 g (100%) of 3-cyano-1-naphthoyl chloride as a pale yellow solid. $^1H$ NMR (300 MHz, CDCl$_3$): 7.7-7.8 (m, 1H), 7.8-7.9 (m, 1H), 8.0-8.1 (m, 1H), 8.5 (s, 1H), 8.7 (s, 1H), 8.8 (d, 1H).

Method 12

1-Azetidin-3-ylpyrrolidin-3-ol dihydrochloride

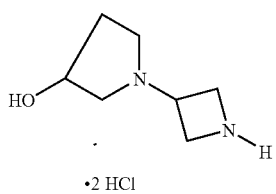

·2 HCl

(a) 1-[1-(Diphenylmethyl)azetidin-3-yl]pyrrolidin-3-ol 1-(Diphenylmethyl)azetidin-3-yl methanesulfonate (see J. Org. Chem.; 56; 1991; 6729; 310 mg, 0.98 mmol) was dissolved in acetonitrile (3.5 mL). Pyrrolidin-3-ol (104 mg, 1.2 mmol) and triethylamine (124 mg, 1.2 mmol) were added and the mixture was subjected to microwave single node heating for 10 minutes. The solvent was removed by evaporation and the residue was dissolved in ethyl acetate. The solution was washed with water, dried over MgSO$_4$ and then the solvent was evaporated. There was obtained 280 mg (93%) of 1-[1-(diphenylmethyl)azetidin-3-yl]pyrrolidin-3-ol as an oil. $^1H$ NMR (300 MHz, CDCl$_3$): 1.6-1.8 (m, 1H), 2.1-2.3 (m, 2H), 2.4-2.6 (m, 2H), 2.6-2.8 (m, 1H), 2.9-3.0 (m, 2H), 3.1-3.2 (m, 1H), 3.3-3.4 (m, 2H), 4.3 (m, 1H), 4.4 (s, 1H), 7.1-7.5 (m, 10H); LCMS: m/z 309 (M+1)$^+$.

(b) 1-Azetidin-3-ylpyrrolidin-3-ol

1-[1-(Diphenylmethyl)azetidin-3-yl]pyrrolidin-3-ol (310 mg, 0.98 mmol) was dissolved in ethanol (20 mL). A mixture of palladium hydroxide on carbon and palladium on activated carbon was added and to the resultant mixture was then added concentrated HCl (0.1 mL) dropwise. The mixture was stirred under hydrogen (5 atm) at room temperature overnight and then the catalyst was filtered off by means of Celite®. The solvent was removed by evaporation and the residue triturated with $CH_2Cl_2$. There was obtained 154 mg (79%) of 1-azetidin-3-ylpyrrolidin-3-ol dihydrochloride as a solid. $^{13}C$ NMR (75 MHz, D$_2$O): 48.8 (s), 65.1 (s), 67.7 (s), 70.9 (s), 76.2 (s), 85.7 (s); LCMS: m/z 143 (M+1)$^+$.

Method 13

8-Azetidin-3-yl-1,4-dioxa-8-azaspiro[4.5]decane hydrochloride

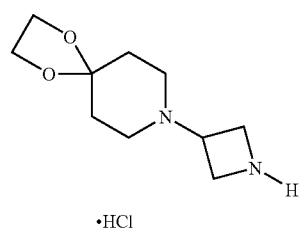

·HCl

(a) 8-[1-(Diphenylmethyl)azetidin-3-yl]-1,4-dioxa-8-azaspiro[4.5]decane

The compound was synthesized in an analogous way to Method 12a but using 1,4-dioxa-8-azaspiro[4.5]decane as starting material rather than pyrrolidin-3-ol (yield, 72%). $^1H$ NMR (400 MHz, CDCl$_3$): 1.6-1.8 (m, 4H), 2.3-2.3 (m, 4H), 2.9 (t, 2H), 3.0 (qn, 1H), 3.4 (t, 2H), 3.9 (s, 4H), 4.4 (s, 1H), 7.1-7.5 (m, 10H); LCMS: m/z 365 (M+)$^+$.

(b) 8-Azetidin-3-yl-1,4-dioxa-8-azaspiro[4.5]decane hydrochloride

8-[1-(Diphenylmethyl)azetidin-3-yl]-1,4-dioxa-8-azaspiro[4.5]decane (0.5 g, 1.4 mmol) was dissolved in dry CH$_2$Cl$_2$ under nitrogen and to the resultant solution was added 1-chloroethyl chloroformate (0.45 mL, 4.1 mmol) at 0° C. The mixture was stirred for 1.5 h and then methanol was added. The solution was heated to reflux for 20 min and then the solvent was removed by evaporation. The residue was triturated with acetone and the precipitate was then recrystal-

Method 14

Thiomorpholine 1,1-dioxide dihydrochloride

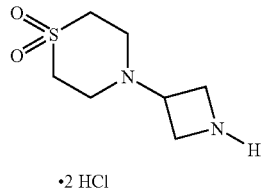

•2 HCl

(a) 4-[1-(Diphenylmethyl)azetidin-3-yl]thiomorpholine 1,1-dioxide

The compound was synthesized in an analogous way to that of Method 12a but using thiomorpholine 1,1-dioxide (see J. Chem. Soc. 1949, 3433) rather than pyrrolidin-3-ol (yield, 19%). $^1$H NMR (400 MHz, CDCl$_3$): 2.7-2.8 (m, 4H), 2.8-2.9 (m, 2H), 3.0-3.1 (m, 4H), 3.2 (qn, 1H), 3.4 (m, 2H), 4.4 (s, 1H), 7.1-7.4 (m, 10H); LCMS: m/z 357 (M+1)$^+$.

(b) Thiomorpholine 1,1-dioxide dihydrochloride

The compound was synthesized in an analogous way to that of Method 12b but using 4-[1-(diphenylmethyl)azetidin-3-yl]thiomorpholine 1,1-dioxide rather than 1-[1-(diphenylmethyl)azetidin-3-yl]pyrrolidin-3-ol (yield, 89%). $^1$H NMR (400 MHz, D$_2$O): 3.2-3.4 (b, 4H), 3.4-3.5 (m, 4H), 4.2 (m, 1H), 4.2-4.4 (4H).

Method 15

1-Azetidin-3-ylpiperidin-4-ol dihydrochloride

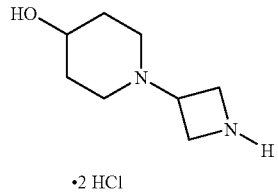

•2 HCl

(a) 1-[1-(Diphenylmethyl)azetidin-3-yl]piperidin-4-ol

The compound was synthesized in an analogous way to that of Method 12a but using piperidin-4-ol rather than pyrrolidin-3-ol (yield, 73%). $^1$H NMR (400 MHz, CDCl$_3$): 1.5-1.6 (m, 2H), 1.8 (m, 2H), 2.0 (m, 2H), 2.6 (m, 2H), 2.8-3.0 (m, 3H), 3.4 (m, 2H), 3.6-3.7 (m, 1H), 4.4 (s, 1H), 7.1-7.5 (m, 10H); LCMS: m/z 323 (M+1)$^+$.

(b) 1-Azetidin-3-ylpiperidin-4-ol dihydrochloride

The compound was synthesized in an analogous way to that of Method 12b but using 1-[1-(diphenylmethyl)azetidin-3-yl]piperidin-4-ol rather than 1-[1-(diphenylmethyl)azetidin-3-yl]pyrrolidin-3-ol (yield, 89%). $^1$H NMR (400 MHz, DMSO-d6): 1.6-5.0 (cm, 13H), 9.0-9.4 (b, 1H), 9.8-10.2 (b, 1H), 12.0-12.8 (b, 1H).

Method 16

1-[(3s)-4-[(3-Cyano-1-naphthoyl)(methyl)amino]-3-(3,4-dichlorophenyl)butyl]azetidin-3-yl methanesulfonate

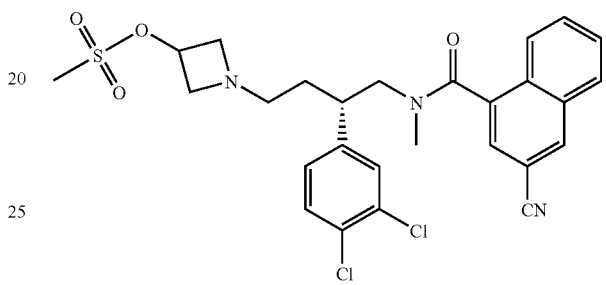

(a) 3-Cyano-N-[(2S)-2-(3,4-dichlorophenyl)-4-(3-hydroxyazetidin-1-yl)butyl]-N-methyl-1-naphthamide 3-Cyano-N-[(2S)-2-(3,4-dichlorophenyl)-4-oxobutyl]-N-methyl-1-naphthamide (see WO 00/02859; 1.0 g, 2.3 mmol) was dissolved in CH$_2$Cl$_2$ (10 mL) and to the resultant solution were added azetidin-3-ol hydrochloride (0.24 g, 2.2 mmol) and triethylamine (0.30 mL, 2.2 mmol). After stirring for 40 min, sodium triacetoxyborohydride (0.65 g, 3.1 mmol) was added and the solution was stirred at room temperature for 3 h. The solvent was removed by evaporation and the residue was partitioned between saturated aqueous NaHCO$_3$ solution and ethyl acetate. The solvent was removed by evaporation and the residue was dissolved in hydrochloric acid (1M). The solution was washed with CH$_2$Cl$_2$, alkalised with aqueous NaOH (2M) and then extracted with CH$_2$Cl$_2$. The solvent was removed by evaporation and there was obtained 0.85 g (80%) of 3-cyano-N-[(2S)-2-(3,4-dichlorophenyl)-4-(3-hydroxyazetidin-1-yl)butyl]-N-methyl-1-naphthamide as a white solid. $^1$H NMR (400 MHz, DMSO-d$_6$): 0.8-4.4 (cm, 16H), 6.4-8.2 (cm, 8H), 8.6 (d, 1H); LCMS: m/z 482 (M+1)$^+$.

(b) 1-[(3S)-4-[(3-Cyano-1-naphthoyl)(methyl)amino]-3-(3,4-dichlorophenyl)butyl]azetidin-3-yl methanesulfonate 3-Cyano-N-[(2S)-2-(3,4-dichlorophenyl)-4-(3-hydroxyazetidin-1-yl)butyl]-N-methyl-1-naphthamide (0.20 g, 0.41 mmol) was dissolved in CH$_2$Cl$_2$ and to the resultant solution was added triethylamine (0.17 mL, 0.41 mmol). The mixture was cooled to 0° C. before careful addition of methanesulfonyl chloride (0.03 mL, 0.41 mmol). The mixture was stirred with cooling for 30 min and then at room temperature for 1 h. The reaction mixture was diluted with CH$_2$Cl$_2$ and then washed with hydrochloric acid (1M), saturated NaHCO$_3$ and then with brine. The organic solution was dried over MgSO₄ and the solvent removed by evaporation. There was obtained 0.21 g (92%) of 1-[(3S)-4-[(3-cyano-1-naphthoyl)(methyl)amino]-3-(3,4-dichlorophenyl)butyl]azetidin-3-yl methanesulfonate as a solid. LCMS: m/z 560 (M+)⁺.

Method 17

3-Cyano-N-[2-(4-fluorophenyl)-4-oxobutyl]-N-methyl-1-naphthamide

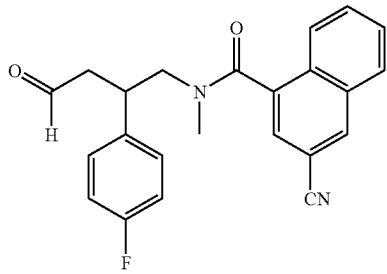

(a) 2-(4-Fluorophenyl)-N-methylpent-4-enamide 2-(4-Fluorophenyl)pent-4-enoic acid (Bioorg. Med. Chem. Lett. 2000, 1893; 4.20 g, 21.6 mmol) was dissolved in CH₂Cl₂ (75 mL) and to the resultant solution was added TBTU (7.29 g, 22.7 mmol). The mixture was stirred at RT for 15 min and then methylamine (11.9 mL of 2M THF solution, 23.8 mmol) and DIPEA (11.2 g, 86.5 mmol) were added. The reaction mixture was stirred at room temperature for 3 h, subsequently diluted with CH₂Cl₂ (50 mL) and then washed several times with water. The solvent was removed by evaporation and the residue flash chromatographed on silica gel (heptane-ethyl acetate, 1:1). There was obtained 3.5 g (78%) of 2-(4-fluorophenyl)-N-methylpent-4-enamide as an oil, which shortly after crystallized. ¹H NMR (400 MHz, CDCl₃): 2.5 (qn, 1H), 2.7 (d, 3H), 2.9 (qn, 1H), 3.4 (t, 1H), 4.9-5.1 (m, 2H), 5.6-5.8 (m, 1H), 6.0-6.2 (b, 1H), 7.0 (m, 2H), 7.3 (m, 2H).

(b) [2-(4-Fluorophenyl)pent-4-en-1-yl]methylamine

Lithium aluminium hydride (0.11 g, 2.9 mmol) was slurried in ether (15 mL) under nitrogen with stirring. A solution of 2-(4-fluorophenyl)-N-methylpent-4-enamide (0.20 g in 5 mL of ether, 0.97 mmol) was added carefully and the mixture was then stirred at room temperature overnight. Water (0.11 mL) was added dropwise followed by a solution of NaOH (0.11 mL of a 15% aqueous solution) and then water (0.33 mL) again. The mixture was stirred for 10 min and then filtered. The filter cake was washed with ether and the combined solutions were washed several times with water. The organic solution was dried over MgSO₄ and the solvent was removed by evaporation. There was obtained 0.16 g (86%) of [2-(4-fluorophenyl)pent-4-en-1-yl]methylamine as an oil. ¹H NMR (400 MHz, CDCl₃): 2.4-2.6 (m, 5H), 2.7-2.9 (m, 3H), 4.9-5.0 (m, 2H), 5.6-5.8 (m, 1H), 7.0 (m, 2H), 7.1 (m, 2H); LCMS: m/z 194 (M+1)⁺.

(c) 3-Cyano-N-[2-(4-fluorophenyl)pent-4-en-1-yl]-N-methyl-1-naphthamide

[2-(4-Fluorophenyl)pent-4-en-1-yl]methylamine (1.0 g, 5.2 mmol) was dissolved in CH₂Cl₂ and stirred at 0° C. during addition of DIPEA (1.5 g, 11.4 mmol) and 3-cyano-1-naphthoyl chloride (Method 11; 1.1 g, 5.17 mmol). The mixture was stirred with cooling for a short while and then stirred at room temperature for 2 h. The mixture was washed twice with water, once with an aqueous solution of KHSO₄, and then with brine. The solvent was removed by evaporation and the residue flash chromatographed on silica gel (methanol-CH₂Cl₂, 5:95). There was obtained 1.55 g (80%) of 3-cyano-N-[2-(4-fluorophenyl)pent-4-en-1-yl]-N-methyl-1-naphthamide as an oil. ¹H NMR (400 MHz, CDCl₃): 2.1-4.9 (cm, 8H), 5.0-5.1 (m, 2H), 5.6-5.8 (m, 1H), 6.4-8.0 (cm, 9H), 8.2 (s, 1H).

(d) 3-Cyano-N-[2-(4-fluorophenyl)-4-oxobutyl]-N-methyl-1-naphthamide

3-Cyano-N-[2-(4-fluorophenyl)pent-4-en-1-yl]-N-methyl-1-naphthamide (1.5 g, 4.03 mmol) was dissolved in a mixture of acetone (30 mL), tert-butanol (15 mL) and water (7.5 mL) and stirred at room temperature during addition of OsO₄ (0.40 mL of 2.5% in tert-butanol, 0.04 mmol). 4-Methylmorpholine N-oxide (2.08 g, 17.8 mmol) was added and the mixture was stirred at room temperature overnight. A saturated aqueous solution of sodium bisulfite (15 mL) was added and the mixture stirred for 5 min and then concentrated. The residue was diluted with water (100 mL) and then extracted thrice with CH₂Cl₂. The combined organic solutions were washed with brine and the solvent removed by evaporation. The residue was dissolved in a mixture of THF (21 mL) and water (7 mL) whereupon sodium periodate (0.95 g, 4.43 mmol) was added. The solution was stirred at room temperature overnight and then diluted with water (150 mL) and brine (75 mL). The mixture was extracted thrice with ethyl acetate and the combined organic solutions were washed with water and then with brine. The solvent was removed by evaporation and the residue flash chromatographed on silica gel (ethyl acetate-heptane, 7:3). There was obtained 1.43 g (95%) of 3-cyano-N-[2-(4-fluorophenyl)-4-oxobutyl]-N-methyl-1-naphthamide as a colourless oil. ¹H NMR (400 MHz, CDCl₃): 2.4-4.4 (cm, 8H), 6.8-8.0 (cm, 9H), 8.2 (s, 1H), 9.8 (s, 1H).

Method 18

3-Cyano-N-[2-(4-cyanophenyl)-4-oxobutyl]-N-methyl-1-naphthamide

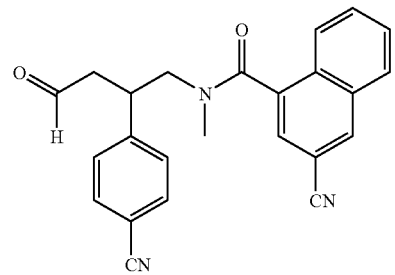

(a) {2-(4-Bromophenyl)-4-[(triisopropylsilyl)oxy]butyl}methylamine 3-(4-Bromophenyl)-4-(methylamino)butan-1-ol (see Chem. Pharm. Bull. 46, 1998, 242; 1.77 g, 6.86 mmol) was dissolved in CH$_2$Cl$_2$ (100 mL) at 0° C. under argon. Imidazole (1.22 g, 17.9 mmol) was added, the mixture stirred for 10 min and then triisopropylchlorosilan (3.16 g, 16.4 mmol) was added with cooling. The mixture was stirred at room temperature for 48 h and then washed twice with water (100 mL) and brine. The solvent was removed by evaporation and the residue flash chromatographed on silica gel (CH$_2$Cl$_2$-Methanol-NH$_4$OH, 15:1:0.1). There was obtained 2.17 g (75%) of {2-(4-bromophenyl)-4-[(triisopropylsilyl)oxy]butyl}methylamine as an oil. $^1$H NMR (300 MHz, CDCl$_3$): 0.9-1.1 (m, 21H), 1.6-1.9 (m, 2H), 2.4 (s, 3H), 2.7-2.8 (m, 2H), 3.0-3.1 (m, 1H), 3.4-3.6 (m, 2H), 7.1 (d, 2H), 7.4 (d, 2H).

(b) tert-Butyl {2-(4-bromophenyl)-4-[(triisopropylsilyl)oxy]butyl}methylcarbamate {2-(4-Bromophenyl)-4-[(triisopropylsilyl)oxy]butyl}methylamine (0.95 g, 2.3 mmol) and 4-dimethylaminopyridine (0.34 g, 2.8 mmol) were dissolved in dry CH$_2$Cl$_2$ (10 mL) under is nitrogen. Boc-anhydride (1.1 g, 5.1 mmol) was added at 0° C. and the mixture was stirred at room temperature for 48 h and then washed twice with brine. The solution was dried over Na$_2$SO$_4$ and the solvent was removed by evaporation. The residue was flash chromatographed on silica gel (hexane-ether, 40:1 to 8:1). There was obtained 1.66 g (73%) of tert-Butyl {2-(4-bromophenyl)-4-[(triisopropylsilyl)oxy]butyl}methylcarbamate as an oil. $^1$H NMR (300 MHz, CDCl$_3$): 0.9-1.1 (m, 21H), 1.4 (s, 9H), 1.7-1.9 (m, 2H), 2.7 (m, 3H), 3.2-3.6 (m, 5H), 7.0-7.1 (m, 2H), 7.3-7.4 (m, 2H).

(c) tert-Butyl {2-(4-cyanophenyl)-4-[(triisopropylsilyl)oxy]butyl}methylcarbamate tert-Butyl {2-(4-bromophenyl)-4-[(triisopropylsilyl)oxy]butyl}methylcarbamate (1.16 g, 2.25 mmol), tris(dibenzylideneacetone)dipalladium (0) (0.62 g, 0.68 mmol) and tri-o-tolylphosphine (1.03 g, 3.38 mmol) were mixed together with acetonitrile (3 mL) and DMF (3 mL) under argon. Zinc cyanide (0.16 g, 1.35 mmol) was added and the mixture was stirred at 81° C. for 24h and then concentrated. Ethyl acetate was added to the residue and the slurry was filtered through a micro filter. The solvent was removed by evaporation and the residue purified by flash chromatography (hexane-ether, 10:1). There was obtained 0.43 g, (41%) of tert-butyl {2-(4-cyanophenyl)-4-[(triisopropylsilyl)oxy]butyl}-methylcarbamate as a solid. 1H NMR (300 MHz, CDCl$_3$): 0.9-1.1 (m, 21H), 1.4 (s, 9H), 1.7-1.9 (m, 2H), 2.7 (m, 3H), 3.2-3.6 (m, 5H), 7.3-7.4 (m, 2H), 7.5-7.6 (m, 2H); MS: m/z 361 (M+1)$^+$.

(d) 4-{3-Hydroxy-1-[(methylamino)methyl]propyl}benzonitrile tert-Butyl {2-(4-cyanophenyl)-4-[(triisopropylsilyl)oxy]butyl}methylcarbamate (0.37 g) was dissolved in THF (8 mL) at 0° C. Hydrochloric acid (8 ml of 6M solution) was added and the mixture stirred overnight at room temperature. The volatiles were removed by evaporation and then removed azeotropically after the addition of methanol (5×50 mL). The residue was dissolved in water and the solution alkalised to pH 8-9 by the addition of Na$_2$CO$_3$ (s) and then extracted thrice with ethyl acetate (100 mL). The organic solution was dried over Na$_2$SO$_4$ and then the solvent was evaporated. The product was purified by flash chromatography (CH$_2$Cl$_2$-MeOH—NH$_4$OH, 9:1:0.1). There was obtained 0.10 g, 60%) of 4-{3-Hydroxy-1-[(methylamino)methyl]propyl}benzonitrile as a solid. $^1$H NMR (300 MHz, CDCl$_3$): 1.9-2.0 (m, 2H), 2.5 (s, 3H), 2.8-2.9 (m, 3H), 3.4-3.7 (m, 3H), 3.7 (m, 1H), 7.3 (d, 2H), 7.6 (d, 2H); LCMS: m/z 205 (M+1)$^+$.

(e) 3-Cyano-N-[2-(4-cyanophenyl)-4-hydroxybutyl]-N-methyl-1-naphthamide

4-{3-Hydroxy-1-[(methylamino)methyl]propyl}benzonitrile (0.55 g, 2.69 mmol) and DIPEA (0.77 g, 5.9 mmol) were dissolved in CH$_2$Cl$_2$ (5 mL). 3-Cyano-1-naphthoyl chloride (sse Method 11; 0.58 g, 2.69 mmol) was added in portions with stirring and cooling (external ice-bath). The mixture was stirred for 2 h with cooling and then diluted with CH$_2$Cl$_2$ (10 mL). The solution was washed twice with water, twice with a saturated aqueous KHSO$_4$ solution and then with brine. The solvent was removed by evaporation and the residue flash chromatographed on silica gel (CH$_2$Cl$_2$-MeOH, 9:1). There was obtained 0.70 g (67%) of 3-cyano-N-[2-(4-cyanophenyl)-4-hydroxybutyl]-N-methyl-1-naphthamide as a white solid. $^1$H NMR (400 MHz, CDCl$_3$): 1.4-2.5 (cm, 2H), 2.6 (s, 3H), 3.1-4.6 (cm, 6H), 6.4-7.8 (cm, 8H), 7.9 (d, 1H), 8.2 (s, 1H); LCMS: m/z 384 (M+1)$^+$.

(f) 3-Cyano-N-[2-(4-cyanophenyl)-4-oxobutyl]-N-methyl-1-naphthamide

3-Cyano-N-[2-(4-cyanophenyl)-4-hydroxybutyl]-N-methyl-1-naphthamide (0.70 g, 1.8 mmol) was dissolved in CH$_2$Cl$_2$ (15 mL) and to the resultant solution was added Dess Martin Periodinane (0.85 g, 2.0 mmol) in portions. The mixture was stirred at room temperature overnight and then sodium thiosulfate (1.9 g, 12 mmol), dissolved in saturated NaHCO$_3$ solution (30 mL), was added. The mixture was stirred vigorously for 2 h and then the organic solution was washed with brine and dried over Na$_2$SO$_4$. The solvent was removed by evaporation and the residue purified by flash chromatography (ethyl acetate-heptane, 4:1). There was obtained 0.50 g, (43%) of 3-cyano-N-[2-(4-cyanophenyl)-4-oxobutyl]-N-methyl-1-naphthamide as a white solid. $^1$H NMR (400 MHz, CDCl$_3$): 2.7 (s, 3H), 2.9-4.4 (cm, 5H), 6.4-7.8 (cm, 8H), 7.9 (d, 1H), 8.2 (s, 1H), 9.8 (s, 1H); LCMS: m/z 382 (M+1)$^+$.

Method 19

3-Cyano-N-[(2S)-2-(4-fluorohenyl)-4-oxobutyl]-N-methyl-5,6,7,8-tetrahydronaphthalene-1-carboxamide

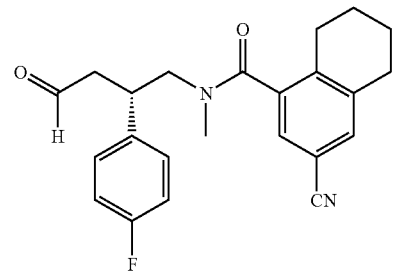

(a) 3-Cyano-N-[(2S)-2-(4-fluorophenyl)pent-4-en-1-yl]-N-methyl-5,6,7,8-tetrahydronaphthalene-1-carboxamide

[(2S)-2-(4-Fluorophenyl)pent-4-en-1-yl]methylamine (see Bioorg. Med. Chem. Lett; 2001; 265-270; 300 mg, 1.55 mmol) was dissolved in $CH_2Cl_2$ (30 m]L) and to the resultant solution were added DIPEA (440 mg, 3.40 mmol) together with 3-cyano-5,6,7,8-tetrahydronaphthalene-1-carbonyl chloride (see WO 00/34243; 341 mg, 1.55 mmol). The mixture was stirred for 2 h at room temperature, diluted with $CH_2Cl_2$ (20 mL) and then washed with water, aqueous $KHSO_4$ solution and finally with brine. The solution was dried over $Na_2SO_4$ and then the solvent was evaporated. The residue was chromatographed on silica gel using a mixture of heptane and ethyl acetate as eluent (7:3) and there was obtained 460 mg (78%) of 3-cyano-N-[(2S)-2-(4-fluorophenyl)pent-4-en-1-yl]-N-methyl-5,6,7,8-tetrahydronaphthalene-1-carboxamide as an oil. $^1$H NMR (400 MHz, $CDCl_3$): 0.8-4.2 (cm, 16H), 4.8-5.1 (m, 2H), 5.6-5.8 (m, 1H), 6.7-7.4 (cm, 6H); LCMS: m/z 377 $(M+1)^+$.

(b) 3-Cyano-N-[(2S)-2-(4-fluorophenyl)-4-oxobutyl]-N-methyl-5,6,7,8-tetrahydronaphthalene-1-carboxamide 3-Cyano-N-[(2S)-2-(4-fluorophenyl)pent-4-en-1-yl]-N-methyl-5,6,7,8-tetrahydronaphthalene-1-carboxamide (460 mg, 1.22 mmol) was dissolved in a mixture of acetone (8 mL), t-butyl alcohol (4 mL) and water (2 mL) under nitrogen. $OsO_4$ (2.5% in t-butyl alcohol, 0.165 mL, 0.01 mmol) was added together with 4-methylmorpholine-4-oxide (630 mg, 5.4 mmol). The solution was stirred at room temperature for 5 h and then an aqueous solution of $NaHSO_3$ (39%, 12 mL) was added. The mixture was stirred for 15 min, diluted with water (50 mL) and then extracted three times with $CH_2Cl_2$. The organic solution was dried over $Na_2SO_4$ and then the solvent was evaporated. The residue (570 mg) is was dissolved in a mixture of THF (7 mL) and water (3 mL) and to the resultant solution was added sodium periodate (287 mg, 1.34 mmol). The mixture was stirred at room temperature overnight, diluted with water (50 mL) and brine (30 mL) and then extracted twice with $CH_2Cl_2$. The organic solution was dried over $Na_2SO_4$ and then the solvent was evaporated. There was obtained 415 mg (89%) of 3-cyano-N-[(2S)-2-(4-fluorophenyl)-4-oxobutyl]-N-methyl-5,6,7,8-tetrahydronaphthalene-1-carboxamide as an oil. $^1$H NMR (400 MHz, $CDCl_3$): 1.4-4.2 (cm, 16H), 6.6-7.4 (cm, 6H), 9.7 (s, 1H); LCMS: m/z 379 $(M+1)^+$.

Method 20

N-[(2S)-2-(4-Fluorophenyl)-4-oxobutyl]-N-methyl-3,5-bis(trifluoromethyl)benzamide

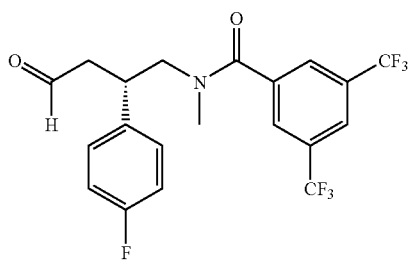

(a) N-[(2S)-2-(4-Fluorophenyl)pent-4-en-1-yl]-N-methyl-3,5-bis(trifluoromethyl)benzamide

[(2S)-2-(4-Fluorophenyl)pent-4-en-1-yl]methylamine (Bioorg. Med. Chem. Lett; 2001; 265-270; 300 mg, 1.55 mmol) was dissolved in DMF (3 mL) and to the resultant solution were added 3,5-bis(trifluoromethyl)benzoic acid (440 mg, 1.71 mmol), TBTU (548 mg, 1.71 mmol) and DIPEA (803 mg, 6.21 mmol) in the given order. The mixture was stirred for 2 h at room temperature, diluted with an aqueous solution of $NaHCO_3$ (saturated, 25 mL) and then extracted three times with ethyl acetate. The combined organic solutions were washed three times with water and then dried over $Na_2SO_4$. The solvent was removed by evaporation and the residue was chromatographed on silica gel using a mixture of heptane and ethyl acetate as eluent (4:1). There was obtained 576 mg (85%) of N-[(2S)-2-(4-fluorophenyl)pent-4-en-1-yl]-N-methyl-3,5-bis(trifluoromethyl) benzamide as an oil. $^1$H NMR (400 MHz, $CDCl_3$): 2.2-2.4 (cm, 2H), 2.7 (s, 2H), 2.9-3.9 (cm, 4H), 4.9-5.1 (m, 2H), 5.4-5.8 (m, 1H), 6.8-7.1 (cm, 3H), 7.2-7.5 (3H), 7.9 (s, 1H); LCMS: m/z 434 $(M+1)^+$.

(b) N-[(2S)-2-(4-Fluorophenyl)-4-oxobutyl]-N-methyl-3,5-bis(trifluoromethyl)benzamide N-[(2S)-2-(4-Fluorophenyl)pent-4-en-1-yl]-N-methyl-3,5-bis(trifluoromethyl)benzamide (570 mg, 1.32 mmol) was dissolved in a mixture of acetone (10 mL), t-butyl alcohol (5 mL) and water (2.5 mL). OsO4 (2.5% in t-butyl alcohol, 0.190 mL, 0.013 mmol) was added together with 4-methylmorpholine-4-oxide (680 mg, 5.8 mmol). The solution was stirred at room temperature overnight and then saturated aqueous solution of $NaHSO_3$ (10 mL) was added. The mixture was stirred for 15 min, diluted with water (50 mL) and then extracted three times with $CH_2Cl_2$. The organic solution was washed with brine and then the solvent was evaporated. The residue (643 mg) was dissolved in a mixture of THF (7 mL) and water (3 mL) and to the resultant solution was added sodium periodate (309 mg, 1.45 mmol). The mixture was stirred at room temperature overnight, diluted with water (75 mL) and brine (40 mL) and then extracted three times with ethyl acetate. The combined organic solutions were washed three times with water, dried over $Na_2SO_4$ and then the solvent was evaporated. The product was purified by chromatography on silica gel using a mixture of heptane and ethyl acetate as eluent (1:1). There was obtained 398 mg (69%) of ) N-[(2S)-2-(4fluorophenyl)-4-oxobutyl]-N-methyl-3,5-bis(trifluoromethyl)benzamide as an oil. $^1$H NMR (400 MHz, $CDCl_3$): 2.6-3.9 (cm, 8H), 6.8-7.6 (cm, 6H), 7.9 (s, 1H), 9.8 (s, 1H); LCMS: m/z 436 $(M+1)^+$.

Method 21

3,5-Dichloro-N-[(2S)-2-(4-fluorophenyl)-4-oxobutyl]-N-methylbenzamide

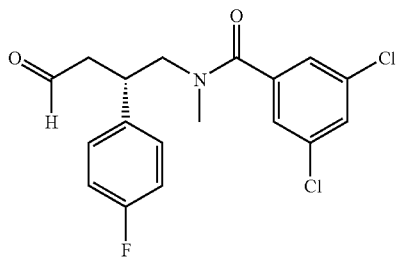

(a) 3,5-Dichloro-N-[(2S)-2-(4-fluorophenyl)pent-4-en-1-yl]-N-methylbenzamide

[(2S)-2-(4-Fluorophenyl)pent-4-en-1-yl]methylamine (see Bioorg. Med. Chem. Lett; 2001; 265-270; 150 mg, 0.78 mmol) was dissolved in CH$_2$Cl$_2$ (5 mL) and to the resultant solution were added DIPEA (221 mg, 1.71 mmol) and 3,5-dichlorobenzoyl chloride (178 mg, 0.85 mmol) in the given order. The mixture was stirred for 4 h at room temperature, diluted with CH$_2$Cl$_2$ (20 mL), and then washed with water (10 mL), aqueous KHSO$_4$ (1M, 10 mL) and brine (10 mL). The organic solution was dried over Na$_2$SO$_4$. The solvent was removed by evaporation and there was obtained 214 mg (75%) of 3,5-dichloro-N-[(2S)-2-(4fluorophenyl)pent-4-en-1-yl]-N-methylbenzamide as an oil. $^1$H NMR (500 MHz, CDCl$_3$): 2.2-2.4 (cm, 2H), 2.6 (s, 2H), 2.9-3.9 (cm, 4H), 4.9-5.1 (m, 2H), 5.5-5.8 (m, 1H), 6.7 (s, 1H), 6.9-7.4 (cm, 6H); LCMS: m/z 367 (M+1)$^+$.

(b) 3,5-Dichloro-N-[(2S)-2-(4-fluorophenyl)-4-oxobutyl]-N-methylbenzamide 3,5-Dichloro-N-[(2S)-2-(4-fluorophenyl)pent-4-en-1-yl]-N-methylbenzamide (210 mg, 0.57 mmol) was dissolved in a mixture of acetone (4 mL), t-butyl alcohol (2 mL) and water (1 mL). OsO$_4$ (2.5% in t-butyl alcohol, 0.080 mL, 0.006 mmol) was added together with 4-methylmorpholine-4-oxide (296 mg, 2.52 mmol). The solution was stirred under nitrogen at room temperature overnight and then an aqueous solution of NaHSO$_3$ (39%, 6 mL) was added. The mixture was stirred for 30 min, diluted with water (25 mL) and then extracted twice with CH$_2$Cl$_2$. The organic solution was dried over Na$_2$SO$_4$ and then the solvent was evaporated. The residue (256 mg) was dissolved in a mixture of THF (3 mL) and water (1 mL) and to the resultant solution was added sodium periodate (135 mg, 0.63 mmol). The mixture was stirred at room temperature overnight, diluted with water (25 mL) and then extracted twice CH$_2$Cl$_2$. The combined organic solutions were dried over Na$_2$SO$_4$ and then the solvent was evaporated. There was obtained 146 mg (69%) of 3,5-dichloro-N-[(2S)-2-(4-fluorophenyl)-4-oxobutyl]-N-methylbenzamide as an oil. $^1$H NMR (400 MHz, CDCl$_3$): 2.6-3.9 (cm, 8H), 6.4-7.4 (cm, 7H), 9.8 (s, 1H); LCMS: m/z 369 (M+1)$^+$.

Method 22

3-Cyano-N-ethyl-N-[(2S)-2-(4-fluorophenyl)-4-oxobutyl]-5,6,7,8-tetrahydronaphthalene-1-carboxamide

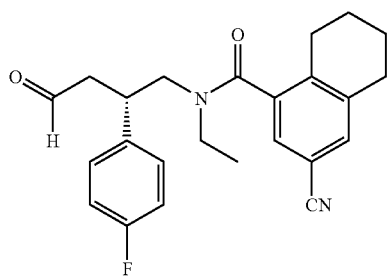

(a) (2S)-2-(4-Fluorophenyl)pent-4-enoyl chloride (2S)-2-(4-Fluorophenyl)pent-4-enoic acid (see Tetrahedron Letters; 2002; 6617-6620; 1.2 g, 6.0 mmol) was dissolved in CH2Cl2 (15 mL) and to the resultant solution was added oxalyl chloride (1.1 g, 9.0 mmol) followed by one drop of DMF. The mixture was stirred for 2 h at room temperature. The solvent was removed by evaporation and there was obtained 1.2 g (98%) of (2S)-2-(4-fluorophenyl)pent-4-enoyl chloride as an oil. $^1$H NMR (300 MHz, CDCl$_3$): 2.6 (q, 1H), 2.9 (q, 1H), 4.1 (t, 1H), 5.0-5.2 (m, 2H), 5.6-5.8 (m, 1H), 7.1 (t, 2H), 7.3 (m, 2H).

(b) (2S)-N-Ethyl-2-(4-fluorophenyl)pent-4-enamide

A stream of ethylamine was introduced to ice-cooled CH$_2$Cl$_2$ (5 mL) until 350 mg gas had been consumed. A solution of (2S)-2-(4-fluorophenyl)pent-4-enoyl chloride (0.24 g in 5 mL of CH$_2$Cl$_2$, 1.1 mmol) was added dropwise. The mixture was stirred at room temperature for 1 h and then diluted with CH$_2$Cl$_2$ (10 mL). The solution was washed with aqueous solutions of KHSO$_4$ (8 mL, 1M), NaOH (8 mL, 1M) and then brine. The organic solution was dried over Na$_2$SO$_4$ and then the solvent was evaporated. There was obtained 0.15 g (59%) of (2S)-N-ethyl-2-(4-fluorophenyl)pent-4-enamide. $^1$H NMR (500 MHz, CDCl$_3$): 1.1 (t, 3H), 2.5 (m, 1H), 2.8-3.0 (m, 2H), 3.2-3.4 (m, 3H), 5.0-5.1 (m, 2H), 5.6-5.8 (m, 1H), 7.0 (t, 2H), 7.3 (m, 2H).

(c) (2S)-N-Ethyl-2-(4-fluorophenyl)pent-4-en-1-amine

LiAlH$_4$ (36 mg, 0.95 mmol) was added to ether (5 mL) at 0° C. under nitrogen. (2S)-N-Ethyl-2-(4-fluorophenyl)pent-4-enamide (140 mg, 0.63 mmol), dissolved in ether (2 mL) was added and the mixture was stirred overnight at room temperature. Water (0.04 mL) was added followed by an aqueous solution of NaOH (0.16 mL, 1M) and the mixture stirred for 30 min. Celite®, MgSO$_4$ and CH$_2$Cl$_2$ was added and the solid material removed by filtration. The solvent was removed by evaporation and there was obtained 0.13 g (100%) of (2S)-N-ethyl-2-(4-fluorophenyl)pent-4-en-1-amine. $^1$H NMR (500 MHz, CDCl$_3$): 1.0 (m, 3H), 2.2-2.9 (m, 5H), 3.2-3.4 (m, 2H), 4.9-5.1 (m, 2H), 5.6-5.7 (m, 1H), 7.0-7.4 (m, 4H). LCMS: m/z 208 (M+1)$^+$.

(d) 3-Cyano-N-ethyl-N-[(2S)-2-(4-fluorophenyl) pent-4-en-1-yl]-5,6,7,8-tetrahydronaphthalene-1-carboxamide (2S)-N-Ethyl-2-(4-fluorophenyl)pent-4-en-1-amine (0.13 g, 0.63 mmol) was dissolved in $CH_2Cl_2$ and to the solution were added DIPEA (0.18 g, 1.4 mmol) and then 3-cyano-5,6,7,8-tetrahydronaphthalene-1-carbonyl chloride (see WO 00/34243; 0.15 g, 0.66 mmol) dissolved in $CH_2Cl_2$ (2 mL). The mixture was stirred for 2 h at room temperature and then diluted with $CH_2Cl_2$. The solution was washed with water, aqueous $KHSO_4$ (10 mL, 1M) and brine. The solvent was removed by evaporation after the solution had been dried. The product was purified by chromatagraphy on silica gel using a gradient of methanol-$CH_2Cl_2$ (0% methanol-5% methanol). There was obtained 0.13 g (53%) of 3-cyano-N-ethyl-N-[(2S)-2-(4-fluorophenyl)pent-4-en-1-yl]-5,6,7,8-tetrahydronaphthalene-1-carboxamide as an oil.

$^1$H NMR (500 MHz, $CDCl_3$): 0.8-1.3 (m, 3H), 1.5-4.2 (cm, 15H), 5.0 (m, 2H), 5.6-5.8 (m, 1H), 6.9-7.4 (m, 6H), LCMS: m/z 391 (M+1)$^+$.

(e) 3-Cyano-N-ethyl-N-[(2S)-2-(4-fluorophenyl)-4-oxobutyl]-5,6,7,8-tetrahydronaphthalene-1-carboxamide The compound was synthesized in an analogous way to that of Method 21b but using 3-cyano-N-ethyl-N-[(2S)-2-(4-fluorophenyl)pent-4-en-1-yl]-5,6,7,8-tetrahydronaphthalene-1-carboxamide rather than 3,5-dichloro-N-[(2S)-2-(4-fluorophenyl)pent-4-en-1-yl]-N-methylbenzamide (yield, 70%). $^1$H NMR (500 MHz, $CDCl_3$): 0.9-4.2 (cm, 18H), 5.9 (s, <1H), 6.9-7.5 (cm, 6H), 8.0 (s, <1H), 9.7 (m, 1H). LCMS: m/z 393 (M+1)$^+$.

Method 23

3-Cyano-N-[(2S)-2-(4-fluorophenyl)-4-oxobutyl]-N-methyl-1-naphthamide

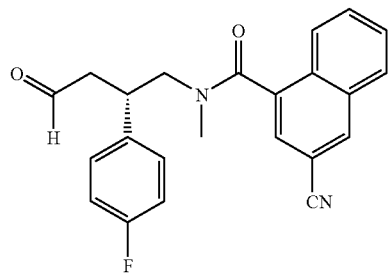

(a) 3-Cyano-N-[(2S)-2-(4-fluorophenyl)pent-4-en-1-yl]-N-methyl-1-naphthamide The compound was synthesized in an analogous way to that of Method 20a but using 3-cyano-1-naphthoic acid (see Bioorg. Med. Chem. Lett. 2001, 2769) rather than 3,5-bis(trifluoromethyl)benzoic acid (yield, 87%). $^1$H NMR (400 MHz, $CDCl_3$): 1.4-4.9 (cm, 8H), 5.0-5.1 (m, 2H), 5.7-5.8 (m, 1H), 6.4 (s, <1H), 6.8-8.0 (cm, 9H), 8.2 (s, 1H).

(b) 3-Cyano-N-[(2S)-2-(4-fluorophenyl)-4-oxobutyl]-N-methyl-1-naphthamide

The compound was synthesized in an analogous way to that of Method 20b but using 3-cyano-N-[(2S)-2-(4-fluorophenyl)pent-4-en-1-yl]-N-methyl-1-naphthamide rather than N-[(2S)-2-(4-fluorophenyl)pent-4-en-1-yl]-N-methyl-3,5-bis(trifluoromethyl)benzamide (yield, 78%). $^1$H NMR (400 MHz, $CDCl_3$): 2.4-2.6 (m, 1H), 2.7 (s, 3H), 2.8-4.4 (cm, 4H), 6.2 (s, <1H), 6.8-7.8 (cm, 9H), 8.2 (s, 1H), 9.8 (s, 1H).

Method 24

3,5-Dibromo-N-[(2S)-2-(4-fluorophenyl)-4-oxobutyl]-N-methlybenzamide

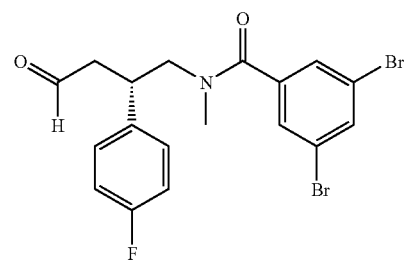

(a) 3,5-Dibromo-N-[(2S)-2-(4-fluorophenyl)pent-4-en-1-yl]-N-methylbenzamide The compound was synthesized in an analogous way to that of Method 20a but using 3,5-dibromobenzoic acid rather than 3,5-bis(trifluoromethyl)benzoic acid (yield, 100%). $^1$H NMR (500 MHz, $CDCl_3$): 2.2-3.2 (cm, 6H), 3.4 (m, 1H), 3.6-3.8 (m, 1H), 5.0 (m, 2H), 5.5-5.8 (m, 1H), 6.8-8.4 (cm, 7H).

(b) 3,5-Dibromo-N-[(2S)-2-(4-fluorophenyl)-4-oxobutyl]-N-methylbenzamide

The compound was synthesized in an analogous way to that of Method 20b but using 3,5-dibromo-N-[(2S)-2-(4-fluorophenyl)pent-4-en-1-yl]-N-methylbenzamide rather than N-[(2S)-2-(4-fluorophenyl)pent-4-en-1-yl]-N-methyl-3,5-bis(trifluoromethyl)benzamide (yield, 96%). $^1$H NMR (400 MHz, $CDCl_3$): 2.6-3.9 (cm, 8H), 6.8-8.2 (cm, 7H), 9.8 (s, 1H).

Method 25

3-Bromo-N-[(2S)-2-(4-fluorophenyl)-4-oxobutyl]-5-iodo-N-methylbenzamide

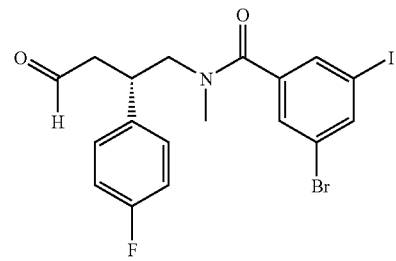

71

(a) 3,5-Dibromo-N-[(2S)-2-(4-fluorophenyl)pent-4-en-1-yl]-N-methylbenzamide

The compound was synthesized in an analogous way to that of Method 21a but using 3-bromo-5-iodobenzoyl chloride (which was prepared in a similar way as in Method 11) rather than 3,5-dichlorobenzoyl chloride (yield, 84%). $^1$H NMR (500 MHz, CDCl$_3$): 2.2-3.8 (cm, 8H), 5.0 (m, 2H), 5.5-5.8 (m, 1H), 6.8-7.4 (cm, 6H), 7.8 (s, 1H), 8.0 (s, <1H).

(b) 3-Bromo-N-[(2S)-2-(4-fluorophenyl)-4-oxobutyl]-5-iodo-N-methylbenzamide

The compound was synthesized in an analogous way to that of Method 21b but using 3-bromo-N-[(2S)-2-(4-fluorophenyl)pent-4en-1-yl]-5-iodo-N-methylbenzamide rather than 3,5-dichloro-N-[(2S)-2-(4-fluorophenyl)pent-4-en-1-yl]-N-methylbenzamide (yield, 100%). $^1$H NMR (500 MHz, CDCl$_3$): 2.6-3.2 (cm, 4H), 3.4-3.9 (cm, 2H), 4.0-4.2, (cm, 2H), 6.8-8.2 (cm, 7H), 9.8 (s, 1H).

Method 26

3-Cyano-N-[2-(4-fluoro-2-methylphenyl)-4-oxobutyl]-N-methyl-5,6,7,8-tetrahydronaphthalene-1-carboxamide

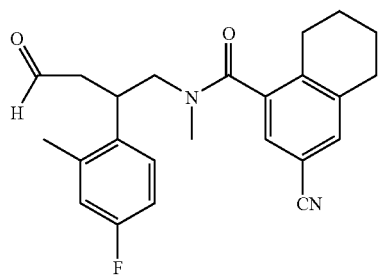

(a) 4-Fluoro-2-methylbenzoic acid

A mixture of 4-fluoro-2-methylbenzonitrile (19.8 g, 150 mmol), KOH (24.3 g, 380 mmol) and water (300 mL) was heated to reflux for two days. The mixture was then acidified with concentrated HCl while cooling. The product was collected by filtration and the filter cake was washed with water. The solid material was dried standing in the hood for several days. There was obtained 20.8 g (92%) of 4-fluoro-2-methylbenzoic acid as a solid material. $^1$H NMR (300 MHz, DMSO-d$_6$): 2.5 (s, 3H), 7.0-7.2 (m, 2H), 7.9 (t, 1H), 12.8 (b, 1H).

(b) Methyl 4-fluoro-2-methylbenzoate

A mixture of 4-fluoro-2-methylbenzoic acid (19.8 g, 128 mmol) and HCl-saturated methanol solution (500 mL) was heated to reflux for 2 h. The solvent was removed by evaporation and the residue partitioned between an aqueous solution of NaHCO$_3$ and CH$_2$Cl$_2$. The organic solution was dried over Na$_2$SO$_4$ and then the solvent was evaporated. There was obtained 15.3 g (71%) of methyl 4-fluoro-2-methylbenzoate as a pale rose oil.

$^1$H NMR (300 MHz, CDCl$_3$): 2.6 (s, 3H), 3.9 (s, 3H), 6.9-7.0 (m, 2H), 7.9 (t, 1H).

(c) (4-Fluoro-2-methylphenyl)methanol

4-Fluoro-2-methylbenzoate (15.3 g, 91 mmol) was dissolved in THF under a stream of nitrogen. The mixture was cooled to 0° C. while adding LiAlH$_4$ (4.4 g, 110 mmol) in small portions and then stirred at room temperature for 1 h. Water (4.4 mL), aqueous 15% NaOH (4.4 mL) and then more water (13.2 mL) were added dropwise in the given order while cooling to 0° C. The mixture was stirred for 2 h and then the solid material was filtered off. The solvent was removed by evaporation and there was obtained 11.5 g (90%) of (4-fluoro-2-methylphenyl)methanol as an oil. $^1$H NMR (300 MHz, CDCl$_3$): 2.4 (s, 3H), 4.6 (s, 2H), 6.8-6.9 (m, 2H), 7.3 (t, 1H).

(d) 1-(Chloromethyl)-4-fluoro-2-methylbenzene (4-Fluoro-2-methylphenyl)methanol (11.5 g, 82 mmol) was dissolved in CH$_2$Cl$_2$ (100 mL). The mixture was cooled to 0° C. before adding SOCl$_2$ (10.7 g, 90 mmol), then stirred for 30 min at 0° C. and then at room temperature for 1.5 h. The solvent and excess of SOCl$_2$ were removed by evaporation followed by the addition of CH$_2$Cl$_2$. The solvent and remaining traces of SOCl$_2$ were evaporated once more. There was obtained 13.0 g (100%) of 1-(chloromethyl)-4-fluoro-2-methylbenzene as an oil. $^1$H NMR (300 MHz, CDCl$_3$): 2.4 (s, 3H), 4.6 (s, 2H), 6.8-7.0 (m, 2H), 7.3 (m, 1H).

(e) (4-Fluoro-2-methylphenyl)acetonitrile 1-(Chloromethyl)-4-fluoro-2-methylbenzene (12.8 g, 81 mmol) was dissolved in CH$_2$Cl$_2$ (50 mL) and to the resultant solution was added a mixture of tetrabutylammonium hydrogensulphate (1.4 g, 4.0 mmol), NaOH (0.32 g, 8.1 mmol) and water (50 mL) followed by an aqueous solution of potassium cyanide (5.0 g, 77 mmol). The mixture was stirred for 5 minutes and then the pH of the aqueous layer was monitored and adjusted to the alkaline side by the dropwise addition of aqueous sodium hydroxide (5M). The mixture was refluxed for one hour, stirred at room temperature overnight and then diluted with CH$_2$Cl$_2$ (50 mL). The organic layer was washed thrice with water and then dried over Na$_2$SO$_4$. The solvent was removed by evaporation and the product was purified by chromatography on silica gel using CH$_2$Cl$_2$. There was obtained 11.1 g (92%) of (4-fluoro-2-methylphenyl)acetonitrile as an oil. $^1$H NMR (300 MHz, CDCl$_3$): 2.3 (s, 3H), 3.6 (s, 2H), 6.8-7.0 (m, 2H), 7.3 (m, 1H).

(f) 2-(4-Fluoro-2-methylphenyl)-4-(tetrahydro-2H-pyran-2-yloxy)butanenitrile (4-Fluoro-2-methylphenyl)acetonitrile (6.0 g, 40 mmol), dissolved in THF (25 mL), was added to a suspension of NaH (2.1 g, 60% in mineral oil, 52 mmol) in THF (25 mL) under a stream of nitrogen. The mixture was then heated to reflux, which initiated the reaction. The reaction proceeded without external heating for 1 h whereupon the visual generation of gas ceased. The mixture was cooled and then 2-(2-bromoethoxy)tetrahydro-2H-pyran (10.9 g, 52 mmol), dissolved in THF (25 mL), was added. The mixture was stirred at 0° C. for 30 min and then at room temperature overnight. The mixture was poured over an aqueous solution of NH$_4$Cl, which was extracted twice with ether. The combined organic solutions were dried over Na$_2$SO$_4$ and then the solvent was evaporated. The product was purified by chromatography on silica gel using CH$_2$Cl$_2$ and there was obtained 8.1 g (72%) of 2-(4-fluoro-2-methylphenyl)-4-(tetrahydro-2H-pyran-2-yloxy)

butanenitrile as an oil. $^1$H NMR (300 MHz, CDCl$_3$): 1.4-2.2 (m, 8H), 2.4 (s, 3H), 3.4-3.6 (m, 2H), 3.8-4.0 (m, 2H), 4.2 (m, 1H), 4.6 (m, 1H), 6.8-7.0 (m, 2H), 7.4 (m, 1H).

(g) [2-(4-Fluoro-2-methylphenyl)-4-(tetrahydro-2H-pyran-2-yloxy)butyl]amine 2-(4-Fluoro-2-methylphenyl)-4-(tetrahydro-2H-pyran-2-yloxy)butanenitrile (4.5 g, 16 mmol) was dissolved in ethanol (40 mL) and concentrated NH$_4$OH aq (20 mL). Raney® nickel suspended in water (one teaspoonful) was added and the mixture was alternately evacuated and flushed with H$_2$. The mixture was then stirred under H$_2$ at room temperature until the consumption of gas ceased. The catalyst was removed with a magnet and the mixture was then filtrated and the solvent was evaporated. There was obtained 4.1 g (90%) of [2-(4-fluoro-2-methylphenyl)-4(tetrahydro-2H-pyran-2-yloxy)butyl]amine as a pale blue oil. $^1$H NMR (500 MHz, CDCl$_3$): 1.4-2.0 (m, 8H), 2.4 (d, 3H), 3.2-3.8 (m, 6H), 4.4-4.6 (d, 1H), 6.9 (d, 2H), 7.1-7.2 (b, 1H).

(h) 3-Cyano-N-[2-(4-fluoro-2-methylphenyl)-4-(tetrahydro-2H-pyran-2-yloxy)butyl]-5,6,7,8-tetrahydronaphthalene-1-carboxamide

[2-(4-Fluoro-2-methylphenyl)-4-(tetrahydro-2H-pyran-2-yloxy)butyl]amine (0.40 g, 1.4 mmol), 3-cyano-5,6,7,8-tetrahydronaphthalene-1-carboxylic acid (see WO 00/34243; 0.32 g, 1.6 mmol) and DCC (0.35 g, 1.7 mmol) were mixed with CH$_2$Cl$_2$ (5 mL). The mixture was stirred at room temperature overnight and then filtrated and the solvent was evaporated. The product was purified by chromatography on silica gel using methanol and CH$_2$Cl$_2$ (0%-2% methanol). There was obtained 600 mg (91%) of 3-cyano-N-[2-(4-fluoro-2-methylphenyl)-4-(tetrahydro-2H-pyran-2-yloxy) butyl]-5,6,7,8-tetrahydronaphthalene-1-carboxamide as a foam. $^1$H NMR (500 MHz, CDCl$_3$): 1.0-1.9 (m, 9H), 2.0-2.1 (m, 1H), 2.4 (d, 3H), 2.6-2.8 (m, 4H), 3.2-3.8 (m, 7H), 4.4-4.5 (d, 1H), 6.0-6.2 (m, 1H), 6.9 (m, 2H), 7.1-7.3 (m, 2H), 7.4 (s, 1H). LCMS: m/z 463 (M−1)$^-$.

(i) 3-Cyano-N-[2-(4-fluoro-2-methylphenyl)-4-(tetrahydro-2H-pyran-2-yloxy)butyl]-N-methyl-5,6,7,8-tetrahydronaphthalene-1-carboxamide

[2-(4-Fluoro-2-methylphenyl) (tetrahydro-2H-pyran-2-yloxy)butyl]amine (0.60 g, 1.3 mmol), Ag$_2$O (1.5 g, 6.5 mmol) and iodomethane (1.8 g, 12.9 mmol) were mixed with DMP (10 mL). The mixture was stirred at room temperature for 3 days, then filtrated and diluted with CH$_2$Cl$_2$ (150 mL). The solution was washed thrice with an aqueous solution of KCN (10 mL 5%) and then thrice with water. The solvent was removed and the residue dissolved in a 1:1 mixture of ethyl acetate and ether. The solution was washed thrice with water, dried over MgSO$_4$ and then the solvent was evaporated. There was obtained 460 mg (74%) of 3-cyano-N-[2-(4-fluoro-2-methylphenyl)-4-(tetrahydro-2H-pyran-2-yloxy)butyl]-N-methyl-5,6,7,8-tetrahydronaphthalene-1-carboxamide as an oil. $^1$H NMR (300 MHz, CDCl$_3$): 1.0-4.5 (cm, 30H), 6.4-7.4 (cm, 5H).

(j) 3-Cyano-N-[2-(4-fluoro-2-methylphenyl)-4-hydroxybutyl]-N-methyl-5,6,7,8-tetrahydronaphthalene-1-carboxamide 3-Cyano-N-[2-(4-fluoro-2-methylphenyl)-4-(tetrahydro-2H-pyran-2-yloxy)butyl]-N-methyl-5,6,7,8-tetrahydronaphthalene-1-carboxamide (460 mg, 0.96 mmol) was dissolved in methanol (10 mL) together with 4-toluenesulfonic acid (37 mg, 0.2 mmol) and the solution was stirred at room temperature overnight. An aqueous solution of NaHCO$_3$ together with CH$_2$Cl$_2$ was added and the organic solution was then washed with brine, dried and the solvent removed by evaporation. There was obtained 350 mg (92%) of 3-cyano-N-[2-(4-fluoro-2-methylphenyl)-4-hydroxybutyl]-N-methyl-5,6,7,8-tetrahydronaphthalene-1-carboxamide as an oil. $^1$H NMR (300 MHz, CDCl$_3$): 1.0-2.3 (cm, 6H), 2.4 (s, 3H), 2.6 (s, 3H), 2.7-4.5 (cm, 10H), 6.4-7.4 (cm, 5H).

(k) 3-Cyano-N-[2-(4-fluoro-2-methylphenyl)-4-oxobutyl]-N-methyl-5,6,7,8-tetrahydronaphthalene-1-carboxamide 3-Cyano-N-[2-(4-fluoro-2-methylphenyl)-4-hydroxybutyl]-N-methyl-5,6,7,8-tetrahydronaphthalene-1-carboxamide (350 mg, 0.89 mmol) was dissolved in CH$_2$Cl$_2$ (15 mL) together with Dess-Martin periodinane (410 mg, 098 mmol) and the mixture was stirred at room temperature for 4 h. Sodium thiosulfate (0.84 g, 5.2 mmol), dissolved in a saturated solution of NaHCO$_3$ aq, was added and the mixture was then stirred vigorously for 1 h. The organic layer was washed with NaHCO$_3$ aq and then brine. The solution was dried over Na$_2$SO$_4$ and the solvent was removed by evaporation. There was obtained 310 mg (89%) of 3-cyano-N-[2-(4-fluoro-2-methylphenyl)-4-oxobutyl]-N-methyl-5,6,7,8-tetrahydronaphthalene-1-carboxamide as an oil. $^1$H NMR (300 MHz, CDCl$_3$): 1.0-4.5 (cm, 19H), 6.6-7.4 (cm, 5H), 9.8 (s, 1H). LCMS: m/z 391 (M−1)$^-$.

Method 27

6-Cyano-N-[(2S)-2-(4-fluorophenyl)-4-oxobutyl]-N-methylindane-4-carboxamide

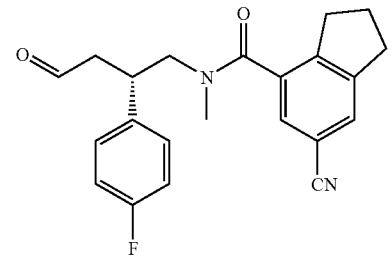

(a) 1-(7-Bromo-2,3-dihydro-1H-inden-5-yl)ethanone

5-Acetylindane (6.3 g, 39 mmol) was dissolved in CH$_2$Cl$_2$ (150 mL) whereupon aluminium chloride (13.0 g, 97 mmol) was added during one minute and a vigorous generation of HCl gas was observed, which was conducted away by means of a tube. The mixture was stirred at room temperature for 5 min and then bromine (9.0 g, 56 mmol), dissolved in CH$_2$Cl$_2$ (50 mL) was added during 2 min. Additional stirring at room temperature for 2 h was followed by pouring the reaction mixture over ice (200 g). The flask was washed with additional CH$_2$Cl$_2$ (100 mL). The organic solution was washed twice with brine, dried and then the solvent was evaporated. There was obtained 8.8 g (93%) of 1-(7-bromo-2,3-dihydro-1H-inden-5-yl)ethanone as a solid material. $^1$H NMR (300 MHz, CDCl$_3$): 2.1-2.2 (q, 2H), 2.6 (s, 3H), 2.9 (t, 2H), 3.1 (t, 2H), 7.7 (s, 1H), 7.9 (s, 1H).

(b) 7-Bromoindane-5-carboxylic acid 1-(7-bromo-2,3-dihydro-1H-inden-5-yl)ethanone (8.6 g, 36 mmol) was dissolved in dimethoxyethane (100 mL) and to the solution were added NaClO aq (200 mL 1M, 200 mmol) and NaOH aq (20 mL 10 M, 200 mmol). The mixture was heated to 50° C. for 1 h and then diluted with water (200 mL). Sodium pyrosulfite (5.7 g, 30 mmol) was added. The mixture was washed with ether, acidified with concentrated HCl and then extracted twice with ether (150 mL). The organic solution was washed with brine, dried and then the solvent was evaporated. The solid residue was treated with cold $CH_2Cl_2$ (−40° C.), then filtered off and dried. There was obtained 7.1 g (82%) of 7-bromoindane-5-carboxylic acid as a solid material. $^1$H NMR (300 MHz, $CD_3OD$): 2.0-2.2 (q, 2H), 2.9 (t, 2H), 3.1 (t, 2H), 7.8 (s, 1H), 7.9 (s, 1H).

(c) 7-Bromoindane-5-carboxamide

7-Bromoindane-5-carboxylic acid (2.9 g, 12 mmol) and oxalylchloride (2.0 g, 16 mmol) were mixed with $CH_2Cl_2$ (50 mL) whereupon DMF (100 mg) was added. After 1 h at room temperature the mixture was poured into a mixture of concentrated $NH_4OH$ aq (20 mL) and ethanol (100 mL). The volatiles were removed by evaporation and the residue partitioned between ethyl acetate (100 mL) and water (50 mL). The organic layer was washed with brine and then dried over $Na_2SO_4$. The solvent was removed by evaporation and the solid residue was treated with cold $CH_2Cl_2$, then filtered off and dried. There was obtained 2.0 g (68%) of 7-bromoindane-5-carboxamide as a solid material. $^1$H NMR (300 MHz, $CD_3CO\ CD_3$): 2.0-2.2 (m, 2H), 2.8-2.9 (d, 2H), 2.9-3.0 (t, 1H), 3.0-3.1 (t, 1H), 6.5 (b, 1H), 7.4 (b, 1H), 7.7 (s, 1H), 7.9 (s,1H).

(d) 7-Bromoindane-5-carbonitrile

7-Bromoindane-5-carboxamide (1.94 g, 8.1 mmol) was suspended in $CH_2Cl_2$ (50 mL) whereupon $POCl_3$ (1.5 g, 9.8 mmol) was added. Triethylamine (3.5 g, 34.6 mmol), dissolved in $CH_2Cl_2$ (10 mL) was added during one minute and an exotermic reaction was observed. The mixture was stirred at room temperature for 30 min and then poured over ice (50 g). The remaining material in the flask was washed out using $CH_2Cl_2$ (50 mL) and water (25 mL). The organic layer was washed twice with brine, dried over $Na_2SO_4$ and then the solvent was evaporated. The solid residue was treated with cold methanol and then filtrated off. The material was washed with cold methanol and then dried. There was obtained 1.2 g (66%) of 7-bromoindane-5-carbonitrile as a solid material. $^1$H NMR (300 MHz, $CDCl_3$): 2.1-2.2 (q, 2H), 2.9-3.1 (m, 4H), 7.4 (s, 1H), 7.6 (s, 1H).

(e) 6-Cyanoindane-4-carboxylic acid

In a flask designed for high pressure (max. 12 bar) 7-bromoindane-5-carbonitrile (1.18 g, 5.3 mmol) was mixed with DMF (50 mL), bis(triphenylphosphine)palladium(II) chloride (0.1 g, 0.14 mmol), triphenylphosphine (0.1 g, 0.38 mmol), triethylamine (1.0 g, 9.9 mmol) and water (5 mL). While stirring the flask was alternately evacuated and then loaded with carbon monoxide. The procedure was repeated 4 times and then carbon monoxide was introduced until a pressure of 6 bar was obtained. The reaction mixture was heated to 90° C. for 60 h and then cooled to room temperature. The content was transferred to a beaker by means of ether (100 mL) and water (200 mL). The organic layer was separated off and precipitated Pd was removed by decantation. The aqueous layer was acidified with conc. HCl and then extracted thrice with ether (50 mL). The combined organic solutions were washed with brine, dried over $Na_2SO_4$ and the solvent was evaporated. The solid residue was treated with cold $CH_2Cl_2$, then filtrated off and then dried. There was obtained 0.6 g (60%) of 6-cyanoindane-4-carboxylic acid as a solid material. $^1$H NMR (300 MHz, $CDCl_3$): 2.1-2.2 (q, 2H), 3.0 (t, 2H), 3.4 (t, 2H), 7.7 (s, 1H), 8.2 (s, 1H).

(f) 6-Cyano-N-[(2S)-2-(4-florophenyl)pent-4-en-1-yl]-N-methylindane-4-carboxamide 6-Cyanoindane-4-carboxylic acid (150 mg, 0.8 mmol) and oxalyl chloride (130 mg, 1.0 mmol) were mixed with $CH_2Cl_2$ (20 mL) whereupon DMF (100 mg) was added. After 1 h at room temperature [(2S)-2-(4-fluorophenyl)pent-4-en-1-yl]methylamine (Bioorg. Med. Chem. Lett; 2001; 265-270; 200 mg, 1.0 mmol) and triethylamine (200 mg, 2.0 mmol) were added to the mixture in the given order. The mixture was stirred at room temperature for 20 min and then the solvent was evaporated. The product was purified by chromatography on silica gel using hexane and ethyl acetate (1:1). There was obtained 180 mg (62%) of 6-cyano-N-[(2S)-2-(4-fluorophenyl)pent-4-en-1-yl]-N-methylindane-4-carboxamide as an oil. $^1$H NMR (300 MHz, $CDCl_3$): 2.0-2.1 (m, 2H), 2.2 (t, 1H), 2.4 (m, 2H), 2.6 (s, 4H), 2.8-3.4 (m, 4H), 3.7 (dd, 1H), 3.8-3.9 (dd, 1H), 4.9-5.1 (m, 2H), 5.4-5.8 (m, 1H), 6.8-7.1 (m, 4H), 7.2 (m, 1H), 7.5 (s, 1H).

(g) 6-Cyano-N-[(2S)-2-(4-fluorophenyl)-4-oxobutyl]-N-methylindane-4-carboxamide The compound was synthesized in an analogous way to that of Method 21b but using 6-cyano-N-[(2S)-2-(4-fluorophenyl)pent-4-en-1-yl]-N-methylindane-4-carboxamide rather than 3,5-dichloro-N-[(2S)-2-(4-fluorophenyl)pent-4-en-1-yl]-N-methylbenzamide (yield, 89%). $^1$H NMR (300 MHz, $CDCl_3$): 0.9-4.2 (cm, 14H), 5.9 (s, <1H), 6.6-8.2 (cm, 6H), 8.0 (s, <1H), 9.8 (s, 1H).

Method 28

3-Fluoro-N-[(2S)-2-(4-fluorophenyl)-4-oxobutyl]-N-methyl-5,6,7,8-tetrahydronaphthalene-1-carboxamide

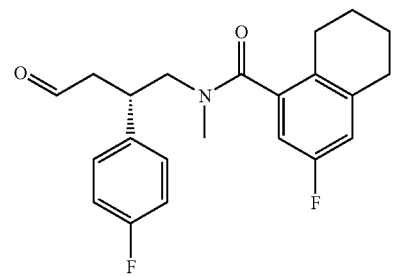

(a) Methyl 3-amino-5,6,7,8-tetrahydronaphthalene-1-carboxylate

Methyl 3-nitro-5,6,7,8-tetrahydronaphthalene-1-carboxylate (see Zh Obshch Khim; 1948, 877-884; 1.4 g, 3 mmol), which was contaminated with its regioisomer methyl 4-nitro-5,6,7,8-tetrahydronaphthalene-1-carboxylate (1:1), was dissolved in methanol (50 mL). The solution was flushed with nitrogen whereupon Pd/C (5%) catalyst (0.19 g) was added. The mixture was stirred under H2 at room temperature until the consumption of gas ceased. The catalyst was removed by filtration and then the solvent was evaporated. The product was separated from its 4-amino regioisomer and by-products by chromatography on silica gel using $CH_2Cl_2$ and triethylamine (98:2). There was obtained 0.24 g (39%) of methyl 3-amino-5,6,7,8-tetrahydronaphthalene-1-carboxylate as an oil. $^1$H NMR (500 MHz, $CDCl_3$): 1.7-1.8 (m, 4H), 2.7 (m, 2H), 2.9 (m, 2H), 3.8 (s, 3H), 6.6 (d, 1H), 7.0 (d, 1H).

(b) Methyl 3-fluoro-5,6,7,8-tetrahydronaphthalene-1-carboxylate

Methyl 3-amino-5,6,7,8-tetrahydronaphthalene-1-carboxylate (0.34 g, 1.7 mmol) was dissolved in aqueous 48% tetrafluoroboric acid (10 mL) and the resultant solution was then diluted with water (10 mL). Sodium nitrite (0.13 g, 1.9 mmol), dissolved in water (1 mL) was added dropwise while cooling with an external ice-water bath. The formed precipitate was isolated by filtration and then washed with diluted tetrafluoroboric acid. The solid material was dried in an exsiccator over $P_2O_5$ and there was obtained 0.27 g of a pale brown powder. A portion of this diazonium salt intermediate (93 mg) was heated to 130° C. until a gas was generated. After further heating to 130° C. for 5 min and cooling to room temperature, the residue was partitioned between ether and saturated $NaHCO_3$ solution. The aqueous layer was extracted with ether and the combined organic solutions were dried over $Na_2SO_4$. The solvent was evaporated and there was obtained 27 mg (23%) of methyl 3-fluoro-5,6,7,8-tetrahydronaphthalene-1-carboxylate as an oil. $^1$H NMR (500 MHz, $CDCl_3$): 1.8 (m, 4H), 2.8 (m, 2H), 3.0 (m, 2H), 3.8 (s, 3H), 6.9 (m, 1H), 7.4 (m, 1H).

(c) 3-Fluoro-5,6,7,8-tetrahydronaphthalene-1-carboxylic acid

A mixture of methyl 3-fluoro-5,6,7,8-tetrahydronaphthalene-1-carboxylate (37 mg, 0.18 mmol), LiOH (27 mg, 1.1 mmol), water (2 mL) and THF (1 mL) was stirred at room temperature overnight and then partitioned between ether and water. The aqueous layer was extracted thrice with ether and then repeatedly with ethyl acetate. The combined organic solutions were dried over $MgSO_4$ and the solvent was removed by evaporation. There was obtained 15 mg (43%) of 3-fluoro-5,6,7,8-tetrahydronaphthalene-1-carboxylic acid as a white solid. $^1$H NMR (500 MHz, $CD_3CO\ CD_3$): 1.8 (m, 4H), 2.8 (m, 2H), 3.1 (m, 2H), 7.0 (m, 1H), 7.6 (m, 1H).

(d) 3-Fluoro-N-[(2S)-2-(4-fluorophenyl)pent-4-en-1-yl]-N-methyl-5,6,7,8-tetrahydronaphthalene-1-carboxamide The compound was synthesized in an analogous way to that of Method 20a but using 3-fluoro-5,6,7,8-tetrahydronaphthalene-1-carboxylic acid rather than 3,5-bis(trifluoromethyl)benzoic acid (yield, 77%). $^1$H NMR (500 MHz, $CDCl_3$): 1.4-4.2 (cm, 16H), 4.8-5.0 (m, 2H), 5.6-5.7 (m, 1H), 6.2-8.2 (cm, 6H).

(e) 3-Fluoro-N-[(2S)-2-(4-fluorophenyl)-4-oxobutyl]-N-methyl-5,6,7,8-tetrahydronaphthalene-1-carboxamide The compound was synthesized in an analogous way to that of Method 20b but using 3-fluoro-N-[(2S)-2-(4-fluorophenyl)pent-4-en-1-yl]-N-methyl-5,6,7,8-tetrahydronaphthalene-1-carboxamide rather than N-[(2S)-2-(4-fluorophenyl)pent-4-en-1-yl]-N-methyl-3,5-bis(trifluoromethyl)benzamide (yield, 68%). $^1$H NMR (500 MHz, $CDCl_3$): 1.6-4.2 (cm, 16H), 6.2-7.8 (cm, 6H), 9.8 (s, 1H).

The invention claimed is:
1. A compound of the formula (I),

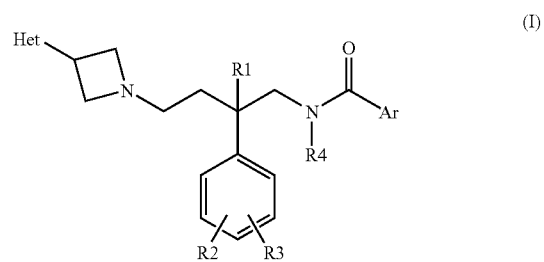

an enantiomer thereof, or a pharmaceutically acceptable salt of the compound or enantiomer, wherein:
Het is selected from the group consisting of:
A) piperidino, wherein the piperidino is:
i) substituted with a substituent selected from the group consisting of hydroxy, hydroxyalkyl, oxo, methylthio, methylsulfinyl, methylsulfonyl, cyano, 1,3-dioxolan-2-yl, $C_1$-$C_4$ alkoxy, amino, acylamino, and ($C_1$-$C_4$ alkylsulfonyl)amino,
wherein the amino is unsubstituted or optionally mono or disubstituted with a substituent selected from the group consisting of $C_1$-$C_4$ alkyl, $C_3$-$C_4$ cycloalkyl, $C_2$-$C_4$ alkenyl, and $C_2$-$C_4$ alkynyl, and
wherein the acylamino and the ($C_1$-$C_4$ alkylsulfonyl)amino are unsubstituted or optionally N-substituted with a substituent selected from the group consisting of $C_1$-$C_4$ alkyl, $C_3$-$C_4$ cycloalkyl, $C_2$-$C_4$ alkenyl, and $C_2$-$C_4$ alkynyl;
ii) substituted with one or two fluoro atoms; or
iii) disubstituted by $C_1$-$C_4$ alkyl and/or hydroxy groups;
B) morpholino or thiomorpholino, wherein the thiomorpholino is unsubstituted or optionally substituted at its sulfur atom by one or two oxygen atoms; and
C) piperazino which is unsubstituted or optionally substituted at the 4-nitrogen atom by a substituent selected from the group consisting of $C_1$-$C_4$ alkyl, $C_2$-$C_4$ alkenyl, $C_2$-$C_4$ alkynyl, $C_3$-$C_4$ cycloalkyl, $C_1$-$C_4$ alkyl sulfonyl, and $C_1$-$C_4$ acyl;
R1 is hydrogen;
R2 is fluoro attached at the 4-position;
R3 is hydrogen;
R4 is selected from the group consisting of $C_1$-$C_4$ alkyl, $C_3$-$C_4$ cycloalkyl, $C_2$-$C_4$ alkenyl, and $C_2$-$C_4$ alkynyl; and
Ar is phenyl substituted at its 3- and 5-positions by substituents independently selected from the group consisting of halogen, $C_1$-$C_4$ alkyl, $C_1$-$C_4$ alkoxy, cyano, and nitro;

wherein one or more of the hydrogen atoms of the alkyl, cycloalkyl, alkenyl, alkynyl, and alkoxy groups may be optionally substituted for a fluorine atom.

2. The compound according to claim 1, wherein R4 is $C_1$-$C_4$ alkyl.

3. The compound according to claim 1, wherein the heterocyclic ring Het is connected to the rest of the molecule at one of the nitrogen atoms of the Het ring.

4. The compound according to claim 1, wherein R4 is methyl.

5. The compound according to claim 1, wherein the compound is an enantiomer.

6. The compound according to claim 1 selected from the group consisting of:
  3,5-Dibromo-N-[(2S)-2-(4-fluorophenyl)-4-(3-morpholin-4-ylazetidin-1-yl)butyl]-N-methylbenzamide;
  N-[2-(4-Fluorophenyl)-4-(3-thiomorpholin-4-ylazetidin-1-yl)butyl]-N-methyl-3,5-bis(trifluoromethyl)benzamide;
  3-Fluoro-N-[(2S)-2-(4-fluorophenyl)-4-(3-morpholin-4-ylazetidin-1-yl)butyl]-N-methyl-5-(trifluoromethyl)benzamide;
  N-[4-[3-(1,4-Dioxa-8-azaspiro[4.5]dec-8-yl)azetidin-1-yl]-2-(4-fluorophenyl)butyl]N-methyl-3,5-bis(trifluoromethyl)benzamide;
  N-{(2S)-2-(4-Fluorophenyl)-4-[3-(4-fluoropiperidin-1-yl)azetidin-1-yl]butyl}-N-methyl-3,5-bis(trifluoromethyl)benzamide;
  N-{(2S)-2-(4-Fluorophenyl)-4-[3-(4-hydroxypiperidin-1-yl)azetidin-1-yl]butyl}-N-methyl-3,5-bis(trifluoromethyl)benzamide;
  3,5-Dichloro-N-[(2S)-2-(4-fluorophenyl)-4-(3-morpholin-4-ylazetidin-1-yl)butyl]-N -methylbenzamide;
  3,5-Dibromo-N-{(2S)-2-(4-fluorophenyl)-4-[3-(4-hydroxypiperidin-1-yl)azetidin-1-yl]butyl}-N-methylbenzamide;
  3-Bromo-N-[(2S)-2-(4-fluorophenyl)-4-(3-morpholin-4-ylazetidin-1-yl)butyl]-5-iodo-N-methylbenzamide;
  N-{2-(4-Fluorophenyl)-4-[3-(1-oxidothiomorpholin-4-yl)azetidin-1-yl]butyl}-N-methyl-3,5-bis(trifluoromethyl)benzamide;
  N-{2-(4-Fluorophenyl)-4-[3-(4-oxopiperidin-1-yl)azetidin-1-yl]butyl}-N-methyl-3,5-bis(trifluoromethyl)benzamide;

or an enantiomer thereof, a salt of the compound, or a salt of the enantiomer.

7. A process for preparing a compound according to claim 1, wherein the process comprises a step selected from the group consisting of:
  a) reacting a compound of the formula (III) with a compound of the formula (IV) under reactive alkylation conditions:

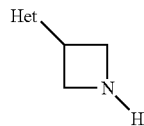
(III)

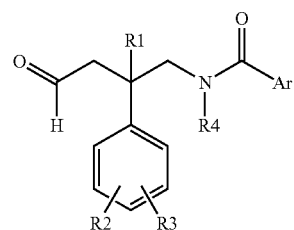
(IV)

wherein R1-R4, Het, and Ar are as defined in claim 1, to form an N—C bond between the nitrogen atom of the azetidine group of the compound of formula (III) and the carbon atom of the aldehyde group of the compound of formula (IV);
  b) reacting a compound of the formula (III) with a compound of the formula (V) under alkylation conditions:

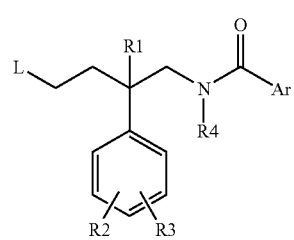
(V)

wherein R1-R4, Het, and Ar are as defined in claim 1, and L is a leaving group, to form an N—C bond between the nitrogen atom of the azetidine group of the compound of formula (III) and the carbon atom of the compound of formula (V) that is adjacent to the L group; and
  c) reacting a compound of the formula (VI) with a compound of the formula (VII):

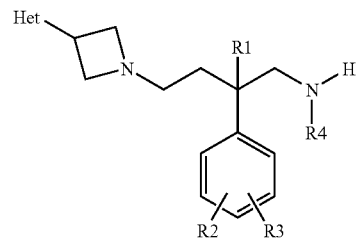
(VI)

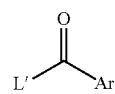
(VII)

wherein R1-R4, Het and Ar are as defined in claim 1, and L' is a leaving group;
  wherein the process optionally further comprises one or more of the following steps:
    i) protecting another functional group in any of compounds (III)-(VII) prior to reaction, and removing the protecting group after reaction;
    ii) oxidizing an oxidizeable atom; and
    iii) forming a pharmaceutically acceptable salt.

8. A compound selected from the group consisting of:
  [2-(4-Fluorophenyl)-4-(3-thiomorpholin-4-ylazetidin-1-yl)butyl]methylamine;

[(2S)-2-(4-Fluorophenyl)-4-(3-morpholin-4-ylazetidin-1-yl)butyl]methylamine;

1-{1-[3-(4-Fluorophenyl)-4-(methylamino)butyl]azetidin-3-yl}piperidin-4-ol;

[4-[3-(1,4-Dioxa-8-azaspiro[4.5]dec-8-yl)azetidin-1-yl]-2-(4-fluorophenyl)butyl]methylamine;

3,5-Dichloro-N-[(2S)-2-(4-fluorophenyl)-4-oxobutyl]-N-methylbenzamide;

3,5-Dibromo-N-[(2S)-2-(4-fluorophenyl)-4-oxobutyl]-N-methylbenzamide; and

3-Bromo-N-[(2S)-2-(4-fluorophenyl)-4-oxobutyl]-5-iodo-N-methylbenzamide;

or an enantiomer of the compound, a salt of the compound, or a salt of the enantiomer.

9. A pharmaceutical formulation comprising as active ingredient a therapeutically effective amount of a compound according to claim 1, wherein the compound is a single enantiomer, a racemate, or a mixture thereof, and wherein the compound is in the form of a free base, a pharmaceutically acceptable salt, a solvate of the free base, or a solvate of the salt, optionally in association with one or more diluents, excipients, or inert carriers.

10. A method of treating pain, the method comprising administering an effective amount of a compound according to claim 1 to a patient in need thereof, wherein the compound is a single enantiomer, a racemate, or a mixture thereof, and wherein the compound is in the form of a free base, a pharmaceutically acceptable salt, a solvate of the free base, or a solvate of the salt.

11. A method for treating a disorder selected from the group consisting of gastrointestinal hypermotility, gastric asthma, Crohn's disease, gastric emptying disorders, ulcerative colitis, irritable bowel syndrome, inflammatory bowel disease, emesis, gastric motility disorders, urinary incontinence, and gastro-esophageal reflux disease (GERD), the method comprising administering an effective amount of a compound according to claim 1 to a patient in need thereof, wherein the compound is a single enantiomer, a racemate, or a mixture thereof, and wherein the compound is in the form of a free base, a pharmaceutically acceptable salt, a solvate of the free base, or a solvate of the salt.

12. The method according to claim 1, wherein the disorder is irritable bowel syndrome.

13. The method according to claim 1, wherein the disorder is inflammatory bowel disease.

14. The method according to claim 1, wherein the disorder is urinary incontinence.

15. A method for the treatment of a medical disorder selected from the group consisting of asthma, allergic rhinitis, chronic obstructive pulmonary disease, airway reactivity, urticaria, hypertension, rheumatoid arthritis, depression, anxiety, and obesity, the method comprising administering an effective amount of a compound according to claim 1 to a patient in need thereof, wherein the compound is a single enantiomer, a racemate, or a mixture thereof, and wherein the compound is in the form of a free base, a pharmaceutically acceptable salt, a solvate of the free base, or a solvate of the salt.

* * * * *

UNITED STATES PATENT AND TRADEMARK OFFICE
CERTIFICATE OF CORRECTION

| | |
|---|---|
| PATENT NO. | : 7,402,581 B2 |
| APPLICATION NO. | : 10/560319 |
| DATED | : July 22, 2008 |
| INVENTOR(S) | : Anders Johansson et al. |

It is certified that error appears in the above-identified patent and that said Letters Patent is hereby corrected as shown below:

Col. 79
Line 14 (Claim 5): "an enantiomer" should read --an S-enantiomer--.

Col. 82
Line 13 (claim 12): "claim 1" should read --claim 11--.
Line 15 (claim 13): "claim 1" should read --claim 11--.
Line 17 (claim 14): "claim 1" should read --claim 11--.

Signed and Sealed this

Fourteenth Day of April, 2009

JOHN DOLL
*Acting Director of the United States Patent and Trademark Office*